(12) United States Patent
Eidenberger

(10) Patent No.: US 8,147,881 B2
(45) Date of Patent: Apr. 3, 2012

(54) STABILIZED ANTHOCYANIN COMPOSITIONS

(75) Inventor: Thomas Eidenberger, Steyr (AT)

(73) Assignee: Omnica GmbH, Hamburg (DE)

( * ) Notice: Subject to any disclaimer, the term of this patent is extended or adjusted under 35 U.S.C. 154(b) by 101 days.

(21) Appl. No.: 12/825,558

(22) Filed: Jun. 29, 2010

(65) Prior Publication Data

US 2011/0217286 A1 Sep. 8, 2011

Related U.S. Application Data

(62) Division of application No. 12/047,993, filed on Mar. 13, 2008, now Pat. No. 7,820,207.

(60) Provisional application No. 60/895,034, filed on Mar. 15, 2007, provisional application No. 60/952,113, filed on Jul. 26, 2007, provisional application No. 60/985,603, filed on Nov. 5, 2007.

(51) Int. Cl.
*A01N 65/00* (2009.01)

(52) U.S. Cl. ........................................................ 424/725

(58) Field of Classification Search ........................ None
See application file for complete search history.

(56) References Cited

U.S. PATENT DOCUMENTS

| | | | |
|---|---|---|---|
| 4,211,577 A | 7/1980 | Wallin |
| 4,268,265 A | 5/1981 | Von Wattenwyl |
| 4,302,200 A | 11/1981 | Yokoyama et al. |
| 5,008,110 A | 4/1991 | Benecke et al. |
| 5,087,240 A | 2/1992 | Sibalis |
| 5,088,977 A | 2/1992 | Sibalis |
| 5,163,899 A | 11/1992 | Sibalis |
| 5,164,189 A | 11/1992 | Farhadieh et al. |
| 5,200,186 A | 4/1993 | Gabetta et al. |
| 5,254,346 A | 10/1993 | Tucker et al. |
| 5,290,561 A | 3/1994 | Farhadieh et al. |
| 5,332,213 A | 7/1994 | Klose |
| 5,336,168 A | 8/1994 | Sibalis |
| 5,352,456 A | 10/1994 | Fallon et al. |
| 5,407,713 A | 4/1995 | Wilfong et al. |
| 5,817,354 A | 10/1998 | Mozaffar et al. |
| 5,912,363 A | 6/1999 | Nafisi-Movaghar et al. |
| 5,925,620 A | 7/1999 | Ohlenschlager et al. |
| 6,171,602 B1 | 1/2001 | Roman |
| 6,569,446 B1 | 5/2003 | Howard |
| 6,818,234 B1 | 11/2004 | Nair et al. |
| 7,820,207 B2 | 10/2010 | Eidenberger |
| 2001/0031744 A1 | 10/2001 | Kosbab |
| 2002/0018821 A1 | 2/2002 | Soulier et al. |
| 2003/0027747 A1 | 2/2003 | Yatcilla et al. |
| 2007/0082064 A1 | 4/2007 | Krawitz |
| 2008/0255226 A1 | 10/2008 | Eidenberger |

FOREIGN PATENT DOCUMENTS

| | | |
|---|---|---|
| EP | 1 474 999 | 4/2004 |
| WO | WO 92/03146 | 3/1992 |

OTHER PUBLICATIONS

MacCarone, Emanuele et al., "Stabilization of Anthocyanins of Blood Orange Fruit Juice", vol. 50, (1985), Journal of Food Science, pp. 901-904, XP002516584.

Vaimakis V., et al., "Must oxygenation Together with Gluatathione Addition in the Oxidation of White Wine:", Food Chem., vol. 67, No. 3, (1996), pp. 419-422, XP002516585.

Mary Ann Lila, "Anthocyannis and Human Health: An in Vitro Investigative Approach", Journal of Biomedicine and Biotechnology, (2004):5, pp. 306-313.

Talavera, Severine et al., Anthocyannis are Efficiently Absorbed from the Small Intestine in Rats:, Apr. 2004, American Society for Nutritional Sciences, Nutrient Metabolism, pp. 2275-2279.

Talavera, Severine et al., "Anthocyanins are Efficiently Absorbed from the Stomach in Anesthetized Rates", Jul. 2003, American Society for Nutritional Sciences, Nutrient Metabolism, pp. 4178-4182.

Marco, Paulo H. et al., "Exploratory Anaylsis of Simultaneous Degradation in the Calyces of Flowers of the Hibiscus Sabdariffa Species by PARAFAC Model", Analytical Sciences, The Japan Society for Analytical Chemistry, Dec. 2005, vol. 21, pp. 1523-1527.

*Primary Examiner* — Michael Meller
(74) *Attorney, Agent, or Firm* — Scott D. Rothenberger; Colin L. Fairman; Fulbright & Jaworski

(57) ABSTRACT

The invention describes stabile anthocyanin compositions, methods to prepare such compositions and also methods of use of such compositions to treat various afflictions. The present invention describes unique compositions of an anthocyanin and a stabilizing compound such that the combination of the two components provides that the anthocyanin does not readily undergo degradation, such as oxidation, pH instability, etc.

3 Claims, 27 Drawing Sheets

Figure 5
% residual anthocyanosides of bilberry extract (GSH protected)
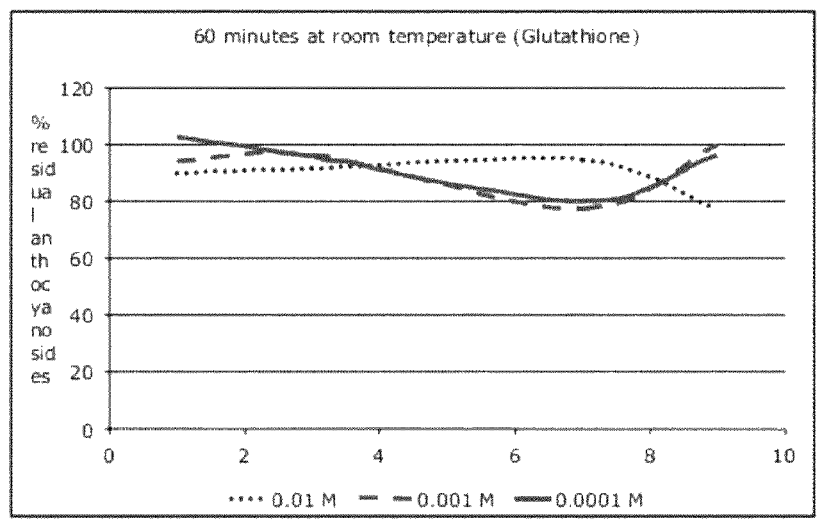
Figure 6A through 6D
Comparative degradation kinetics of bilberry extract (DHLA-protected)
Figure 6A
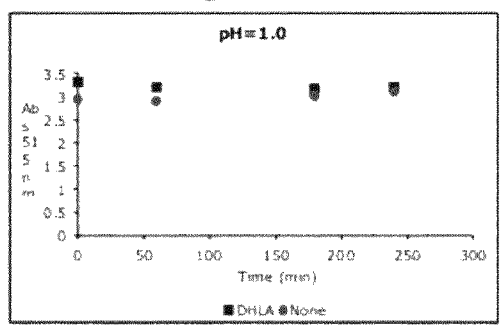
Figure 6B
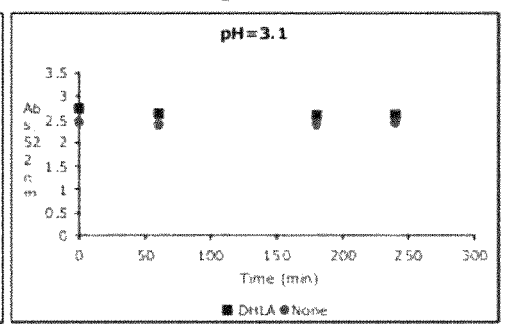

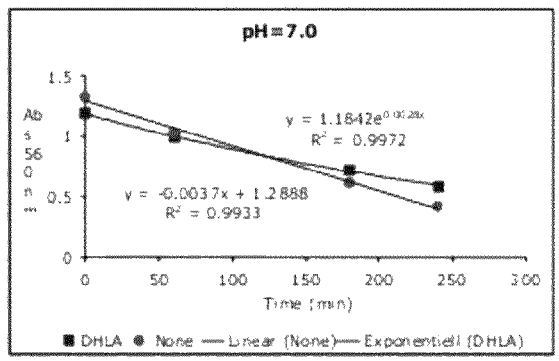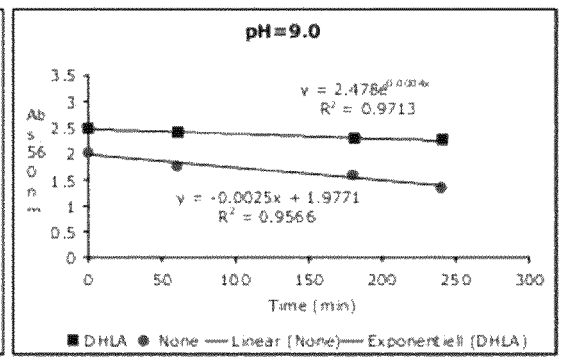
Figure 6C    Figure 6D
Figure 7
Comparative degradation kinetics of delphinidin-3-O-galactoside
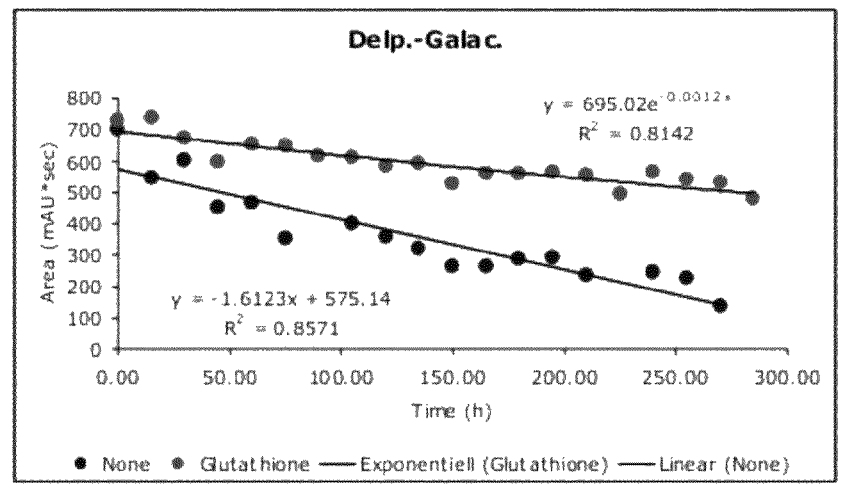

Comparative degradation kinetics of petunidin-3-O-galactoside

Comparative degradation kinetics of delphinidin-3-O-galactoside

Comparative degradation kinetics of cyanidin-3-O-galactoside
(red line... unprotected, blue line... GSH protected)

Cellular uptake of lead-anthocyanosides into CaCo-2 cells

Degradation of bilberry anthocyanosides with/without glutathione (1 hour at 37 °C, pH=7.0)

Legend: Dp... Delphinidin, Cn... Cyanidin, Pt... Petunidin, Pe... Peonidin, Mv... Malvidin; Gal... Galactose, Glc... Glucose, Ara... Arabinose (Anthocyanosides are listed in accordance with elution from the HPLC)

Legend: Dp... Delphinidin, Cn... Cyanidin, Pt... Petunidin, Pe... Peonidin, Mv... Malvidin; Gal... Galactose, Glc... Glucose, Ara... Arabinose (Anthocyanosides are listed in accordance with elution from the HPLC)

Residual Ratio and pH value

The Protection Effect and pH value

HPLC graph of fresh solution of 20070601

HPLC graph of final solution of 20070601

HPLC graph of fresh solution of 20070602

HPLC graph of final solution of 20070602

Figure 27
Comparison of anthocyanidins observed in human plasma after treatment with bilberry or Bilberry/Cysteine combo
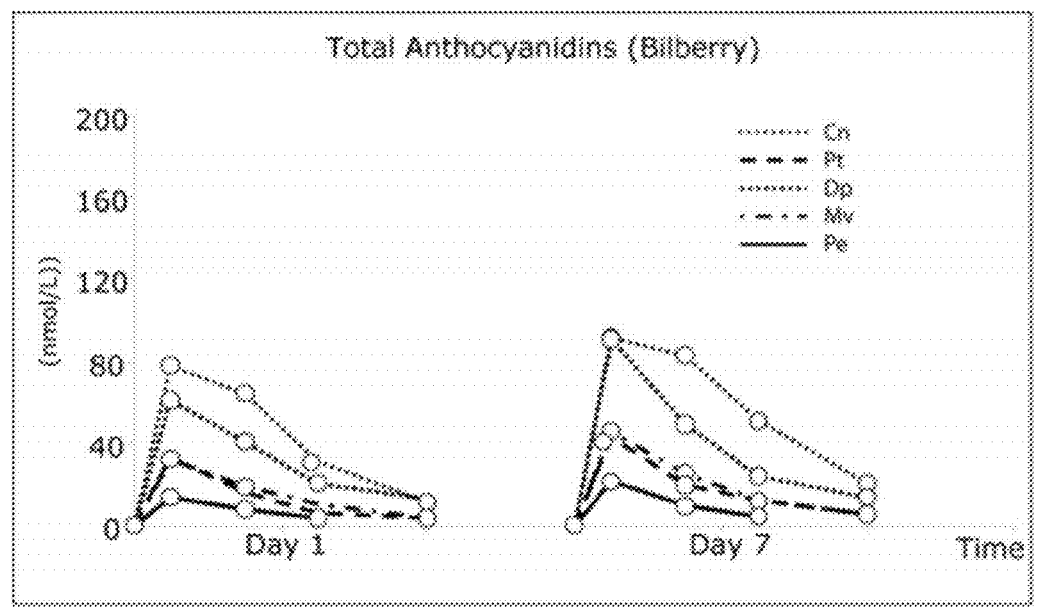
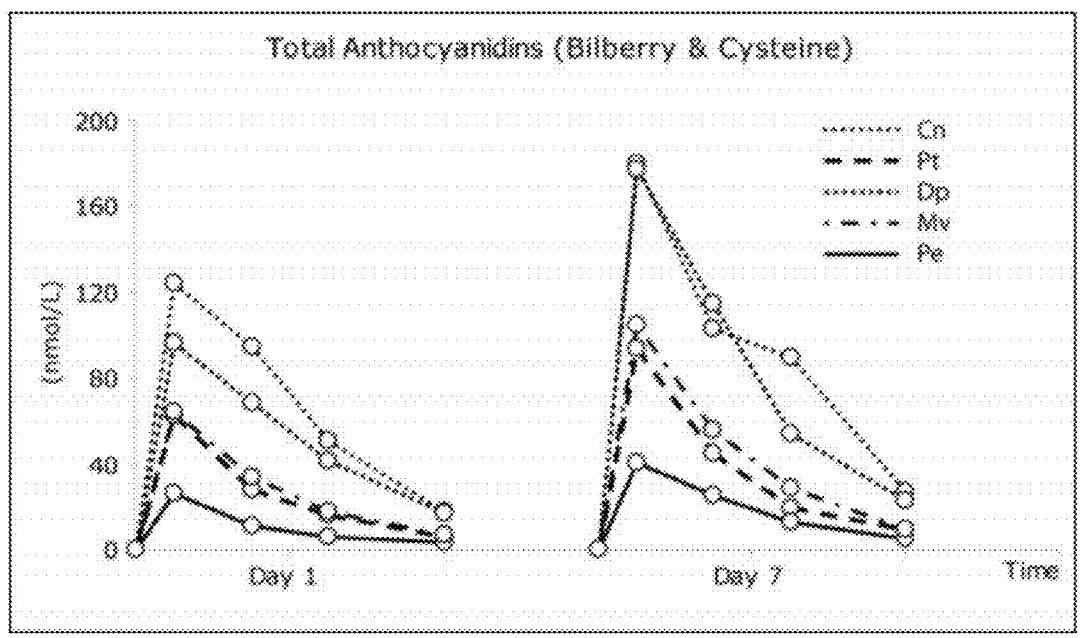

Figure 28a
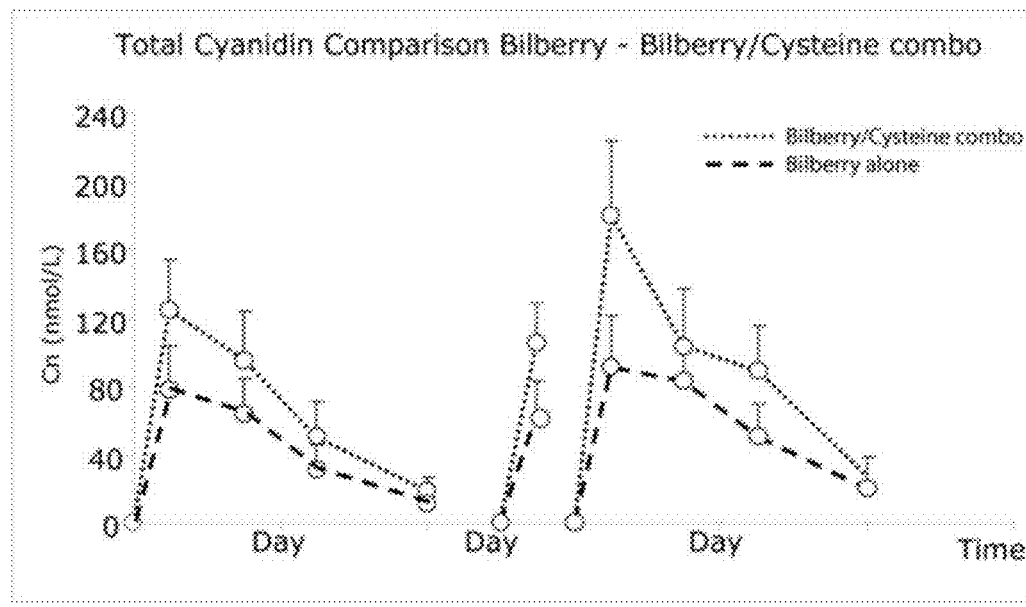
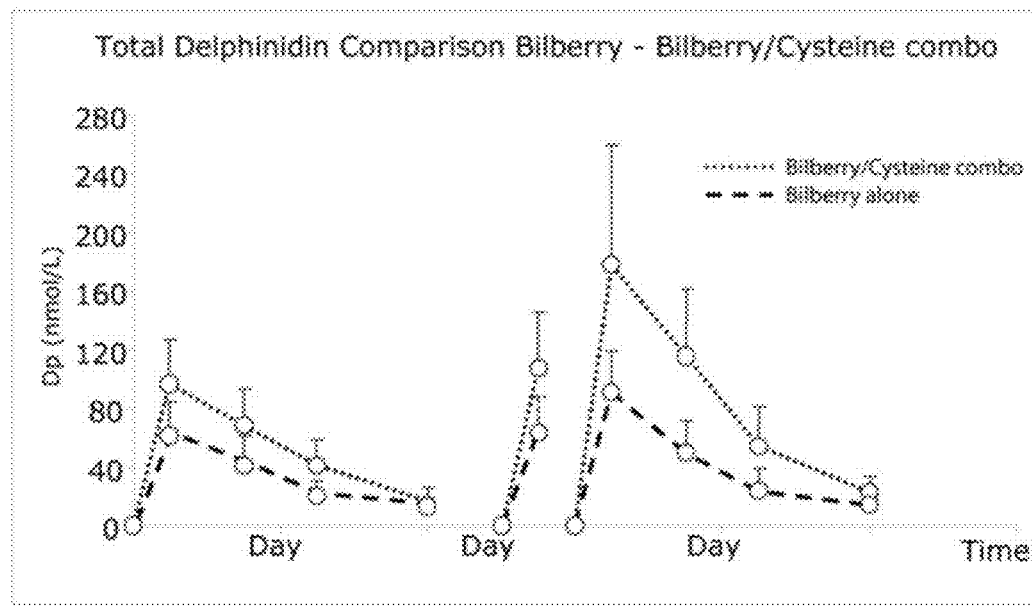
Figure 28b

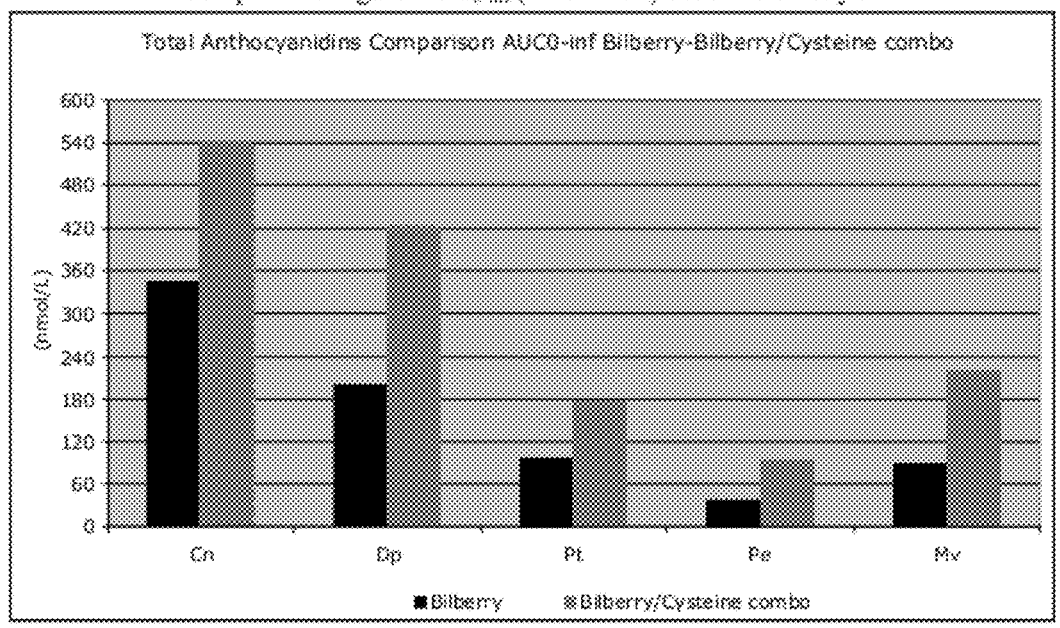

TOTAL CYANIDIN PLASMA LEVELS (NG/ML), MEAN± S.D.

TOTAL PETUNIDIN PLASMA LEVELS (NG/ML), MEAN± S.D.

TOTAL PEONIDIN PLASMA LEVELS (NG/ML), MEAN ± S.D.

TOTAL MALVIDIN PLASMA LEVELS (NG/ML), MEAN± S.D.

STABILIZED ANTHOCYANIN COMPOSITIONS

CROSS REFERENCE TO RELATED APPLICATIONS

This application is a Divisional of U.S. patent application Ser. No. 12/047,993, filed Mar. 13, 2008, now U.S. Pat. No. 7,820,207 which claims benefit of U.S. Ser. No. 60/895,034 filed on Mar. 15, 2007, U.S. Ser. No. 60/952,113 filed Jul. 26, 2007, and U.S. Ser. No. 60/985,603 filed Nov. 5, 2007, the contents of each of which are incorporated in their entirety herein by reference.

FIELD OF THE INVENTION

The invention relates generally to methods and compositions useful to stabilize anthocyanins and anthocyanidins.

BACKGROUND OF THE INVENTION

Anthocyanins are water soluble pigments which are responsible for the attractive colors of many flowers, fruit and leaves. Generally, they can be extracted from plants by acidified alcoholic solvents and many are available commercially as food colorants. They are often supplied with malto dextrin as a diluent in a concentration suitable for inclusion in beverages or other foods such as cereals.

Anthocyanidines, the aglyconic component of anthocyanins, have a basic structure as shown in Formula I.

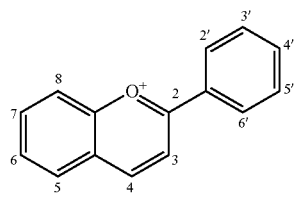

Formula I

Typical examples are: cyanidin (hydroxylated at positions 3, 5, 7, 3', 4'), delphinidin (hydroxylated at positions 3, 5, 7, 4', 5') and pelargonidin (hydroxylated at positions 3, 5, 7, 3'). The hydroxyl groups are usually glycosylated (e.g., an anthocyanin) and/or methoxylated (e.g. malvidin is substituted at the 3' and 5' hydroxyl groups and paeonidin and petunidin are substituted at the 3' hydroxyl group).

Anthocyanins are water-soluble glycosides of polyhydroxyl and polymethoxyl derivatives of 2-phenylbenzopyrylium or flavylium salts. Individual anthocyanins differ in the number of hydroxyl groups present in the molecule, the degree of methylation of these hydroxyl groups, the nature, number and location of sugars attached to the molecule and the number and the nature of aliphatic or aromatic acids attached to the sugars in the molecule. Hundreds of anthocyanins have been isolated and chemically characterized by spectrometric tools. Cyanidins and their derivatives are the most common anthocyanins present in vegetables, fruits and flowers.

Anthocyanins share a basic carbon skeleton in which hydrogen, hydroxyl or methoxyl groups can be found in six different positions as noted above. In fruits and vegetables, six basic anthocyanin compounds predominate, differing both in the number of hydroxyl groups present on the carbon ring and in the degree of methylation of these hydroxyl groups. The identity, number and position of the sugars attached to the carbon skeleton are also variable; the most common sugars that can be linked to carbon-3, carbon-5 and, sometimes, carbon-7, are glucose, arabinose, rhamnose or galactose. On this basis, it is possible to distinguish monosides, biosides and triosides.

Another important variable that contributes to the chemical structure of anthocyanins is the acylating acid that can be present on the carbohydrate moiety. The most frequent acylating agents are caffeic, ferulic, sinapic and p-coumaric acids, although aliphatic acids such as acetic, malic, malonic, oxalic and succinic acids can also occur. Up to three acylating acids can be present simultaneously.

Due to their particular chemical structure, anthocyanins and anthocyanidins are characterized by an electron deficiency, which makes them very reactive toward reactive oxygen species (ROS), also known as free radicals; they are consequently considered to be powerful natural antioxidants.

Anthocyanins, due in part to the nature of their chemical structure, tend to be unstable and susceptible to degradation. Additionally, the stability of anthocyanins is effected by pH, storage over a period of months, storage temperature, presence of enzymes, light, oxygen, and the presence of proteins, flavonoids and minerals More particularly, the bioavailability of anthocyanins is low due to their sensitivity to changes in pH. Anthocyanins are generally stable at pH values of 3.5 and below, and are therefore stable under stomach conditions. However, they degrade at higher pH values, such as those more typical for the intestinal tract (pH of 7) and thus beneficial absorption and nutritional value is greatly reduced.

Therefore, a need exists for a composition and/or method that provides stabilized anthocyanins.

BRIEF SUMMARY OF THE INVENTION

The present invention surprisingly provides stabile anthocyanin compositions, methods to prepare such compositions and also methods of use of such compositions to treat various afflictions. The present invention provides unique compositions of an anthocyanin and a stabilizing compound such that the combination of the two components provides that the anthocyanin does not readily undergo degradation. Up until the time of the invention, it was known that anthocyanins would degrade upon exposure to environmental stresses, such as air, light, proteins, or enzymes. More troublesome was the instability of anthocyanins in solutions having a neutral or basic pH.

Surprisingly, the present invention provides that use of cysteine in combination with an anthocyanin composition (whether it be an anthocyanidine or an anthocyanoside) helps to increase the delivery of the anthocyanin to a subject in need thereof by at least twice the amount relative to a subject that ingests an anthocyanin composition without the presence of cysteine. It has been surprisingly found that plasma concentration levels of the anthocyanin where the anthocyanin is delivered in the presence of cysteine after 4 hours is at least twice the plasma concentration of an anthocyanin delivered without the cysteine. Therefore, the present invention provides a method to increase the amount of bioavailable anthocyanin in a subject by administering to the subject an effective amount of an anthocyanin and cysteine. The administration can be by any means, but oral delivery is generally preferred. In one embodiment, the ratio of the anthocyanin to the cysteine is about 10 to about 1, on a weight basis.

In one aspect, the present invention provides a stabilized anthocyanin extract composition that includes an anthocyanin extract and a stabilizing compound having at least one —SH group. Suitable examples of stabilizing compounds include (reduced) glutathione, dihydrolipoic acid, cysteine, yeast extract and mixtures thereof.

Although there are literally thousands of anthocyanin extracts, all of which should be considered included within the realm of this specification, suitable examples of anthocyanin extracts of particular interest include bilberry extract, blackcurrant extract, cranberry extract, black soybean extract, cowberry extract, blueberry extract and mixtures of two or more thereof.

In one aspect, the ratio of stabilizing compound to anthocyanin extract is about 0.1 to about 10, more particularly about 0.5 to about 5, and more particularly about 1 to about 1.

In another aspect, the stabilized anthocyanin extract composition is stabile toward degradation when exposed to an aqueous environment with a pH of about 2 or greater, such as a pH of about 3, of about 4, of about 5, pH of about 6, pH of about 7 pH of about 8, of about 9, of about 10, or about 11, of about 12 or even higher, e.g. 14.

In still another aspect, the stabilized anthocyanin extract is an anthocyanoside.

In still yet another aspect, the stabilized anthocyanin extract is an anthocyanidin.

In still other aspects of the invention, the stabilized anthocyanin extract includes one or more anthocyanosides that are glycosidse of perlargonidin, peonidin, cyanidin, malvidin, petunidin, delphinidin.

The present invention also pertains to methods of preparing the stabilized anthocyanin compositions described herein.

The present invention further pertains to methods of treatment of various ailments by administration of a therapeutically effective amount of the stabilized anthocyanin compositions described herein.

Therefore, the present invention further provides bioavailable stabilized anthocyanin compositions.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

BRIEF DESCRIPTION OF THE DRAWINGS

FIG. 5 provides percent residual anthocyanosides of bilberry extract that is GSH protected in contrast to unprotected seen in FIG. 3.

FIGS. 6A through 6D provide comparative degradation kinetics of bilberry extract that is DHLA-protected.

FIG. 7 provides comparative degradation kinetics of delphinidin-3-O-galactoside that is unprotected or protected with glutathione.

FIG. 27 provides a comparison of anthocyanidins observed in human plasma after treatment with bilberry extract or a bilberry/cysteine combination of the invention.

FIGS. 28a and 28b provides a comparison of total cyandin and delphinidin, respectively, observed in human plasma after treatment with bilberry extract or a bilberry/cysteine combination of the invention. Upper dotted line is bilberry/cysteine combination; lower hashed line is bilberry extract only.

FIG. 35 provides comparative $AUC_{0\text{-}inf}$ observed on day 7 for cyandin, delphinidin, petunidin, peonidin and malvidin for bilberry extract versus a bilberry extract/cysteine combination.

DETAILED DESCRIPTION

Figure 1:
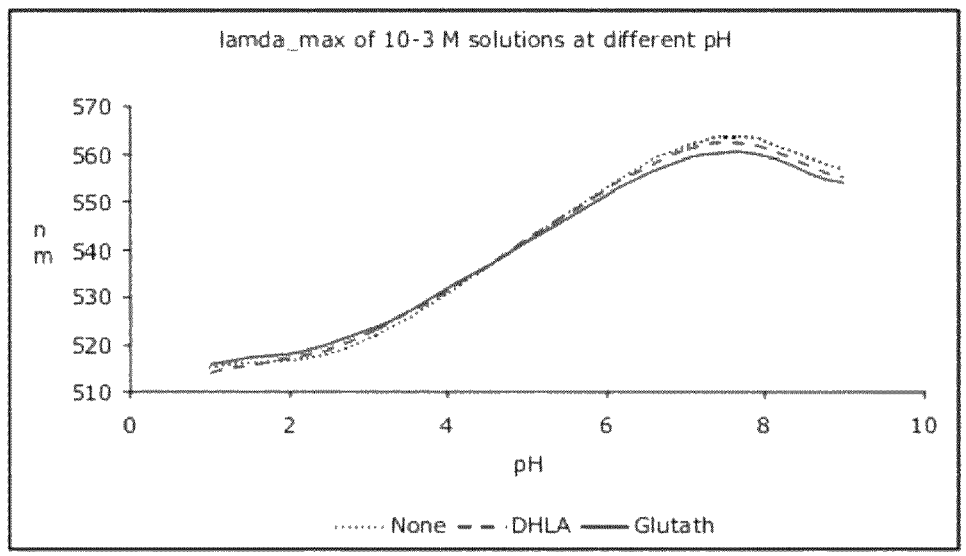
FIG. 1 provides evidence of a lack of bathochromic shift for cy-3-O-glucoside in a 1 mMolar solution of glutathione or DHLA.

The present invention relates to compositions containing one or more anthocyanins and one or more stabilizing compounds. The compositions are thus "stabile" in that the anthocyanin does not readily degrade over a given period of time.

In the specification and in the claims, the terms "including" and "comprising" are open-ended terms and should be interpreted to mean "including, but not limited to . . . ." These terms encompass the more restrictive terms "consisting essentially of and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

In one aspect, the present invention provides a stabilized anthocyanin composition that includes an anthocyanin extract and a stabilizing compound having at least one —SH group.

The term "anthocyanin" as used herein is intended to include both glycosylated anthocyanins (anthocyanosides) as well as the aglycon of the anthocyanoside (anthocyanidin). Throughout the specification, reference to the aglyconic anthocyanidin will often be made but should in no way be construed as limiting unless otherwise noted. Wherein either term is used, unless otherwise noted, the terms are used interchangeably and are intended to include the glycosylated as well as aglyconic materials.

Anthocyanidines, the aglyconic component of anthocyanins, have a basic structure as shown in Formula II

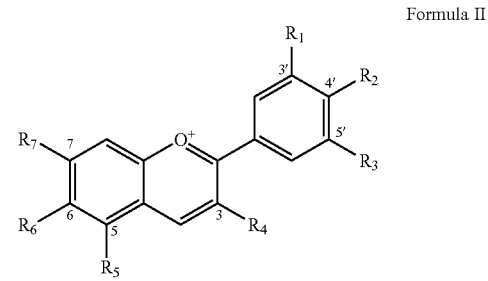

Formula II

| Anthocyanidin | $R_1$ | $R_2$ | $R_3$ | $R_4$ | $R_5$ | $R_6$ | $R_7$ |
|---|---|---|---|---|---|---|---|
| Auantinidin | H | OH | H | OH | OH | OH | OH |
| Cyanidin | OH | OH | H | OH | OH | H | OH |
| Delphinidin | OH | OH | OH | OH | OH | H | OH |
| Europinidin | $OCH_3$ | OH | OH | OH | $OCH_3$ | H | OH |
| Luteolinidin | OH | OH | H | H | OH | H | OH |
| Pelargonidin | H | OH | H | OH | OH | H | OH |
| Malvidin | $OCH_3$ | OH | $OCH_3$ | OH | OH | H | OH |
| Peonidin | $OCH_3$ | OH | H | OH | OH | H | OH |
| Petunidin | OH | OH | $OCH_3$ | OH | OH | H | OH |
| Rosinidin | $OCH_3$ | OH | H | OH | OH | H | $OCH_3$ | where $R_1$ through $R_7$ provide representative examples of anthocyanidins.

The glycosylated forms of anthocyanins are more water soluble and stable than anthocyanidins. Anthocyanosides are classified by the number of glycosyl units they contain. Monoglycosides include one saccharidic moiety, which is primarily attached to the 3-hydroxyl group of the aglycon. Diglycosides generally contain two monosaccharides at the 3 and 5 hydroxy positions and occasionally at the 3 and 7 hydroxyl positions. Triglycosides have attachment generally where there are two units at the 3 position and one at the C-5 or C-7 position. Glycosylations at the 3', 4' and/or 5' positions are also possible.

The most common sugars of anthocyanins include the monosaccharides glucose, rhamnose, galactose, arabinose and xylose. The di- and trisaccharides found most often in anthocyanins are rutinose, sophorose, sambubiose and glucorutinose.

Anthocyanins can be acylated through one or more hydroxyls with a carboxylic acid. The acids are most commonly linked to the 6 position of the monosaccharide but the 2, 3 and 4 positions of the monosaccharides are also possible. Common aliphatic acids include malonic, acetic, malic, succinic, and oxalic acids. Common aromatic phenolic acids and aliphatic dicarboxylic acids include coumaric, acffeic, sinapic, ferulic, oxalic, malonic, malic, succinic and gallic acid.

The term "extract" is intended to mean anthocyanin materials obtained from plant sources, such as leaves, twigs, bark, roots, stem, seeds, flowers, berries, fruit, for example, by routine isolation methods from suitable plants sources noted, but not limited to, those described herein. There are various methods for the extraction of anthocyanins known to those of skill in the art. Some of these methods are described in, for example, U.S. Pat. Nos. 5,817,354; 5,200,186; 5,912,363; 4,211,577; 4,302,200 (each incorporated herein by reference).

Examples of suitable anthocyanin-containing plants include, but are not limited to, fruits, vegetables, flowers and other plants selected from the group consisting of *Acer macrophyllum*, *Acer platanoides*, acerola, *Ajuga reptans*, apple, apricot, *Artict bramble*, avocado, banana, barberry, barley, *Begonia semperfiorens*, *Bellis perennis*, *Bletilla striata*, bilberry, black beans, black soybeans, black, blue and purple potatoes, blackberry, blueberry, bog whortleberry, boysenberry, buckwheat, cacao, *Camellia sinensis*, canarygrass, Caucasian blueberry, *Chimonanthus praecox*, celery, *Cerasus avium*, cherry, cherry laurel, chicory, chive, chokeberry, Cornelian cherry, cornflower, cotoneaster, cowberry, cranberry, crowberry, chrysanthemum, *Cynomorium coccineum*, *Dahlia variabilis*, danewort, deerberry, *Dendrobium*, dwarf dogwood, *Echinacea purpea*, eggplant, elderberry, fababean, *Fatsia japonica, feijoa*, fig, garlic, *gerbera, ginseng*, Globe artichoke, gooseberry, grapes, guava, hawthorn, *hibiscus* or *roselle, Hibiscus Sabdaiffa*, highbush blueberry, hollyhock, honeysuckle, *Ipomoea purpurea, Iris ensata*, Java plum, Jerusalem artichoke, kokum, *Laeliocattleya*, lentil, loganberry, lupine, lychee, maize, mango, mangosteen, maqui, *Matthiola incana, meconopsis, Metrosideros excelsa*, millet, mountain ash berry, mulberry, myrtle berry, olive, onion, orange, ornamental cherry, passion fruit, pea, peach, peanut, pear, *perilla, petunia, Phalaenopsis, Phalsa, Pharbitis*, Pineapple, pistachio, plum, pomegranate, *Phragmites australis*, purple carrot, quince, rabbiteye blueberry, radish, red and black currant, red and black raspberry, red cabbage, rice, rhubarb, rosehip, rye, saffron, *sarracenia,* sheepberry, *Sophronitis coccinea, sorghum,* sparkleberry, strawberry, *Fragada Vesca*, sugarcane, sunflower, sweet cherry, sweet potato, tamarillo, tamarind, taro, tart cherry, *Tulip greigii*, turnip, water lily, *Weigela*, wheat, wild rice, *Verbena hybrida*, yam and mixtures thereof.

Although there are literally thousands of anthocyanin extracts, all of which should be considered included within the realm of this specification, suitable examples of anthocyanin extracts of particular interest include bilberry extract, blackcurrant extract, cranberry extract, black soybean extract, cowberry extract, blueberry extract and mixtures of two or more thereof.

Typically the extract is concentrated by various methods to provide a solution enriched in anthocyanins. For example, ultrafiltration can be used to remove unwanted components by molecular weight cut offs. The retentate from the filtration can be stored as a liquid or, for example, can then be further concentrated into a powder by spray drying, freeze drying, flash drying, fluidized bed drying, ring drying, tray drying, vacuum drying, radio frequency drying or microwave drying. Ultimately, the extract should contain at least 10% by weight anthocyanin content. Commercially available anthocyanins can be obtained from sources such as Artemis International, Fort Wayne, Indiana. Commercially obtained anthocyanin extracts should contain at least 10% by weight anthocyanin content. The extracts, therefore, contain anthocyanin(s) and other plant materials such as other flavinoids, sugars, etc.

Anthocyanin extracts can be further purified by one or more methods known in the art, such as chromatography, gel chromatography, high performance liquid chromatography, crystallization, affinity chromatography, partition chromatography and the like. Identification of the particular anthocyanin(s) can be accomplished by methods know to those skilled in the art and include $^1$H NMR, chemical degradation, chromatography and spectroscopy, especially homo- and heteronuclear two-dimensional NMR techniques for the characterization of the isolated anthocyanin compounds.

The term "purified" or "isolated" is used in reference to the purification and/or isolation of one or more anthocyanins from an anthocyanin extract as described above. Again using conventional methods known in the art, various components of the anthocyanin extract can be separated into purified materials. In one aspect of the invention, the anthocyanin(s) of the extract are substantially purified and isolated by techniques known in the art. The purity of the purified compounds is generally at least about 90%, preferably at least about 95%, and most preferably at least about 99% and even more preferably at least about 99.9% (e.g. about 100%) by weight.

In accordance with the present invention, the anthocyanin extract contains one or more anthocyanins and/or anthocyanidins selected from the group consisting of peonidin, cyanidin, pelargonidin, delphinldin, petunidin, malvidin, apigenindin, auratinidin, capensinidin, europinidin, hirsutidin, 6-hydroxycyanidin, luteolinidin, 5-methylcyanidin, pulchellidin, rosinidin, tricetnidin, derivatives and mixtures thereof. In one embodiment, the anthocyanins and anthocyanidins are selected from the group consisting of cyanidin, peonidin, malvidin, petunidin, delphinidin, their glycoside derivatives, and mixtures thereof. In yet another embodiment, the extract contains at least one cyanidin-based anthocyanin.

Anthocyanins that can be useful in the inventions described herein include, but are not limited to, cyanidin-3-glucoside; cyanidin 3-glucosylrutinoside; cyanidin-3-gentibioside; cyanidin-3-rutinoside, cyanidin-3-sambunigrin, cyanidin-3-samb-5-glucoside, cyanidin-3-galactoside, peonidin-3-rutinoside, peonidin-3-glucoside, peonidin-3-galactoside, peonidin, cyanidin, cyanidin-3 sophoroside, pelargonidin, delphinidin, delphinidin-3-glucoside, delphinidin-3-galactoside, petunidin, petunidin-3-glucoside, petunidin-3-galactoside, malvidin, malvidin-3-arabinoside, malvidin-3-glucoside, malvidin-3-galactoside, kaempferol, hesperidin, gentiodelphin, platyconin, cinerarin and the like.

Suitable examples of anthocyanins from various plants, include, but are not limited to *Acer macrophyllum*, Cyanidin derivative, *Acer platanoides,* Cyanidin 3-(2",3"-digalloyl-beta-glucopyranose (3%), Cyanidin 3-(2"-galloyl-beta-glucopyranose (37%), Cyanidin 3-beta-glucopyranoside (60%), Acerola, *Malpighia marginata,* Cyanidin-3-glucoside, Cyanidin-3-glucoside, *Ajuga reptans,* Cyanidin 3-(di-p-coumaroyl) sophoroside-5-glucoside, Apple, *Malus* spp, Cyanidin 3-galactoside, Cyanidin 3-galactoside, Cyanidin 3-arabinoside, Cyanidin 3-glucoside, Cyanidin 3arabinoside, Cyanidin 3-xyloside, Cyanidin 3glucoside, Cyanidin 3-xyloside, Apricot, *Prunus armeniaca,* Cyanidin-3-glucoside, Cyanidin-3glucoside, *Artic bramble, Rebus* spp, Avocado, *Persea* spp, Acylated cyanidin 3,5-diglucoside, Cyanidin 3-galactoside, Cyanidin 3-galactoside, Banana, *Musa acuminata, M balbisiana,* Barberry, *Berberis* spp., Cyanidin-glucoside, Cyanidin-glucoside, Barley, *Hordeum vulgare,* Cyanidin and cyaniding glycosides, Bean, *Pheseolus vulgaris* (several cultivars), Cyanidin 3-glucoside, Cyanidin 3-glucoside, Cyanidin 3,5-diglucoside, *Begonia semperflorens* cvs, Cyanidin derivative, Benibana-cha, *Camellia sinensis,* Cyanidin 3-O-beta-D galactoside, Cyanidin 3-O-beta-D-galactoside, *Bellis perennis,* 3 Cyanidin 3-derivatives, *Bletilla striata,* Acylated cyanidin 3,7,3'-triglucoside derivatives, Bilberry, *Vaccinium myrtillus,* Artemis/Iprona; Indena, Cyanidin-3-galactoside (22%); Cyanidin-3-galactoside, Cyanidin-3-glucoside (9%), Cyanidin-3glucoside, Black beans, *Phaseolus,* Cyanidin-3-glucoside (96%), Cyanidin-3glucoside, Blackberry (European and American), *Moriferi veri, Rubus caesius, R. Alleghniensis, R. argufus, R. cuneifolius, R. setosus, R. trivials,* Cyanidin-glucoside (70-100%), Cyanidin-glucoside, Cyanidin-rutinoside, Black grapes, Many varieties, Black potatoes, *Solanumtuberosum tuberosum,* Cyanidin-glycosides, Black raspberry, *Rubus occidentalis,* Cyanidin-sambubloside (20%); Cyanidin-sambubloside, Cyanidin-xylosylrutinoside (40%); Cyanidin-glucoside, Cyanidin-glucoside, (17%), Cyanidin-rutinoside (23%), Black soybeans, Glycine max, Cyanidin-3-glucoside (96%), Cyanidin-3-glucoside, Blueberries, Five common *Vaccinium* spp, Cyanidin-glucoside (3%); Cyanidin-glucoside, Cyanidin-galactoside (3%), Cyanidin galactoside, Cyanidin-arabinoside (3%), Cyanidin-3-arabinoside, Bog whortleberry, *Vaccinium uliginosum,* Cyanidin-3-glucoside (14%), Cyanidin 3 glucoside (14%), Cyanidin #arabinoside (10%), Cyanidin-3-arabinoside (10%), Cyanidin 3-galactoside (6.5%), Cyanidin-3-galactoside (6.5%), Boysenberry, new Zealand, Cyanidin-3-sophoroside (44.5%), Cyanidin-3-glucoside, Cyanidin-3-glucoside (26.4%), Cyanidin-3 glycosylrutinoside (25.8%), Cyanidin-rutinoside (3.3%), Buckwheat, *Fagopyrum* species, Cyanidin-3-glucoside, Cyanidin-3-glucoside, Cyanidin 3-galactoside, Cyanidin-3-galactoside, Cacao, *Theobroma cacao,* Cyanidin 3-glucoside (suspected), Cyanidin-3-glucoside (suspected), Celery, *Apium* spp, Cherry laurel, *Prunus laurocerasus,* Cyanidin-3-arabinoside, Cyanidin-3-arabinoside, Chicory, *Cichorium intybus,* Cyanidin 3-glucoside, Cyanidin 3-glucoside, Chive, *Allium schoenoprasum,* Cyanidin-3-glucoside, Cyanidin-3-glucoside, Cyanidin-3-acetylglucoside, Cyanidin 3-(6 malonylglucoside), Cyanidin 3-(3,6 dimalonylglucoside), Chokeberry, *Aronia melanocarpa,* Artemis/Iprona, Cyanidin-3-galactoside (64.5%), Cyanidin-3-galactoside, Cyanidin-3-arabinoside (28.9%), Cyanidin-3 arabinoside, Cyanidin-3-glucoside (2.4%), Cyanidin-3 glucoside, Cyanidin-3-xyloside (4.2%), Cyanidin-3-xyloside, Coffee, *Coffea arabica* cv. *Bourbon Vermelho,* Cyanadin-3-glycoside, Cyanadin 3,5-diglyeoside, Cyanadin 3-glycoside, *Cotoneaster, Cotoneaster Medic.* Spp, Cyanidin 3-glucoside, Cyanidin 3-glucoside, Cyanidin 3-galactoside, Cyanidin 3-rutinoside, Cyanidin 3 galactoside, Cowberry or Lingonberry, *V. vitisidaea,* Cyanidin 3-galactoside Cyanidin 3-arabinoside, Cyanidin 3-galactoside, Cyanidin 3-glucoside, Cyanidin 3 arabinoside, Cyanidin 3 glucoside, *Chimonanthus praecox,* Cyanidin 3-O-glucoside, Cyanidin-3-O-glucoside, Acylated cyanidin 3-0-glucoside, Cyanidin glycoside, Cranberry (American and European), *Vaccinium macrocorpon,* Ocean Spray, Cyanidin-galactoside (16-24%), Cyanidin-galactoside, *V. oxycoccus,* Cyanidin-arabinoside (13-25%), Cyanidin arabinoside, CrOwberry, *Empetrum nigrum,* Cyanidin 3-glucoside Cyanidin 3,5-diglucoside, Cyanidin 3-glucoside, Cyanidin 3-rutinoside, Cyanidin 3-sophoroside, Chrysanthemum, *Dendranthema Grandiflorum,* Cyanidin 3-O-(6'-O-malonyl-beta-glucopyranoside, Currant (red and black), *Ribes rubrum, R. nigrum,* Cyanidin-glucoside (2-10%), Cyanidin-glucoside, Cyanidin sambubioside, Cyanidin-rutinoside (8-17%), Cyanidin-sambubioside (9-31%), Cyanidin-sophoroside (4-9%), Cyanidin xylosylrutinoside (28-73%), Cyanidin glucosylrutinoside (14-28%), *Cyneinonurn coccineum,* Cyanidin 3-O-glucoside (92%), Cyanidin 3-O-glucoside (92%), Cyanadin 3-O-(6-O rhamnosylglucoside (8%), Danewort, *Sambucus ebulus,* Cyanidin 3-xylosylglucoside, Cyanidin 3-sambubioside, Cyanidin 3 sambubloside, Cyanidin 3-glucoside, Cyanidin 3-sambubioside-5-glucoside, Cyanidin 3,5 diglucoside, Cyanidin 3-glucoside, Cyanidin 3-arabinoglucoside, *Dendrobium, Phalaenapsis* spp, Cyanidin derivatives, Dwarf dogwood, *Comus suecica,* Cyanidin 3-glucoside (4%), Cyannidin 3-glucoside (4%), Cyanidin 3-galactoside (16%), 2 Cyanidin derivatives (80%), *Echinacea, Echinacea* spp., Eldenberry, *Sambucus nigra,* Artemis/Iprona, Cyanidin-3-glucoside (42%), Cyanidin-3-glucoside, Cyanidin-3-sambubioside (43%) Cyanidin-3,5-diglucoside (2%), Cyanidin-3 sambubloside-5 glucoside (9%), *Gentians* spp, Cyanidin 3-O-beta-D-glucoside and 3 other derivatives, Cyanidin 3-O-beta-D-glucoside, *Fatsia japonica,* Cyanidin 3-lathyroside, Feijoa, *Feijoa sellowiana,* Cyanidin 3-glucoside, Cyanidin 3-glucoside, Fig, *Ficus carica* spp, Cyanidin 3-rhamnoglucoside, Cyanidin 3,5-diglucoside, Cyanidin 3-glucoside, Forsythia X, *intermedia* cv, Spring Glory, Cyanidin derivatives, Garlic, *Allium sativum,* Cyanidin 3-glucoside, Cyanidin 3-glucoside, Cyanidin 3-glucoside, Cyanidin 3-glucoside monoacylated, Cyanidin 3-glucoside triacylated, Ginseng, *Panax ginseng, Panax quinquefolius,* Cyanidin 3-O-β-D-xylopyranyl-(12)-β-D-glucopyranoside, Globe artichoke, *Cynara scolymus,* Cyanidin 3-caffeylglucoside, Cyanidin 3-caffeylsophoroside, Cyanidin 3-dicaffeylsophoroside, Gooseberry, *Ribes* spp, Cyanidin 3-glucoside, Cyanidin 3-glucoside, Cyanidin 3-rutinoside, Grape, *Vinis vinifera,* Cyanidin 3-monoglucoside, Cyanidin 3-monoglucoside, Cyanidin 3-monoglucoside-acetate, Cyanidin 3-monoglucoside-p-coumarate, Guava, *Psidium guajavica,* Cyanidin 3-glucoside, Cyanidin 3-glucoside, Hawthorn, *Crataegus* spp, Cyanidin 3-galactoside, Cyanidin 3-galactoside, Cyanidin 3-arabinoside, Cyanidin 3-glucoside, Cyanidin 3 glucoside, *Hibiscus* or *Roselle, Hibiscus sabdariffa,* Cyanidin-sambubioside (30%), Hollyhock, *Althaea rosea,* Cyanidin 3-glucoside, Cyanidin 3-rutinoside, Cyanidin 3-glucoside, Other cyaniding glucosides, Honeysuckle, *Lonicera nitida,* Cyanidin 3-rutinoside, Cyanidin 3-glucoside, Cyanidin 3-glucoside, Japanese garden iris, *Iris ensata,* Cyanidin 3RG, Cyanidin 3RG5G, Cyanidin 3Rgac5G, *Ipornoea purpurea,* Six acylated cyanidin 3-sophoroside-5 glucosides, Java plum, *Mytciana jaboticaba,* Cyanidin 3-glucoside, Cyanidin 3-glucoside, Jerusalem artichoke, *Helianthus tuberosus, Kokum, Garcinia indica,* Cyanidin 3-glucoside, Cyanidin 3-glucoside, Cyanidin 3-sambubioside, Cyanidin 3-sambubioside, *Laelioeattleya* cv Mini purple, Acylated cyaniding derivatives, *Lactuca saliva,* Cyanidin 3-O-(6"-malonylglucoside), Loganberry, *Rubus loganbaccus,* Cyanidin-sophoroside (48.1%), Cyanidin-glucoside, Cyanidin-glucoside (21.6%), Cyanidin-rutinoside (6.2%), Lupine, *Lupinus* spp, Cyanidin glycosides, presence confirmed, Lychee, *Litchi chinensis,* Cyanidin 3-glucoside, Cyanidin 3-glucoside, Cyanidin 3-galactoside, Cyanidin 3-rutinoside, Cyanidin 3 galactoside, Maize, *Zea mays*, Cyanidin 3-glucoside, Cyanidin 3-glucoside, Cyanidin 3-(6"-malonylglucoside) Cyanidin 3(3",6"dimalonyl-glucoside) Mango, *Mangifera indica*, (Cyanidin glycosides, Mangosteen, *Garcina mangostana*, Cyanidin 3-sophoroside, Cyanidin 3-glucoside, Cyanidin 3-glucoside, Maqul, *Aristotella chilensis*, Cyanidin 3-,5-diglucoside, *Matthiola incana*, Four acylated cyaniding 3-sambubloside-5 glucosides, Millet, *Pernnisetum americanum*, Cyanidin 3-glucoside, Cyanidin 3-glucoside, Mountain ash berry, *Sorbus* spp, Cyanidin 3-galactoside, Cyanidin 3,5-diglucoside Cyanidin 3-β-D glucopyranoside, Mulberry, *Moms nigra*, Cyanidin 3-glucoside, Cyanidin 3-glucoside, Cyanidin 3,5-diglucoside, Cyanidin 3-rutinoside, Cyanidin 3-sophoroside, Myrtle berry, *Myrtus communis*, Cyanidin 3-glucosides, Cyanidin 3-glucosides, Cyanidin 3-diglucosides, Olive, *Olea europaea*, Cyanidin 3-rutinoside, Cyanidin 3-glucoside, Cyanidin 3-glucoside, *Cyanidin derivatives*, Onion, *Allium sepa*, Cyanidin 3-glucoside, Cyanidin 3-glucoside, Cyanidin 3-diglucoside, Cyanidin 3-laminarioside, Orange, *Citrus sinensis*, Cyanidin 3-glucoside (95%), Cyanidin 3-glucoside, Cyanidin 3,5-diglucoside, Passion fruit, *Pasiflora edulis*, Cyanidin 3-glucoside, Cyanidin 3-glucoside, Pea, *Pisum sativurn*, Cyanidin 3-sophoroside glucosides, Cyanidin 3-sambubioside-5-glucosides, Peach, *Prunus persica*, Cyanidin 3-glucoside, Cyanidin 3-glucoside, Cyanidin 3-rutinoside, Cyanidin derivatives, Peanut, *Arachis hypogaea*, Cyanidin glucosides, Pear, *Pyrus communis*, Cyanidin 3-galactoside, Cyanidin 3-galactoside, Cyanidin 3-arabinoside, Cyanidin 3-arabinoside, *Perilla, Perilla frutescens*, Cyanidin 3,5-diglucoside, Cyanidin 3,5-derivatives, *Petunia* spp, Cyanidin 3-rutinoside, *Phalsa, Grewia* spp, Cyanidin 3-glucoside, Cyanidin 3-glucoside, Pineapple, *Anans comosus*, Cyanidin 3-galactoside, Cyanidin 3-galactoside, Pistachio, *Pistacia vera, Pragmites australis*, Cyanidin-3 derivatives, Plum, 2000 varieties, 15 species, Cyanidin-glucoside (37%), Cyanidin glucoside, Cyanidin-rutinoside (45%), Pomegranate, *Punica granatam*, Cyanidin-glucoside (30%), Cyanidin-glucoside, Cyanidin-diglucoside (17%), Purple carrot, *Daucus carota*, Cyanidin-glucoside, Cyanidin-glucoside, Cyanidin-glucosylgalactoside, Cyanidin-galactoside, Cyanidin-digalactoside, Cyanidin-galactoside, Quince, *Cydonia oblonga*, Cyanidin-3 glucoside, Cyanidin 3,5-diglucoside, Cyanidin derivatives, Radish, *Raphanus sativus*, Acylated cyanidin 3-sophoroside-5-glucoside, Acylated cyanidin 3 diglucoside-5-glucoside, Red cabbage, *Brassica oleracea* var *capitata*, Cyanidin glycosides, Reed, *Phalaris arundinacea*, Cyanidin 3-glucoside, Cyanidin 3-glucoside, Cyanidin 3-(6"-,malonylglucoside), Cyanidin 3 (3",6"dimalonyl-glucoside), Red onion, *Allium cepa*, Cyanidin 3-glucoside, Cyanidin 3-glucoside, Acylated cyanidin 3-glucoside derivatives, Red petunia, *Petunia* spp, Cyanidin 3-glucoside, Cyanidin 3-glucoside, Cyanidin 3-sophoroside, Red raspberry, *Rubus idaeus*, Cyanidin glucoside (17%), Cyanidin-glucoside, Cyanidin-rutinoside (7%), Cyanidin-sophoroside (50%), Cyanidin glycosylrutinoside (26%), Cyanidin-diglucoside, Rhubarb, *Rneum* spp, Cyanidin 3-glucoside, Cyanidin 3-glucoside, Cyanidin 3-rutinoside, Rice, *Oryza* spp, Cyanidin 3-glucoside, Cyanidin 3-glucoside, Cyanidin 3-rhamnoside, Cyanidin 3,5-diglucoside, Rosehip, *Rosa canina*, Cyanidin 3-rutinoside, Cyanidin 3-glucoside, Cyanidin 3-glucoside, Cyanidin 3,5-diglucoside, Rye, *Secale cereale*, Cyanidin 3-glucoside, Cyanidin 3-glucoside, Cyanidin 3-rhamnosylglucoside, Cyanidin 3-rhamnosyldiglucoside, Cyanidin 3-rutinoside, Cyanidin 3-rutinoside derivatives, Cyanidin 3-gentiobioside, Sheepberry, *Viburnum* spp, Cyanidin 3-glucoside, Cyanidin 3-glucoside, Cyanidin 3-arabinosylsambubioside, *Sorghum, Sorghum bicolor*, Cyanidin, Cyanidin glycosides, Sparkleberry, *V. arboreum*, Cyanidin 3-glucoside, Cyanidin 3-glucoside, Cyanidin 3-arabinoside, Cyanidin 3-galactoside, Strawberry, *Fragaria ananassa*, Cyanidin-glucoside (minor), Cyanidin-glucoside, Sunflower, *Hellanthus annuus*, Cyanidin 3-glucoside, Cyanidin 3-glucoside, Acylated cyanidin 3-glucoside, Cyanidin 3-xyloside, Cyanidin 3-xyloside, Acylated cyanidin 3-xyloside, Cyanidin 3-vanillyl sambubioside, Sweet cherry, *Prunus avintn*, Cyanidin-glucoside, Cyanidin-glucoside, Cyanidin-rutinoside; Cyanidin 3-suphoroside, Sweet potato, *Ipornoea batatas Sophronitis coccinea*, Cyanidin derivatives, Five acylated cyanidin 3,3',7-triglucosides, Tamarillo or tomato tree, *Cyphomandrea betacea*, Cyanidin 3-rutinoside, Cyanidin 3-glucoside, Cyanidin 3-glucoside, Tamarind, *Tamarindus indica*, Cyanidin 3-glucoside, Cyanidin 3-glucoside, Taro, *Colocasia esculenta*, Cyanidin 3-glucoside, Cyanidin 3-glucoside, Cyanidin 3-rutinoside, Tart Cherry (balaton), *Prunus cerasus* cv. Balaton, Nutrilite, Cyanidin-3-rutinoside-hexose (75%), Cyanidin-3-rutinoside-pentose (3%), Cyanidin-3-rutinoside (18%), Tart cherry (montmorency), *Prunus cerasus* cv. Montmorency, Nutrilite, Cyanidin-3-sophoroside (80%), Cyanidin-3-glucoside (20%), Cyanidin-3-glucoside (20%), Tulip, *Tulipa* spp, Cyanidin 3-O-(6"-rhamnosylglucosides), Cyanidin 3-O-derivative, Turnip, *brissica rapa*, Cyanidin 3-glucoside, Cyanidin 3-glucoside, Cyanidin 3-diglucoside-5-glucoside, Water lily, *Nymphasa alba*, Cyanidin 3-O-(6"-acetyl-beta-galactopyrosinase (23%), Cyanidin 3-O-galactoside (2%), Cyanidin 3-O-galactoside (2%), *Weigela* spp, Cyanidin 3-O-glucoside, Cyanidin 3-O-glucoside, Cyanidin 3-O-glucoside xylose, Wheat, *Triticum* spp, Cyanidin 3-glucoside, Cyanidin 3-glucoside, Acylated cyanidin glucoside, Cyanidin 3-rutinoside, Acylated cyanidin 3-rutinoside, Cyanidin 3-gentiobioside, Wild rice, *Zizania aquatica*, Cyanidin 3-glucoside, Cyanidin 3-glucoside, Cyanidin 3-rhamnoglucoside, and Yam, *Dioscoracea* spp, Cyanidin 3,5-diglucoside, Cyanidin 3-glucoside, Cyanidin 3-glucoside, Cyanidin 3-rhamnoglucoside, Cyanidin 3-gentiobioside, Acylated cyanidin glucosides.

The term "anthocyanin" as used herein is intended to refer not only to monomeric anthocyanins, but also refers to dimeric and polymeric (i.e. containing from 3 to 20 anthocyanidin monomer residues) forms of anthocyanins and to leucoanthocyanidins (also known as flavan-3,4-diols). The anthocyanins can comprise substitutions (e.g. alkyl, alkoxy groups etc.) and in particular can be O-glycosylated, as described above.

The anthocyanin in the composition can be a single anthocyanin, or comprise a mixture of anthocyanins. In particular, the anthocyanin is selected from the group consisting of: malvidin, cyanidin, delphinidin, paeonidin, pelargonidin and petunidin, and glycosides thereof A typical example is malvin (malvidin diglucoside) chloride, which is commercially available in a purified form. Alternatively the anthocyanin can be obtained by extracting anthocyanin containing plants such as grape, black carrot, red cabbage, blackberry, blackcurrent, cranberry and the like as described above.

The phrase "stabilized anthocyanin composition" as used herein is intended to mean that the anthocyanin, either as a glycoside (anthocyanoside) or as an aglycon (anthocyanidin), for example, at about 37° C., pH=about 7.0, remains at least about 50% undegraded from the original percentage of anthocyanin for at least about 3.5 hours. Likewise, the phrase includes pH values of about 4, about 5, about 6 and about 8 with similar stability.

The term "stabilizing compound" as used herein is intended to include those compounds that have at least one —SH group. Not to be limited by theory, it is believed that an interaction occurs between the thiol group and the anthocyanin such that the thiol containing group is oxidized (often to a disulfide, —S—S—) and the anthocyanin receives a hydrogen atom, which is then later liberated.

Suitable examples of stabilizing compounds include yeast extract (e.g., beer yeast), dihydrolipoic acid, salts of dihydrolipoic acid such as amino acid salts, cysteine, derivatives of cysteine, such as N-acetylcysteine, glutathione, salts of glutathione, SH-proteinase such as papain, bromelain, ficin, ehymopapain and mixtures thereof, SH-metalloproteinases, peptides containing cysteine, peptides containing glutathioine, fermented oyster extract, fermented bean curd, thiolated chitosans, thiolated gelatins or mixtures thereof.

In one aspect, the mole ratio of stabilizing compound to anthocyanin is between about 0.1 to about 10, more particularly between about 0.5 to about 5 and even more particularly about 1 to about 1.

Not to be limited by theory the following is an explanation of the surprising an unique findings with regard to the present invention. Anthocyanosides are susceptible to pH-shifts by forming colorless derivatives. The flavylium-cation and the quinonoidal-base are colored and the equilibria are not generally influenced with the presence of both species being pH-dependent [pH-value <2]. (See Scheme 1) It is believed that this equilibrium is established very quickly and that the reaction is reversible. The "attack" of the water under appropriate conditions yields a series of colorless derivatives (carbinolbase, chalcone). This part of the reaction progresses slowly is and not normally reversible. The decolouration process begins at pH-values of about >3.5. Prevention of the water attack by molecular protection provides stabilization of anthocyanosides as described throughout the specification.

more likely is the effect of self-association. Self-association occurs at concentrations of about >0.0001 molar solution concentration. Self association may help mask the protective effects of thiol-compounds; hence the protective effects were tested at various concentrations.

Based on theory, co-pigmentation should yield a bathochromic ($\lambda$ max shift towards higher wave length) and a hyperchromic (increase in absorption at $\lambda$ max at the same concentration) shift.

Figure 2:
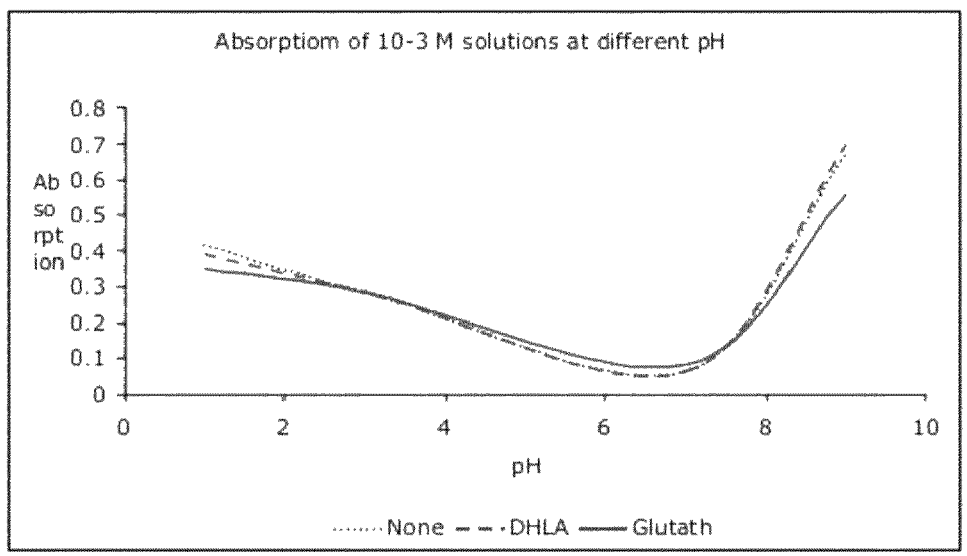
FIG. 2 provides evidence of a lack of hyperchromic shift for cy-3-O-glucoside in a 1 mMolar solution of glutathione or DHLA.

The present studies based on UV-spectroscopy found that neither DHLA (dihydrolipoic acid) nor GSH (glutathione) yielded a bathochromic or a hyperchromic effect as shown in FIGS. 1 and 2. Therefore, increase in stability is most likely related to another mechanism.

The spectral properties of freshly dissolved cyanidin-3-O-glucosides (protected and unprotected) in terms of $\lambda$ max shifts for different pH-values were identical as shown in FIGS. 1 and 2.

The stability of bilberry extract (various concentrations, molar concentrations expressed as cyanidin-3-O-glucoside) was investigated in presence/absence of GSH or DHLA by UV-spectroscopy measuring the absorption at the pH-dependent $\lambda$ max.

Figure 3:
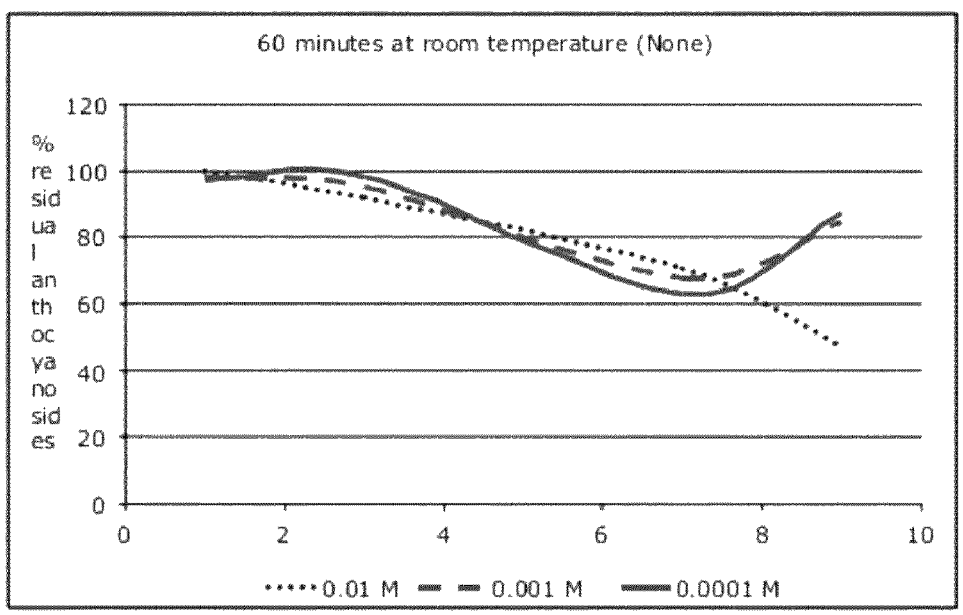
FIG. 3 provides percent residual anthocyanosides of bilberry extract (unprotected).
Figure 4:
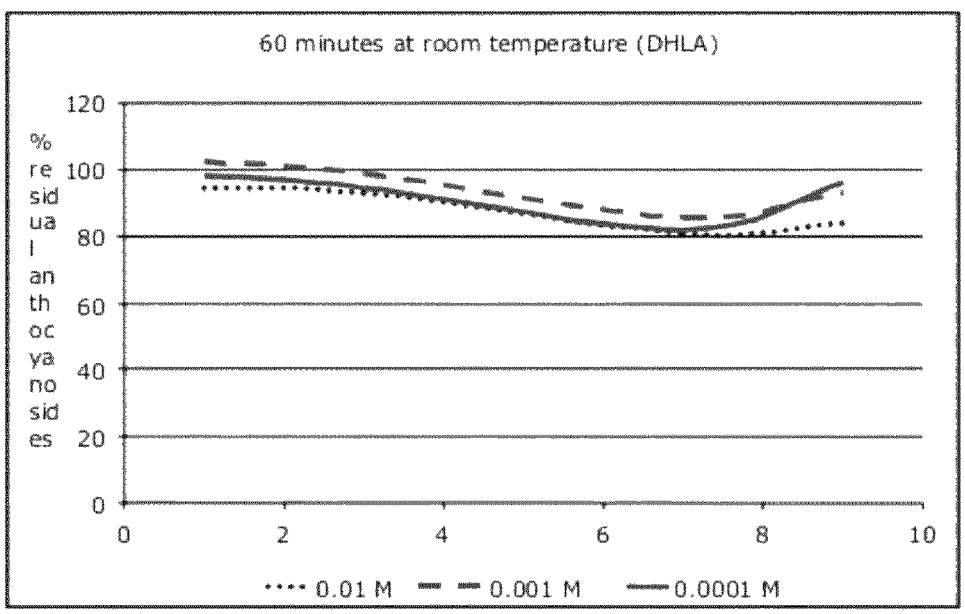
FIG. 4 provides percent residual anthocyanosides of bilberry extract that is DHLA protected in contrast to unprotected seen in FIG. 3.

As noted in FIGS. 3, 4 and 5, the present investigations showed that anthocyanosides are protected against degradation by GSH (0.65 mmolar) and DHLA (1.44 mmolar) at all concentrations tested, especially at pH values >5-6. The $\lambda$ max at the various pH tested did not differ between the unpro-

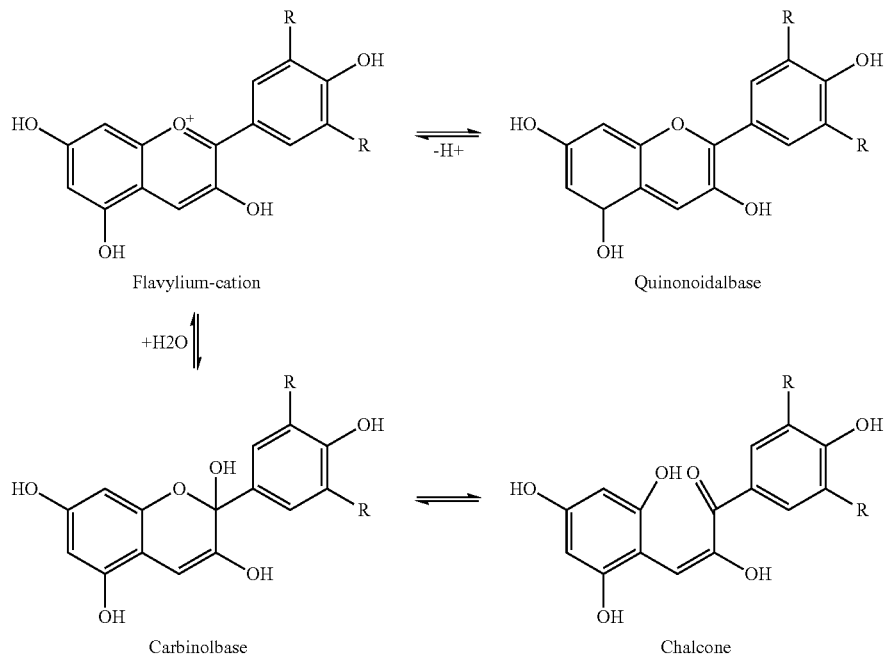

Scheme 1

Based on theory, known phenomenon of co-pigmentation (describing increased stability of anthocyanosides in presence of "copigments") yields a bathochromic ($\lambda$, max shift towards higher wave length) and a hyperchromic (increase in absorption at $\lambda$ max for the same concentrations) effect. Hence, clarification of whether thiol-compounds were able to act as co-pigments was undertaken.

Based on theory, anthocyanosides are able to increase their stability by self-association. The higher the concentration, the tected and the protected solutions. Since it was observed that with cyanidin-glucoside no hyperchromic effect occurred, the stabilizing effect of thiol-containing protection agents is considered to be different from co-pigmentation.

The stability of bilberry extract at a 0.0001 molar concentration (expressed as cyanidin-3-O-glucoside) was investigated by UV-spectroscopy at different pH-values over time in absence/presence of DHLA (1.44 mmolar solution).

These experiments shown in FIGS. 6A through 6D, demonstrate that DHLA protects anthocyanosides at those pH-values where unprotected anthocyanosides degrade quickly (pH >5-6). Most interestingly, when fitting the data to statistical models (regression analysis) unprotected degradation kinetics fits to linear regression whereas DHLA protected degradation kinetics fits to exponential regression analysis. That points to a protection mechanism which builds up over time.

The degradation kinetics of selected anthocyanosides from bilberry extract (0.48 mmolar solution) was investigated over time by HPLC after incubation at pH=7 and 25° C. in presence/absence of GSH (0.65 mmolar solution).

Figure 8:
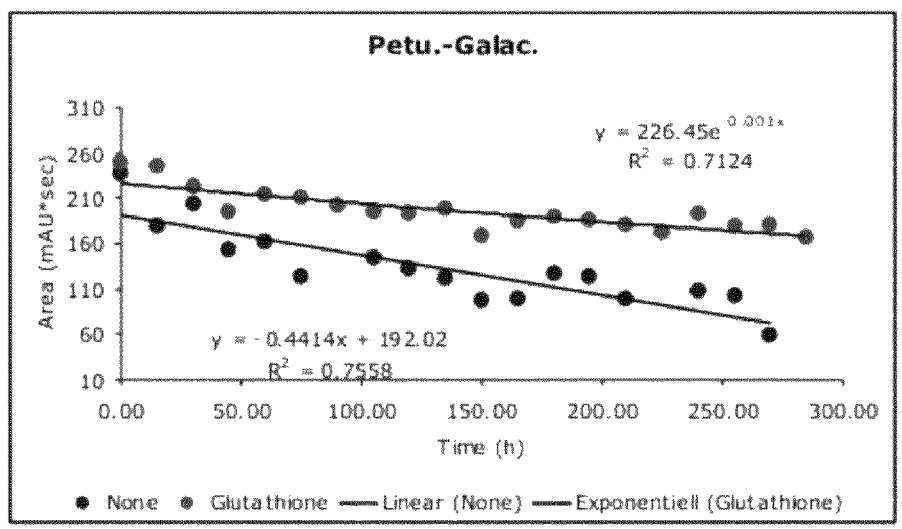
FIG. 8 provides comparative degradation kinetics of petunidin-3-O-galactoside that is unprotected or protected with glutathione.
Figure 9:
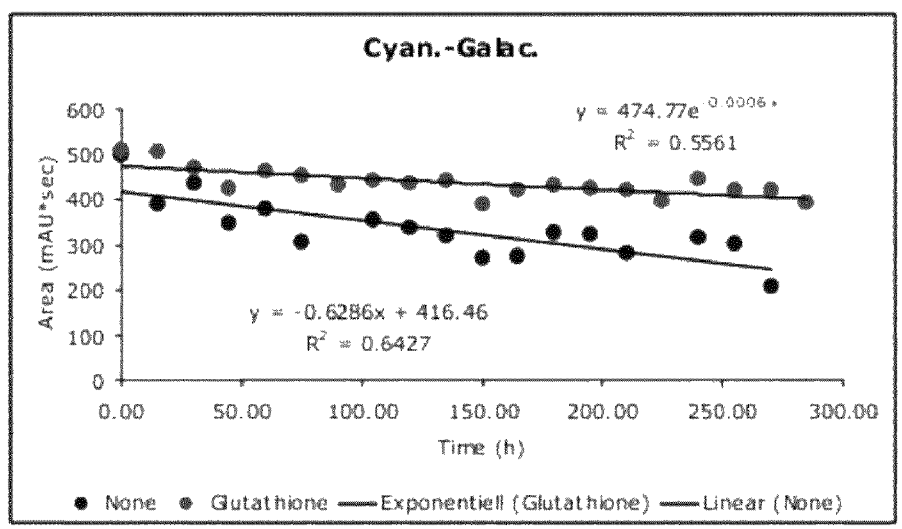
FIG. 9 provides comparative degradation kinetics of delphinidin-3-O-galactoside that is unprotected or protected with glutathione.

At selected time points the peak area of Delphinidin-3-O-galactoside (very susceptible to degradation), Petunidin-3-O-galactoside (medium susceptibility) and Cyanidin-3-O-galactoside (rather stable) was checked by HPLC (See FIGS. 7, 8 and 9). Stabilizing properties were observed in presence of GSH, again better fitted by exponential regression analysis. It is therefore reasonable to conclude that the protection mechanism is different from co-pigmentation and involves a mechanism where the protective effect is built up over time.

Cyanidn-3-O-Galactoside (0.001 molar solution) was dissolved at pH=3.1 or pH=7.0 each with/without DHLA (1.44 mmolar solution). Replicate incubations were followed at 25° C. over 3 days by HPLC.

Figure 10:
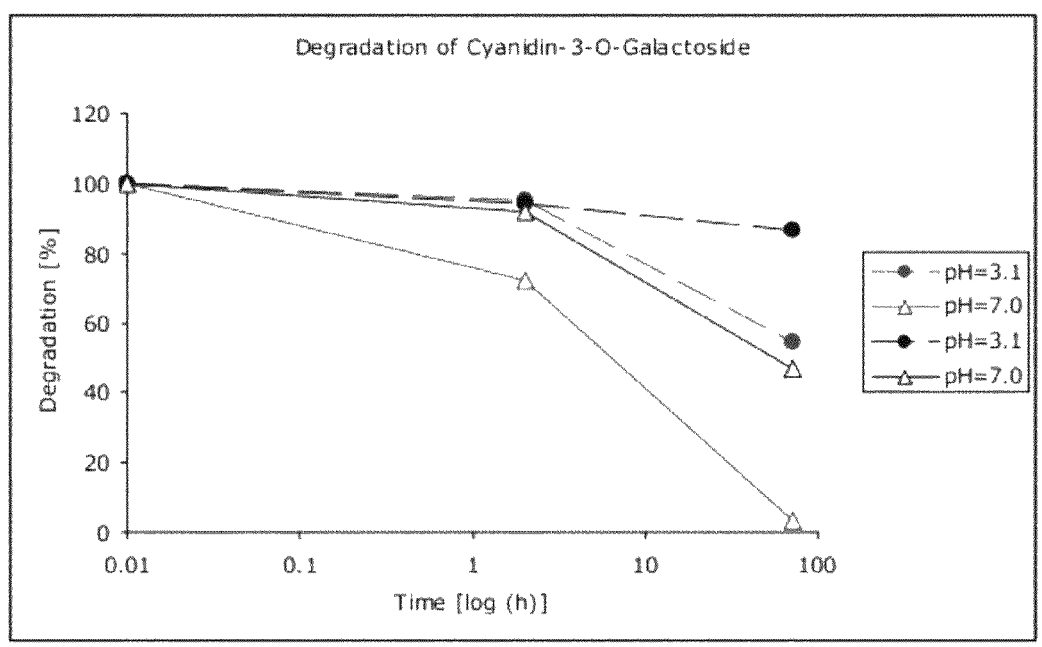
FIG. 10 provides comparative degradation kinetics of cyanidin-3-O-galactoside at two pH values with and without protection with glutathione.

As seen in FIG. 10, the effect of DHLA is surprisingly long-lasting. After 3 days at pH=7.0 at 25° C. about 47% of Cyanidn-3-O-Galactoside was recovered in presence of DHLA, whereas the unprotected sample yielded almost 0% of cyanidin-3-O-galactoside. Comparative figures for pH=3.1 were 95% and 61%, respectively.

Figure 11:
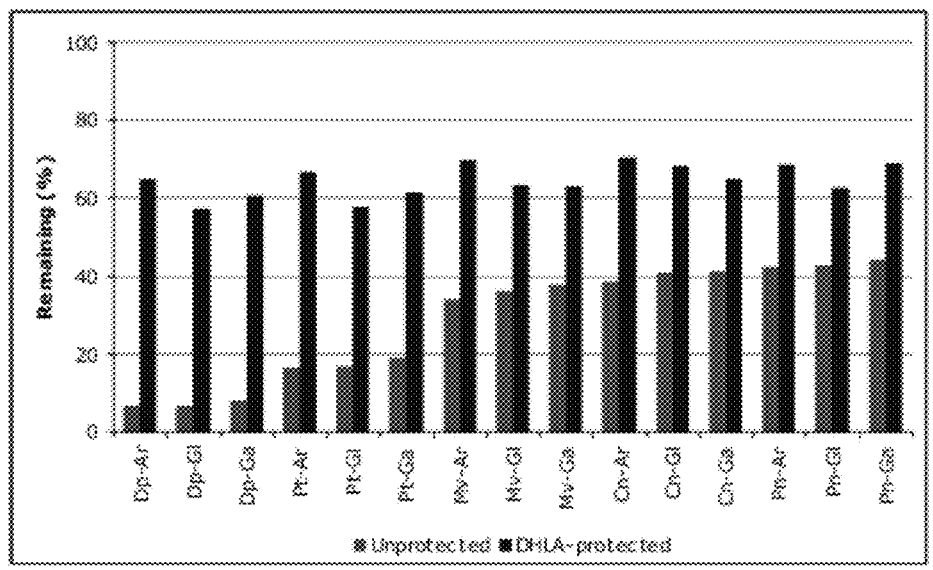
FIG. 11 provides comparative degradation of 15 bilberry anthocyanosides that are DHLA protected.
Figure 12:
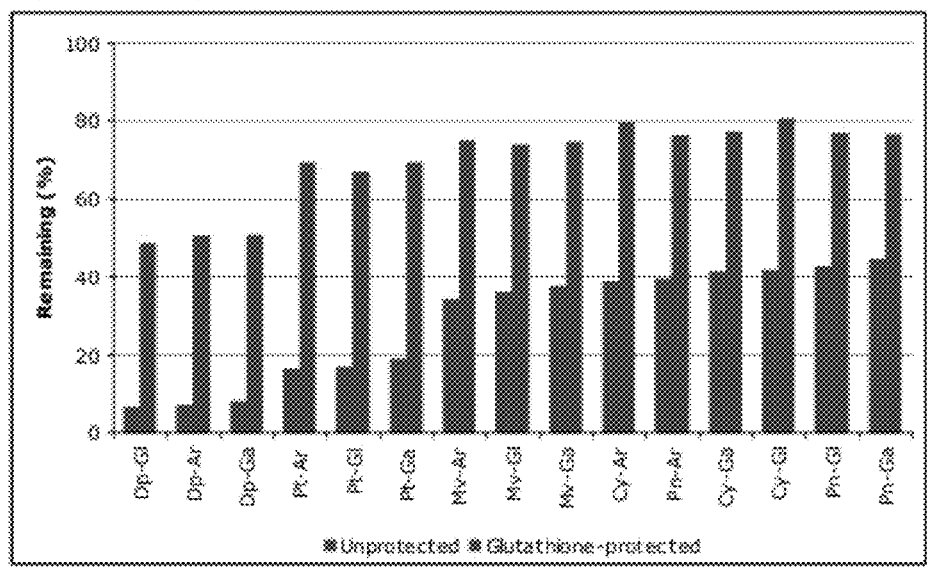
FIG. 12 provides comparative degradation of 15 bilberry anthocyanosides that are glutathione (GSH) protected.

The degradation kinetics of anthocyanosides from bilberry extract (0.48 mmolar solution) was investigated in presence/absence of protecting DHLA (FIG. 11) (1.44 mmolar solution) and GSH (0.65 mmolar solution) by HPLC (FIG. 12).

The focus of the evaluation was whether the basic anthocyanidin skeleton is involved with the protection effect to some degree. When looking at the results obtained, it seemed plausible that the protection effect of thiol-compounds was inversely correlated with the susceptibility of unprotected degradation. The more susceptible the anthocyanidin skeleton was, the better was the protective effect of GSH or DHLA. A slightly better absolute effect for GSH was been observed.

Substitution patterns of anthocyanidins present in bilberry extract are noted in the table which follows:

| Anthocyanidin | Substitution pattern (B-ring) |
|---|---|
| Delphinidin | 3',4',5' OH |
| Petunidin | 3'-OCH3, 4',5' OH |
| Malvidin | 3',5'-OCH3, 4' OH |
| Cyanidin | 3',4' OH |
| Peonidin | 3'-OCH3, 4' OH |

As noted in the table above, there is evidence for a structure related effect of (a) degradation and (b) for a protective mechanism. First, the number of substitutions about the anthocyanin plays a role, and, second, within the same number of substitutions the presence of methoxy-groups influences the stability.

The most susceptible anthocyanidin is delphinidin, bearing 3 hydroxyl-groups at the B-ring. The most stable is peonidin, bearing 1 hydroxyl-group and 1 methoxy-group (superior to 2 hydroxyl-groups as in cyaniding).

The proposed newly discovered mechanism is believe to be related to the stabilization of the flavylium cation at pH=7.0. All compounds tested do bear carboxylic acid groups and free thiol-groups.

Cysteine has two anchor points with anthocyanosides. First, there is a strong interaction of the thiol-portion (probably tightly associated with the anthocyanidin at position 4 or even to the sugar part) and, second, the carboxylic acid function protects the cationic part.

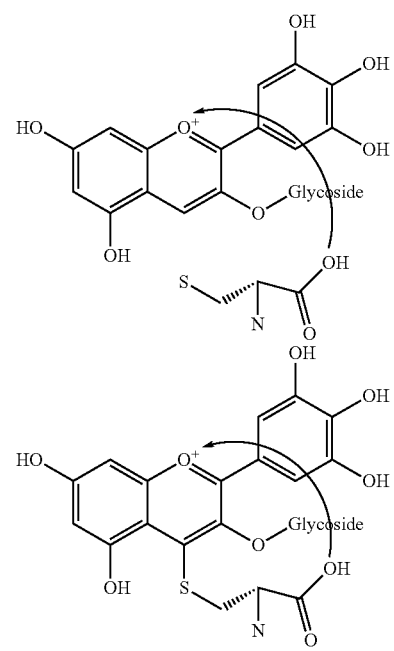

A similar mechanism is proposed for DHLA. The presence of thiol groups is believed to anchor DHLA to the anthocyanidin so that the carboxylic function can help protect the molecule. Possibly, an increased effect of DHLA compared to cysteine might be allocated to a more stable "association" of two thiol groups when compared to the single thiol found in cysteine.

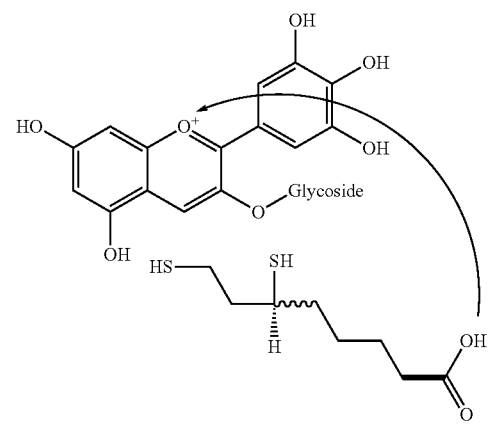

Similarly it is possible to draw the reaction with reduced glutathione. In this case, superior activity is obtained by two carboxylic acid functions instead of one.

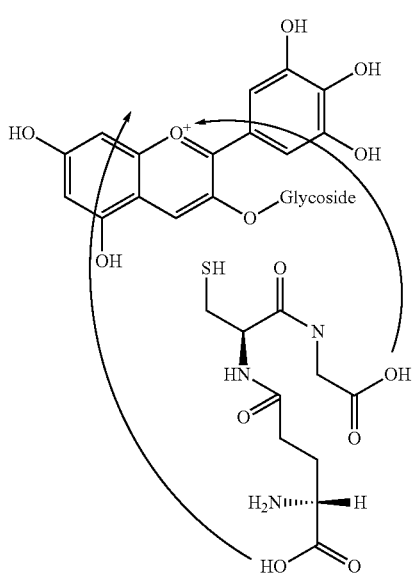

The mechanism is considered to be related to a reaction cascade of the flavylium cation while serving as radical scavenger.

The redox potential of 2R—SH/R—SS—R compounds tested is lower than that of anthocyanosides. For example 2GSH/GSSG=~−0.22 V whereas the redox potential A-OH/A=O=~0.20-0.75 V (see below).

Radical scavenging properties of anthocyanosides can explained by following reactions:

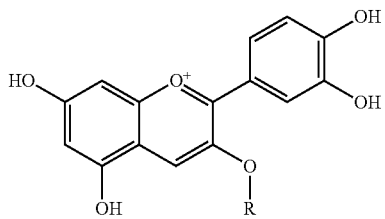

R=H Anthocyanidin, R=sugar Anthocyanoside

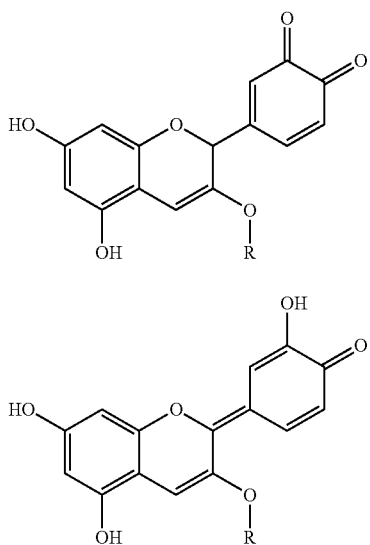

Quinone-/Semiquinone structure (colored products, examples).

The stability of these (semi)quinines is believed to be related to the substitution pattern, as the quinone structure requires a 4'-substitution. Once the quinone is formed, reversal of the reaction to the flavylium structure is less feasible. On the other hand, any substitution on 5'-position hinders the formation of the semiquinone.

That may explain why a 3'-OH and 4'-methoxy substituted structure appear to be most stable: It forms a semiquinone that cannot be attacked by water forming colorless products. Such a semiquinone may be more or less easily re-converted to the flavylium cation.

Anthocyanidins/Anthocyanosides (A-OH) are converted to semiquinones/quinones (A=O) by following reaction:

$$A\text{-}OH \rightarrow A=O + H^+ + e^-$$

R—SH compounds undergo following reactions:

Overall process: $2RSH \rightarrow R\text{—}SS\text{—}R + 2H^+ + 2e^-$

Detailed: $R\text{—}SH \rightarrow R\text{—}S^- + H^+ \rightarrow R\text{—}S° + e^- H^+$ $2R\text{—}S° \rightarrow R\text{—}SS\text{—}R$ (R—S° ... Radical)

Such a mechanism would point to a 1:1 consumption in a way that 2 molecules anthocyanosides are able to form 1 molecule R—SS—R from 2 molecules R—SH and are left as semiquinones. Alternatively 1 anthocyanoside molecule may form 1R—SS—R by being converted to the quinone.

If no alternative reactions are taking place, following reaction cascade is reasonable:

In a combination of R—SH and anthocyanosides at neutral pH, primarily R—SH is converted to R—S°.

Part of the R—S° is scavenged by anthocyanosides (A-OH) which are thereby converted to A=O semi-quinones, yielding again R—SH.

At pH=7, A=O is reconverted to A-OH by consumption of R—SH and will then eventually degrade gradually as known.

Suitable examples of stabilizing compounds include yeast extract, dihydrolipoic acid, salts of dihydrolipoic acid such as amino acid salts, cysteine, derivatives of cysteine, such as N-acetylcysteine, glutathione, salts of glutathione, SH-proteinase such as papain, bromelain, ficin, ehymopapain and mixtures thereof, SH-metalloproteinases, peptides containing cysteine, peptides containing glutathioine, fermented oyster extract, fermented bean curd, thiolated chitosans, thiolated gelatins or mixtures thereof.

In one aspect, the mole ratio of stabilizing compound to anthocyanin extract is between about 0.1 to about 10, more particularly between about 0.5 to about 5 and even more particularly about 1 to about 1.

In another aspect, the stabilized anthocyanin extract composition is stabile toward degradation when exposed to an aqueous environment with a pH of about 2, about 3, about 4, about 5, etc. through about 14, for example, a pH of 7 or greater.

In still another aspect, the stabilized anthocyanin extract is an anthocyanoside.

In still yet another aspect, the stabilized anthocyanin extract is an anthocyanidin.

In still other aspects of the invention, the stabilized anthocyanin extract includes one or more anthocyanosides that are glycosidses of perlargonidin, peonidin, cyanidin, malvidin, petunidin, delphinidin.

The present invention also pertains to methods of preparing the stabilized anthocyanin compositions described herein.

The present invention provides that the stabilizing compound(s) can be admixed with the anthocyanin containing plant material during the extraction and/or manufacturing process, thereby reducing or eliminating the oxidative destruction of the anthocyanin that commonly occurs upon processing and even upon storage. For example one or more of the stabilizing compounds in the ratios generally described herein can be added into the extraction medium (solvent) during the extraction process as disclosed in US Patent Publication 2002/0018821, published Feb. 14, 2002 by Chrystele Soulier et al., the contents of which are incorporated herein in their entirety.

Typically, the anthocyanin extract is mixed directly with the stabilizing compound. This can be accomplished by simply mixing, grinding, combining, etc. the two materials as solids or by dissolution in a solvent, such as water. Additional additives, such as carriers, vitamins, antioxidants, etc., as described herein below, can be added to the mixture by conventional methods.

In one embodiment, a red fruit extract containing anthocyanosides, is taken up in an aqueous solution and optionally treated with an —SH stabilizing compound as described herein. The aqueous extract is cooled until it reaches a homogeneous temperature of less than 15° C. The aqueous extract is filtered and is optionally treated with an —SH stabilizing compound as described herein, the permeate obtained is recovered and loaded onto a macrocrosslinked polymeric resin. The resin is then rinsed with demineralized water, optionally treated with an —SH stabilizing compound as described herein and then the resin obtained is eluted with an alcoholic eluting solution, which may optionally be treated with an —SH stabilizing compound as described herein. The eluate obtained is concentrated, optionally treated with an —SH stabilizing compound as described herein and then dried.

In another embodiment, the process of stabilization is carried out on an alcoholic red fruit extract obtained according to the following process. The pulp is first separated from the whole red fruit and the pulp is then brought into contact with an alcoholic extraction solution which can optionally contain an —SH stabilizing compound as described herein. The solid phase is separated from the liquid phase and the liquid phase can be optionally treated with an —SH stabilizing compound as described herein. The major portion of the residual alcohol contained in the liquid phase is evaporated under vacuum so as to obtain an alcoholic concentrate.

Advantageously, the solvent used for the alcoholic extraction is chosen from the group comprising methanol, ethanol, butanol and acetone.

In practice, the alcoholic extraction is carried out at room temperature in at least two successive steps, each lasting 20 minutes. The solvent is then evaporated off. In addition, it is also possible to carry out the extraction of the anthocyanosides not from the pulp alone, but from whole fruits.

According to the invention, the process of stabilization can be carried out starting with extracts of fruits which are commercially available or with prepurified anthocyanoside extract, each provided in liquid or powdered form. In this case, the fruit extract or the prepurified extract can then be taken up, before the purification step, either with alcohol, in particular methanol, or with water and treated with an —SH stabilizing compound as described herein.

In the process of purification of the invention, the cooling of the red fruit extract is advantageously carried out until the temperature of the extract is homogeneous and less than 10° C., in particular, less than 5° C., with the temperature being maintained for at least about twelve hours.

With regard to the step of filtration of the aqueous extract or alcoholic extract, it may be carried out on a cellulose filter or a stainless steel gauze with a cut-off of between 0 and 100 micrometers or equivalent.

In order to further increase the titer and the concentration of stabilized anthocyanosides in the final extract, the alcoholic solution with which the stabilized anthocyanosides are eluted from the resin is an aqueous solution of ethanol whose ethanol concentration is between 10 and 90%, advantageously close to 40%.

The stabilized eluate obtained is concentrated at a controlled temperature in the region of 30° C. and then freeze-dried or spray-dried so as to obtain a stabilized powder.

In one embodiment, for example, a concentrate of bilberry extract and L-cysteine hydrochloride are combined (9:1, w/w) and spray dried to afford a stabilized bilberry extract as a powder. In general, the bilberry extract to free cysteine ratio is approximately 10:1, w/w.

The present invention further pertains to methods of treatment of various ailments by administration of a therapeutically effective amount of the stabilized anthocyanin compositions described herein. Ailments include, the need for increased antioxidant capacity, arthrosclerosis, reduction of pain, inflammation. Reduction or the elimination of pain includes various forms of pain including arthritis, dysmenorrheal, headaches, joint pain, muscular pain, osteoarthritis, age-related macular degeneration (AMD), cataracts, retinopathy, and combinations thereof.

Therefore, the present invention further provides bioavailable stabilized anthocyanin compositions that are useful to treat various afflictions noted herein. The stabilized anthocyanin compositions can be administered by a number of methods, as discussed infra.

Surprisingly, the present invention provides that use of cysteine in combination with an anthocyanin composition (whether it be an anthocyanidine or an anthocyanoside) helps to increase the delivery of the anthocyanin to a subject in need thereof by at least twice the amount relative to a subject that ingests an anthocyanin composition without the presence of cysteine. It has been surprisingly found that plasma concentration levels of the anthocyanin where the anthocyanin is delivered in the presence of cysteine after 4 hours is at least twice the plasma concentration of an anthocyanin delivered without the cysteine. Therefore, the present invention provides a method to increase the amount of bioavailable anthocyanin in a subject by administering to the subject an effective amount of an anthocyanin and cysteine. The administration can be by any means, but oral delivery is generally preferred.

In one embodiment, the ratio of the anthocyanin to the cysteine is about 10 to about 0.1, more particularly between about 10 to about 0.5, and even more particularly between about 10 to about 1 on a weight basis. It is important to note that without the use of cysteine, the bioavailability of the anthocyanin is dramatically decreased as noted in the examples described herein.

The increased bioavailability an anthocyanin in the presence of cysteine is generally at least twice that the bioavailability of an anthocyanin alone after administration. Ideally, the bioavailability is increased by the inclusion of cysteine such that the bioavailability increases to 3, 4, 5, 10 and 20 times more than equivalent anthocyanins without the inclusion of cysteine. This is a surprising find.

The compositions of the invention can be incorporated into various foods, drinks, snacks, etc. In one aspect, the composition can be sprinkled onto a food product, prior to consumption. If sprinkled onto a food product, a suitable carrier such as starch, sucrose or lactose, can be used to help distribute the concentration of the stabilized anthocyanin composition making it easier to apply to the food product.

The compositions of the present invention can also be provided as supplements in various prepared food products. For the purposes of this application, prepared food product means any natural, processed, diet or non-diet food product to which a composition of the invention has been added. The compositions of the present invention can be directly incorporated into many prepared diet food products, including, but not limited to diet drinks, diet bars and prepared frozen meals. Furthermore, the compositions of the inventions can be incorporated into many prepared non-diet products, including, but not limited to candy, snack products such as chips, prepared meat products, milk, cheese, yogurt, sport bars, sport drinks, mayonnaise, salad dressing, bread and any other fat or oil containing foods. As used herein, the term "food product" refers to any substance fit for human or animal consumption.

The compositions of the invention can be added to various drinks, such as fruit juices, milkshakes, milk, etc.

The preferred method of administration is oral. The compositions of the invention can be formulated with suitable carriers such as starch, sucrose or lactose in tablets, capsules, solutions, syrups and emulsions. The tablet or capsule of the present invention can be coated with an enteric coating that dissolves at a pH of about 6.0 to 7.0. A suitable enteric coating, which dissolves in the small intestine but not in the stomach, is cellulose acetate phthalate.

Formulation of the compositions of the invention into a soft gel capsule can be accomplished by many methods known in the art. Often the formulation will include an acceptable carrier, such as an oil, or other suspending or emulsifying agent.

Suitable optional carriers include but are not limited to, for example, fatty acids, esters and salts thereof, that can be derived from any source, including, without limitation, natural or synthetic oils, fats, waxes or combinations thereof. Moreover, the fatty acids can be derived, without limitation, from non-hydrogenated oils, partially hydrogenated oils, fully hydrogenated oils or combinations thereof. Non-limiting exemplary sources of fatty acids (their esters and salts) include seed oil, fish or marine oil, canola oil, vegetable oil, safflower oil, sunflower oil, nasturtium seed oil, mustard seed oil, olive oil, sesame oil, soybean oil, corn oil, peanut oil, cottonseed oil, rice bran oil, babassu nut oil, palm oil, low erucic rapeseed oil, palm kernel oil, lupin oil, coconut oil, flaxseed oil, evening primrose oil, jojoba, wheat germ oil, tallow, beef tallow, butter, chicken fat, lard, dairy butterfat, shea butter or combinations thereof.

Specific non-limiting exemplary fish or marine oil sources include shellfish oil, tuna oil, mackerel oil, salmon oil, menhaden, anchovy, herring, trout, sardines or combinations thereof. In particular, the source of the fatty acids is fish or marine oil (DHA or EPA), soybean oil or flaxseed oil. Alternatively or in combination with one of the above identified carrier, beeswax can be used as a suitable carrier, as well as suspending agents such as silica (silicon dioxide).

The formulations of the invention are also considered to be nutraceuticals. The term "nutraceutical" is recognized in the art and is intended to describe specific chemical compounds found in foods that can prevent disease or ameliorate an undesirable condition.

The formulations of the invention can further include various ingredients to help stabilize, or help promote the bioavailability of the components of the beneficial compositions of the invention or serve as additional nutrients to an individual's diet. Suitable additives can include vitamins and biologically-acceptable minerals. Non-limiting examples of vitamins include vitamin A, B vitamins, vitamin C, vitamin D, vitamin E, vitamin K and folic acid. Non-limiting examples of minerals include iron, calcium, magnesium, potassium, copper, chromium, zinc, molybdenum, iodine, boron, selenium, manganese, derivatives thereof or combinations thereof. These vitamins and minerals can be from any source or combination of sources, without limitation. Non-limiting exemplary B vitamins include, without limitation, thiamine, niacinamide, pyridoxine, riboflavin, cyanocobalamin, biotin, pantothenic acid or combinations thereof.

Various additives can be incorporated into the present compositions. Optional additives of the present composition include, without limitation, hyaluronic acid, phospholipids, starches, sugars, fats, antioxidants, amino acids, proteins, flavorings, coloring agents, hydrolyzed starch(es) and derivatives thereof or combinations thereof.

As used herein, the term "antioxidant" is recognized in the art and refers to synthetic or natural substances that prevent or delay the oxidative deterioration of a compound. Exemplary antioxidants include tocopherols, flavonoids, catechins, superoxide dismutase, lecithin, gamma oryzanol; vitamins, such as vitamins A, C (ascorbic acid) and E and beta-carotene; natural components such as camosol, camosic acid and rosmanol found in rosemary and hawthorn extract, proanthocyanidins such as those found in grapeseed or pine bark extract, and green tea extract.

Compositions comprising the stabilized anthocyanin compositions of the invention can be manufactured by methods of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries that facilitate processing of the stabilized anthocyanin compositions into preparations that can be used.

The compositions of the invention can take a form suitable for virtually any mode of administration, including, for example, oral, buccal, systemic, injection, transdermal, rectal, vaginal, etc., or a form suitable for administration by inhalation or insufflation.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the stabilized anthocyanin compositions in aqueous or oily vehicles. The compositions can also contain formulating agents, such as suspending, stabilizing and/or dispersing agent. The formulations for injection can be presented in unit dosage form, e.g., in ampoules or in multi-dose containers, and can contain added preservatives.

Alternatively, the injectable formulation can be provided in powder form for reconstitution with a suitable vehicle, including but not limited to sterile pyrogen free water, buffer, dextrose solution, etc., before use. To this end, the stabilized anthocyanin compositions can be dried by any art-known technique, such as lyophilization, and reconstituted prior to use.

For transmucosal administration, penetrants appropriate to the barrier to be permeated are used in the formulation. Such penetrants are known in the art.

For oral administration, the compositions of the invention can take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars, films or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol, or fractionated vegetable oils); and preservatives (e.g., methyl or propyl p hydroxybenzoates or sorbic acid). The preparations can also contain buffer salts, preservatives, flavoring, coloring and sweetening agents as appropriate.

Preparations for oral administration can be suitably formulated to give controlled release of the stabilized anthocyanin composition as is well known.

For buccal administration, the compositions can take the form of tablets or lozenges formulated in conventional manner.

For rectal and vaginal routes of administration, the stabilized anthocyanin compositions can be formulated as solutions (for retention enemas) suppositories or ointments containing conventional suppository bases such as cocoa butter or other glycerides.

For nasal administration or administration by inhalation or insufflation, the stabilized anthocyanin compositions can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

For prolonged delivery, the stabilized anthocyanin compositions can be formulated as a depot preparation for administration by implantation or intramuscular injection. The stabilized anthocyanin compositions can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch, which slowly releases the stabilized anthocyanin compositions for percutaneous absorption, can be used. To this end, permeation enhancers can be used to facilitate transdermal penetration of the stabilized anthocyanin compositions. Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; 4,921,475.

Alternatively, other delivery systems can be employed. Liposomes and emulsions are well-known examples of delivery vehicles that can be used to deliver stabilized anthocyanin compositions. Certain organic solvents such as dimethylsulfoxide (DMSO) can also be employed, although usually at the cost of greater toxicity.

The compositions can, if desired, be presented in a pack or dispenser device, which can contain one or more unit dosage forms containing the stabilized anthocyanin compositions. The pack can, for example, comprise metal or plastic foil, such as a blister pack. The pack or dispenser device can be accompanied by instructions for administration.

Soft gel or soft gelatin capsules can be prepared, for example, without limitation, by dispersing the formulation in an appropriate vehicle (e.g., rice bran oil, and/or beeswax) to form a high viscosity mixture. This mixture is then encapsulated with a gelatin based film using technology and machinery known to those in the soft gel industry. The capsules so formed are then dried to constant weight. Typically, the weight of the capsule is between about 100 to about 2500 milligrams and in particular weigh between about 1500 and about 1900 milligrams, and more specifically can weigh between about 1500 and about 2000 milligrams.

For example, when preparing soft gelatin shells, the shell can include between about 20 to 70 percent gelatin, generally a plasticizer and about 5 to about 60% by weight sorbitol. The filling of the soft gelatin capsule is liquid (principally a carrier such as rice bran oil or wheat germ oil and/or beeswax if desired) and can include, apart from the stabilized anthocyanin compositions, a hydrophilic matrix. The hydrophilic matrix, if present, is a polyethylene glycol having an average molecular weight of from about 200 to 1000. Further ingredients are optionally thickening agents and/or emulsifying agent(s). In one embodiment, the hydrophilic matrix includes polyethylene glycol having an average molecular weight of from about 200 to 1000, 5 to 15% glycerol, and 5 to 15% by weight of water. The polyethylene glycol can also be mixed with propylene glycol and/or propylene carbonate.

In another embodiment, the soft gel capsule is prepared from gelatin, glycerine, water and various additives. Typically, the percentage (by weight) of the gelatin is between about 30 and about 50 weight percent, in particular between about 35 and about weight percent and more specifically about 42 weight percent. The formulation includes between about 15 and about 25 weight percent glycerine, more particularly between about 17 and about 23 weight percent and more specifically about 20 weight percent glycerine.

The remaining portion of the capsule is typically water. The amount varies from between about 25 weigh percent and about 40 weight percent, more particularly between about 30 and about 35 weight percent, and more specifically about 35 weight percent. The remainder of the capsule can vary, generally, between about 2 and about 10 weight percent composed of a flavoring agent(s), sugar, coloring agent(s), etc. or combination thereof. After the capsule is processed, the water content of the final capsule is often between about 5 and about 10 weight percent, more particularly 7 and about 12 weight percent, and more specifically between about 9 and about 10 weight percent.

As for the manufacturing, it is contemplated that standard soft shell gelatin capsule manufacturing techniques can be used to prepare the soft-shell product. Examples of useful manufacturing techniques are the plate process, the rotary die process pioneered by R. P. Scherer, the process using the Norton capsule machine, and the Accogel machine and process developed by Lederle. Each of these processes are mature technologies and are all widely available to any one wishing to prepare soft gelatin capsules.

Emulsifying agents can be used to help solubilize the ingredients within the soft gelatin capsule. Specific examples of the surfactant, emulsifier, or effervescent agent include D-sorbitol, ethanol, carrageenan, carboxyvinyl polymer, carmellose sodium, guar gum, glycerol, glycerol fatty acid ester, cholesterol, white beeswax, dioctyl sodium sulfosuccinate, sucrose fatty acid ester, stearyl alcohol, stearic acid, polyoxyl 40 stearate, sorbitan sesquioleate, cetanol, gelatin, sorbitan fatty acid ester, talc, sorbitan trioleate, paraffin, potato starch, hydroxypropyl cellulose, propylene glycol, propylene glycol fatty acid ester, pectin, polyoxyethylene (105) polyoxypropylene (5) glycol, polyoxyethylene (160) polyoxypropylene (30) glycol, polyoxyethylene hydrogenated castor oil, polyoxyethylene hydrogenated castor oil 40, polyoxyethylene hydrogenated castor oil 60, polyoxyl 35 castor oil, polysorbate 20, polysorbate 60, polysorbate 80, macrogol 400, octyldodecyl myristate, methyl cellulose, sorbitan monooleate, glycerol monostearate, sorbitan monopalmitate, sorbitan monolaurate, lauryl dimethylamine oxide solution, sodium lauryl sulfate, lauromacrogol, dry sodium carbonate, tartaric acid, sodium hydroxide, purified soybean lecithin, soybean lecithin, potassium carbonate, sodium hydrogen carbonate, medium-chain triglyceride, citric anhydride, cotton seed oil-soybean oil mixture, and liquid paraffin.

The present invention also provides packaged formulations of the compositions of the invention and instructions for use of the product for appropriate condition(s). Typically, the packaged formulation, in whatever form, is administered to an individual in need thereof. Typically, the dosage requirement is between about 1 to about 4 dosages a day.

Although the present invention describes the preparation, use, manufacture and packaging of the compositions of the invention in soft gelatin capsules for treatment of various conditions, it should not be considered limited to only soft gelatin capsules. Ingestible compositions of the invention can be delivered in traditional tablets, pills, lozenges, elixirs, emulsions, hard capsules, liquids, suspensions, etc. as described above.

The stabilized anthocyanin compositions of the invention, or compositions thereof, will generally be used in an amount effective to achieve the intended result, for example in an amount effective to treat or prevent the particular inflammatory related condition being treated. The composition can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a composition of the invention to a patient suffering from pain provides therapeutic benefit not only when the underlying condition is eradicated or ameliorated, but also when the patient reports a decrease in the severity or duration of the physical discomfort associated with the pain.

For prophylactic administration, the composition can be administered to a patient at risk of developing one of the previously described conditions.

The amount of composition administered will depend upon a variety of factors, including, for example, the particular indication being treated, the mode of administration, whether the desired benefit is prophylactic or therapeutic, the severity of the indication being treated and the age and weight of the patient, etc. Determination of an effective dosage is well within the capabilities of those skilled in the art.

Total dosage amounts of a stabilized anthocyanin composition will typically be in the range of from about 0.0001 or 0.001 or 0.01 mg/kg/day to about 100 mg/kg/day, but may be higher or lower, depending upon, among other factors, the activity of the components, its bioavailability, the mode of administration and various factors discussed above. Dosage amount and interval can be adjusted individually to provide plasma levels of the compound(s) which are sufficient to maintain therapeutic or prophylactic effect. For example, the compounds can be administered once per week, several times per week (e.g., every other day), once per day or multiple times per day, depending upon, among other things, the mode of administration, the specific indication being treated and the judgment of the prescribing physician. Skilled artisans will be able to optimize effective local dosages without undue experimentation.

The following paragraphs enumerated consecutively from 1 through 91 provide for various aspects of the present invention. In one embodiment, in a first paragraph (1), the present invention provides a stabilized anthocyanin extract composition comprising an anthocyanin extract and a stabilizing compound having at least one —SH group with the provisio that the stabilizing compound is not glutathione.

2. The stabilized anthocyanin extract composition of paragraph 1, wherein the stabilizing compound is yeast extract, dihydrolipoic acid, derivatives of dihydrolipoic acid, cysteine, derivatives of cysteine, SH-proteinase, SH-metalloproteinase, peptides containing cysteine, peptides containing glutathione, fermented oyster extract, thiolated chitosan, thiolated gelatin or mixtures thereof.

3. The stabilized anthocyanin extract composition of either paragraphs 1 or 2, wherein the anthocyanin extract is bilberry extract, blackcurrant extract, cranberry extract, black soybean extract, cowberry extract, blueberry extract or mixtures of two or more thereof.

4. The stabilized anthocyanin extract composition of any of paragraphs 1 through 3, wherein the mole ratio of stabilizing compound to anthocyanin extract is about 0.1 to about 10.

5. The stabilized anthocyanin extract composition of any of paragraphs 1 through 4, wherein the composition is stabile toward degradation when exposed to an aqueous environment with a pH of between about 2 and about 12.

6. The stabilized anthocyanin extract composition of any of paragraphs 1 through 5, wherein the anthocyanin extract comprises an anthocyanoside.

7. The stabilized anthocyanin extract of paragraph 1, wherein the anthocyanin extract includes an anthocyanoside.

8. The stabilized anthocyanin extract of paragraph 7, wherein the anthocyanoside is a glycoside of perlargonidin, peonidin, cyanidin, malvidin, petunidin, delphinidin or mixtures of two or more thereof.

9. A stabilized anthocyanin extract composition comprising an anthocyanin extract and a stabilizing compound having at least one —SH group.

10. The stabilized anthocyanin extract composition of paragraph 9, wherein the stabilizing compound is yeast extract, dihydrolipoic acid, derivatives of dihydrolipoic acid, cysteine, derivatives of cysteine, glutathione, derivatives of glutathione, SH-proteinase, SH-metalloproteinase, peptides containing cysteine, peptides containing glutathione, fermented oyster extract, thiolated chitosan, thiolated gelatin or mixtures thereof.

11. The stabilized anthocyanin extract composition of either of paragraphs 9 or 10, wherein the anthocyanin extract is bilberry extract, blackcurrant extract, cranberry extract, black soybean extract, cowberry extract, blueberry extract or mixtures of two or more thereof.

12. The stabilized anthocyanin extract composition of any of paragraphs 9 through 11, wherein the mole ratio of stabilizing compound to anthocyanin extract is about 0.1 to about 10.

13. The stabilized anthocyanin extract composition of any of paragraphs 9 through 12, wherein the composition is stabile toward degradation when exposed to an aqueous environment with a pH of between about 2 and about 12.

14. The stabilized anthocyanin extract of any of paragraphs 9 through 13, wherein the anthocyanin extract comprises an anthocyanoside.

15. The stabilized anthocyanin extract of paragraph 9, wherein the anthocyanin extract includes an anthocyanoside.

16. The stabilized anthocyanin extract of paragraph 15, wherein the anthocyanoside is a glycoside of perlargonidin, peonidin, cyanidin, malvidin, petunidin, delphinidin or mixtures of two or more thereof.

17. A method to stabilize an anthocyanin extract composition comprising the step of combining an anthocyanin extract with a sufficient amount of a stabilizing compound having at least one —SH group with the proviso that the stabilizing compound is not reduced glutathione, such that the anthocyanin extract is stabilized.

18. The method of paragraph 17, wherein the stabilizing compound is yeast extract, dihydrolipoic acid, derivatives of dihydrolipoic acid, cysteine, derivatives of cysteine, SH-proteinase, SH-metalloproteinase, peptides containing cysteine, peptides containing glutathioine, fermented oyster extract, thiolated chitosan, thiolated gelatin or mixtures thereof.

19. The method of either of paragraphs 17 or 18, wherein the anthocyanin extract is bilberry extract, blackcurrant extract, cranberry extract, black soybean extract, cowberry extract, blueberry extract or mixtures of two or more thereof.

20. The method of any of paragraphs 17 through 19, wherein the mole ratio of stabilizing compound to anthocyanin extract is about 0.1 to about 10.

21. The method of any of paragraphs 17 through 20, wherein the composition is stabile toward degradation when exposed to an aqueous environment with a pH of between about 2 and about 12.

22. The method of any of paragraphs 17 through 21, wherein the anthocyanin extract comprises an anthocyanoside.

23. The method of paragraph 17, wherein the anthocyanin extract includes an anthocyanoside.

24. The method of paragraph 23, wherein the anthocyanoside is a glycoside of perlargonidin, peonidin, cyanidin, malvidin, petunidin, delphinidin or mixtures of two or more thereof.

25. The method of paragraph 17, wherein the stabilized anthocyanin extract composition is stabile at ambient conditions for at least about one day.

26. The method of paragraph 22, wherein the stabilized anthocyanoside is stable at a pH of 7 for at least about 6 hours.

27. The method of paragraph 26, wherein the stabilized anthocyanoside maintained at a pH of 7 retains at least 50% of the anthocyanin as a glycoside over about 4 hours.

28. A method to stabilize an anthocyanin extract composition comprising the step of combining an anthocyanin extract with a sufficient amount of a stabilizing compound having at least one —SH group, such that the anthocyanin is stabilized.

29. The method of paragraph 28, wherein the stabilizing compound is yeast extract, dihydrolipoic acid, derivatives of dihydrolipoic acid, cysteine, derivatives of cysteine, glutathione, derivatives of glutathione, SH-proteinase, SH-metalloproteinase, peptides containing cysteine, peptides containing glutathioine, fermented oyster extract, thiolated chitosan, thiolated gelatin or mixtures thereof.

30. The method of either of paragraphs 28 or 29, wherein the anthocyanin extract is bilberry extract, blackcurrant extract, cranberry extract, black soybean extract, cowberry extract, blueberry extract or mixtures of two or more thereof.

31. The method of any of paragraphs 28 through 30, wherein the mole ratio of stabilizing compound to anthocyanin extract is about 0.1 to about 10.

32. The method of any of paragraphs 28 through 31, wherein the composition is stabile toward degradation when exposed to an aqueous environment with pH of between about 2 and about 12.

33. The method of any of paragraphs 28 through 32, wherein the anthocyanin extract comprises an anthocyanoside.

34. The method of paragraph 28, wherein the anthocyanin extract includes an anthocyanoside.

35. The method of paragraph 34, wherein the anthocyanoside is a glycoside of perlargonidin, peonidin, cyanidin, malvidin, petunidin, delphinidin or mixtures of two or more thereof.

36. The method of paragraph 28, wherein the stabilized anthocyanin extract composition is stabile at ambient conditions for at least about one day.

37. The method of paragraph 33, wherein the stabilized anthocyanoside is stable at a pH of 7 for at least about six hours.

38. The method of paragraph 37, wherein the stabilized anthocyanoside maintained at a pH of 7 retains at least 50% of the anthocyanin as a glycoside over about 4 hours.

39. A pH stabilized anthocyanin extract composition comprising an anthocyanin extract and a stabilizing compound having at least one —SH group.

40. The pH stabilized anthocyanin extract composition of paragraph 39, wherein the stabilizing compound is yeast extract, dihydrolipoic acid, derivatives of dihydrolipoic acid, cysteine, derivatives of cysteine, glutathione, derivatives of glutathione, SH-proteinase, SH-metalloproteinase, peptides containing cysteine, peptides containing glutathioine, fermented oyster extract, thiolated chitosan, thiolated gelatin or mixtures thereof 41. The pH stabilized anthocyanin extract composition of either of paragraphs 39 or 40, wherein the anthocyanin extract is bilberry extract, blackcurrant extract, cranberry extract, black soybean extract, cowberry extract, blueberry extract or mixtures of two or more thereof 42. The pH stabilized anthocyanin extract composition of any of paragraphs 39 through 41, wherein the mole ratio of stabilizing compound to anthocyanin extract is about 0.1 to about 10.

43. The pH stabilized anthocyanin extract composition of any of paragraphs 39 through 42, wherein the composition is stabile toward degradation when exposed to an aqueous environment with a pH of between about 2 and about 12.

44. The pH stabilized anthocyanin extract composition of any of paragraphs 39 through 43, wherein the anthocyanin extract comprises an anthocyanoside.

45. The pH stabilized anthocyanin extract composition of paragraph 39, wherein the anthocyanin extract includes an anthocyanoside.

46. The pH stabilized anthocyanin extract composition of paragraph 45, wherein the anthocyanoside is a glycoside of perlargonidin, peonidin, cyanidin, malvidin, petunidin, delphinidin or mixtures of two or more thereof.

47. The pH stabilized anthocyanin extract composition of paragraph 39, wherein the stabilized anthocyanin extract is stabile at ambient conditions for at least about one day.

48. The pH stabilized anthocyanin extract composition of paragraph 44, wherein the stabilized anthocyanoside is stable at a pH of 7 for at least about six hours.

49. The pH stabilized anthocyanin extract composition of paragraph 48, wherein the stabilized anthocyanoside maintained at a pH of 7 retains at least 50% of the anthocyanin as a glycoside over about 4 hours.

50. A method to prepare a pH stabilized anthocyanin extract composition comprising the step of combining an anthocyanin extract and a stabilizing compound having at least one —SH group, such that the composition is pH stable.

51. The method of paragraph 50, wherein the stabilizing compound is yeast extract, dihydrolipoic acid, derivatives of dihydrolipoic acid, cysteine, derivatives of cysteine, glutathione, derivatives of glutathione, SH-proteinase, SH-metalloproteinase, peptides containing cysteine, peptides containing glutathioine, fermented oyster extract, thiolated chitosan, thiolated gelatin or mixtures thereof.

52. The method of either of paragraphs 50 or 51, wherein the anthocyanin extract is bilberry extract, blackcurrant extract, cranberry extract, black soybean extract, cowberry extract, blueberry extract or mixtures of two or more thereof.

53. The method of any of paragraphs 50 through 52, wherein the mole ratio of stabilizing compound to anthocyanin extract is about 0.1 to about 10.

54. The method of any of paragraph 50 through 53, wherein the composition is stabile toward degradation when exposed to an aqueous environment with a pH of between about 2 and about 12.

55. The method of any of paragraphs 50 through 54, wherein the anthocyanin extract comprises an anthocyanoside.

56. The method of paragraph 50, wherein the anthocyanin extract includes an anthocyanoside.

57. The method of paragraph 56, wherein the anthocyanoside is a glycoside of perlargonidin, peonidin, cyanidin, malvidin, petunidin, delphinidin or mixtures of two or more thereof.

58. The method of paragraph 50, wherein the stabilized anthocyanin extract is stabile at ambient conditions for at least about one day.

59. The method of paragraph 55, wherein the stabilized anthocyanoside is stable at a pH of 7 for at least about six hours.

60. The method of paragraph 59, wherein the stabilized anthocyanoside maintained at a pH of 7 retains at least 50% of the anthocyanin as a glycoside over about four hours.

61. A method of providing a therapeutically beneficial amount of a stabilized anthocyanin composition to a subject, comprising the step of administering to a subject a therapeutically beneficial amount of a stabilized anthocyanin composition as describeded in any of paragraphs 1 through 16 or paragraphs 39 through 49.

62. A method to treat arthrosclerosis comprising the step of administering a therapeutically effective amount of a stabilized anthocyanin composition as describeded in any of paragraphs 1 through 16 or paragraphs 39 through 49 to a subject.

63. A method to increase or maintain intracellular antioxidant concentration of an anthocyanin, comprising the step of administering a therapeutically effective amount of a stabilized anthocyanin composition as describeded in any of paragraphs 1 through 16 or paragraphs 39 through 49.

64. A method to alleviate or reduce pain in a subject comprising the step of administering a therapeutically effective amount of a stabilized anthocyanin composition as describeded in any of paragraphs 1 through 16 or paragraphs 39 through 49.

65. The stabilized anthocyanin extract of any of paragraphs 4, 12 or 42, wherein the mole ratio of stabilizing compound to anthocyanin extract is about 0.5 to about 5.

66. The stabilized anthocyanin extract of any of paragraphs 4, 12 or 42, wherein the mole ratio of stabilizing compound to anthocyanin extract is about 1 to about 1.

67. The stabilized anthocyanin extract of any of paragraphs 1 through 16 or 39 through 49, wherein said stabilized anthocyanin extract is in the form of a pill, tablet, powder, granule, pellicle, ointment, cream, paste, solution, mixture, syrup, mucilage, emulsion, tincture, spirit, paint, drops or decoction.

68. The stabilized anthocyanin extract of any of paragraphs 1 through 16 or 39 through 49, further comprising a physiologically acceptable adjuvant.

69. The stabilized anthocyanin extract of paragraph 68, wherein the adjuvant is a diluent, binder, disintegrating agent, lubricant, base, flavoring agent, sweetening agent, coloring agent, preservative, antioxidant, coating materials, film-forming materials, solvent, solubilizer, wetting agent, absorbent, filtering aid, emulsifying agent, surfactant, suspending agent, viscosity increasing agent, plasticizer, chelating agent, aerosol propellant, foaming agent, acidifying agent, alkalizing agent, buffering agent or mixtures thereof.

70. The method of any of paragraphs 20, 31 or 53, wherein the mole ratio of stabilizing compound to anthocyanin extract is about 0.5 to about 5.

71. The method of any of paragraphs 20, 31 or 53, wherein the mole ratio of stabilizing compound to anthocyanin extract is about 1 to about 1.

72. The stabilized anthocyanin extract of either of paragraphs 65 or 66, wherein the derivative of cysteine is N-acetylcysteine and the SH-proteinase is papain, bromelain, ficin, ehymopapain or mixtures thereof.

73. A method for stabilizing an anthocyanin-rich extract, comprising the step:
contacting an anthocyanin-rich extract with at least one stabilizing compound having at least one —SH group, wherein the stabilizing compound can be contacted with the anthocyanin at any time during the extraction process.

74. The method according to paragraph 73, wherein the compound having at least one —SH group is yeast extract, dihydrolipoic acid, cysteine, glutathione or mixtures thereof.

75. The method of paragraph 73, wherein the mole ratio of the stabilizing compound having at least one —SH group to the anthocyanin compound is between about 0.1 and about 10.

76. The method of paragraph 75, wherein the mole ratio is between about 0.5 and about 5.

77. The method of paragraph 75, wherein the mole ratio is about 1.

78. The method of any of paragraphs 73 through 77, wherein the compound having at least one —SH group is added to the extraction solvent prior to contact with the anthocyanin-rich extract.

79. The method of any of paragraph 73 through 77, wherein the compound having at least one —SH group is added to the extraction solvent after the anthocyanin-rich extract is combined with an extraction solvent.

80. A method to treat age-related macular degeneration (AMD), a cataract, or retinopathy comprising the step of administering a therapeutically effective amount of a stabilized anthocyanin composition as described in any of paragraphs 1 through 16 or paragraphs 39 through 49 to a subject in need thereof.

81. A stabilized bilberry composition comprising bilberry extract and cysteine.

82. The stabilized bilberry composition of paragraph 81 wherein the ratio of bilberry extract to cysteine is about 10 to about 1 on a weight basis.

83. The stabilized bilberry composition of either of paragraphs 81 or 82, wherein the composition is spray dried.

84. The stabilized bilberry composition of any of paragraphs 81 through 83, wherein the stabilized composition retains at least about 80% of the original anthocyanosides for a period of at least about 6 months as determined by HPLC analysis.

85. A method to increase the bioavailability of an anthocyanin composition comprising the step of providing to a subject an anthocyanin composition comprising an anthocyanin and a compound having at least one —SH group, wherein the amount of anthocyanin is increased in the subject by a least twice the amount in comparison to a sample of an anthocyanin composition devoid of a compound having at least one —SH group.

86. The method of paragraph 85, wherein the anthocyanin material is an extract.

87. The method of paragraph 86, wherein the extract is bilberry extract.

88. The method of paragraph 85, wherein the ratio of anthocyanin material to the compound having at least one —SH group is between about 10:0.1 and about 1:1 based on a weight basis.

89. The method of paragraph 87, wherein the ratio of anthocyanin in the bilberry extract to the compound having at least one —SH group is between about 10 to about 1.

90. The method of paragraph 85, wherein the plasma concentration of the anthocyanin in the presence of cysteine post four hours of administration is at least twice the amount of a plasma concentration of anthocyanin absent the presence of the compound having at least one —SH group.

91. The method of any of paragraphs 85 through 90, wherein the compound having at least one —SH group is yeast, dihydrolipoic acid, derivatives of dihydrolipoic acid, cysteine, derivatives of cysteine, glutathione, derivatives of glutathione, SH-proteinase, SH-metalloproteinase, peptides containing cysteine, peptides containing glutathione, fermented oyster extract, thiolated chitosan, thiolated gelatin or mixtures thereof.

The following examples are not to be meant as limiting but are presented to provide additional information and support for the invention.

The present exemplary section relates to bilberry extract and black currant extract, as shown in the table below:

|  | Producer | Lot. No. |
| --- | --- | --- |
| Bilberry extract | Omya-Peralta GmbH | BB0823-1 |
| Black currant extract | Omya-Peralta GmbH | BC6006 |

EXAMPLE 1

Sample a) 60 mg bilberry extract [37% anthocyanosides] (0.048 mmol anthocyanosides expressed as cyanidin-3-O-glucoside) were added to a 100 ml flask and filled to volume with sodium phosphate buffer (5% [w/w], pH=7.0), and stirred until dissolution was complete. A 1 ml sample was taken immediately and acidified with formic acid to pH=1.0 and analyzed by HPLC for the content of anthocyanosides (Fresh Sample). The remaining solution was kept for 4 hours at 37° C. (water bath) with stirring. Thereafter another sample (Blank sample), representing unprotected degradation, was taken and acidified.

Sample b) 20 mg reduced L-glutathione (0.065 mmol) were added to a 100 ml flask with 60 ml sodium phosphate buffer (5% [w/w], pH=7.0) and stirred until dissolution was complete. 60 mg bilberry extract [37% anthocyanosides] (0.048 mmol expressed as cyanidin-3-O-glucoside) were then added and the flask was filled to volume with sodium phosphate buffer (5% [w/w], pH=7.0) and kept for 4 hours at 37° C. (water bath) with stirring.

Sample c) 30 mg dihydrolipoic acid (0.144 mmol) were added to a 100 ml flask with 60 ml sodium phosphate buffer (5% [w/w], pH=7.0) and stirred until dissolution was complete. 60 mg bilberry extract [37% anthocyanosides] (0.048 mmol expressed as cyanidin-3-O-glucoside) were then added and the flask was filled to volume with sodium phosphate buffer (5% [w/w], pH=7.0) and kept for 4 hours at 37° C. (water bath) with stirring.

After 4 hours, samples were taken and acidified immediately with formic acid to pH=1.0 and analyzed by HPLC for the content of anthocyanosides. Degradation is expressed as decrease in peak area of individual peaks (calculated as % left after 4 hours).

From the table below it was concluded that anthocyanosides are substantially more stable at pH=7.0 at 37° C. in presence of either DHLA or GSH when compared to blank (unprotected) samples. After 4 hours, the blank sample showed that about 25% of residual anthocyanosides were observed whereas the protected samples yielded more than 60% residual anthocyanosides. The protective efficacy of 30 mg DHLA is comparable to 20 mg GSH. The protective efficacy seems to be related to the basic anthocyanin-skeleton exemplified by delphinidin glycosides which are less well protected when compared to cyanidin glycosides. For each individual anthocyanoside tested, a protective effect, e.g. more residual anthocyanosides when compared to blank samples, was observed.

TABLE

Peak Area of anthocyanosides after incubation for 4 hours at 37° C.

| Peak ID. | Fresh (0 hours) | Blank (4 hours) | | DHLA (4 hours) | | GSH (4 hours) | |
| --- | --- | --- | --- | --- | --- | --- | --- |
|  |  | Area | % left | Area | % left | Area | % left |
| Dp-3O-Gal | 654.4 | 50.9 | 7.8 | 395.8 | 60.5 | 331.3 | 50.6 |
| Dp-3O-Glc | 726.6 | 46.3 | 6.4 | 414.8 | 57.1 | 350.8 | 48.3 |
| Cn-3O-Gal | 465.8 | 191.1 | 41.0 | 300.3 | 64.5 | 360.2 | 77.3 |
| Dp-3O-Ara | 564.9 | 39.1 | 6.9 | 364.4 | 64.5 | 283.6 | 50.2 |
| Cn-3O-Glc | 987.9 | 410.3 | 41.5 | 671.1 | 67.9 | 797.5 | 80.7 |
| Pt-3O-Gal | 216.4 | 40.7 | 18.8 | 132.8 | 61.4 | 150.0 | 69.3 |
| Cn-3O-Ara | 369.6 | 142.3 | 38.5 | 258.4 | 70.2 | 293.7 | 79.5 |
| Pt-3O-Glc | 473.4 | 78.8 | 16.6 | 271.9 | 57.4 | 315.6 | 66.7 |
| Pe-3O-Gal | 47.6 | 21.0 | 44.1 | 32.7 | 68.7 | 36.3 | 76.3 |
| Pt-3O-Ara | 140.6 | 22.8 | 16.2 | 93.7 | 66.6 | 97.6 | 69.4 |
| Pe-3O-Glc | 223.6 | 94.8 | 42.4 | 139.2 | 62.3 | 172.0 | 76.9 |
| Mv-3O-Gal | 179.1 | 67.3 | 37.6 | 112.5 | 62.8 | 133.2 | 74.4 |
| Pe-3O-Ara | 23.5 | 9.2 | 39.1 | 21.4 | 91.1 | 18.4 | 78.3 |
| Mv-3O-Glc | 455.9 | 164.7 | 36.1 | 287.4 | 63.0 | 336.2 | 73.7 |
| Mv-3O-Ara | 108.3 | 36.8 | 34.0 | 75.2 | 69.4 | 81.2 | 75.0 |
| Total | 5637.6 | 1416.1 | 25.1 | 3572.6 | 63.4 | 3757.6 | 66.7 |

Dp . . . Delphinidin, Cn . . . Cyanidin, Pt . . . Petunidin, Pe . . . Peonidin, Mv . . . Malvidin, Gal . . . Glactoside, Glc . . . Glucoside, Ara . . . Arabinoside Samples were prepared as outlined below in HPLC Analytical Method. Test stability samples were immediately acidified (to block degradation) and injected undiluted following the detailed description provided below.

EXAMPLE 2

Sample a) 60 mg bilberry extract [37% anthocyanosides] (0.048 mmol expressed as cyanidin-3-O-glucoside) were added to a 100 ml, filled to volume with sodium phosphate buffer (5% [w/w], pH=7.0) and stirred until dissolution was complete. A 1 ml sample was immediately taken and acidified with formic acid to pH=1.0 and analyzed by HPLC for the content of anthocyanosides. The remaining solution was kept at 37° C. (water bath) with stirring and additional 1 ml samples (Blank Samples), representing unprotected degradation, were sampled every 15 minutes. The samples were analyzed for selected anthocyanosides by HPLC.

Sample b) 20 mg reduced L-glutathione (0.065 mmol) were added to a 100 ml flask with 60 ml sodium phosphate buffer (5% [w/w], pH=7.0) and stirred until dissolution was complete. 60 mg bilberry extract [37% anthocyanosides] (0.048 mmol expressed as cyanidin-3-O-glucoside) were added and the flask was filled to volume with sodium phosphate buffer (5% [w/w], pH=7.0) and kept at 37° C. (water bath) with stirring. Every 15 minutes, 1 ml samples were taken and analyzed for selected anthocyanosides by HPLC.

From the tables below it was concluded that anthocyanosides are substantially more stable at pH=7.0 and 37° C. in presence of GSH when compared to blank samples. The protective activity started immediately after dissolution and lasts for at least 4 hours as indicated by the comparative decay of the selected anthocyanosides over time. Again, the protective effect is believed to be related to the anthocyanin-skeleton exemplified by 65% residual delphinidin-3-O-Galactose, 67% residual petunidin-3-O-Galactose and 77% residual cyanidin-3-O-galctose after incubation for 4 h 30 min. For each individual anthocyanosides tested a protective effect, e.g. more residual anthocyanosides when compared to blank samples, was observed.

TABLE

Peak Area of anthocyanosides after incubation at 37° C. (Blank Sample)

| Incubation Time (hours) | Dp-3O-Gal (Peak Area) | Cn-3O-Gal (Peak Area) | Pt-3O-Gal (Peak Area) |
|---|---|---|---|
| 0:00 | 699.51 | 498.85 | 237.44 |
| 0:15 | 547.09 | 390.37 | 179.60 |
| 0:30 | 603.54 | 433.94 | 203.39 |
| 0:45 | 451.09 | 347.29 | 152.46 |
| 1:00 | 467.23 | 380.25 | 161.49 |
| 1:15 | 354.36 | 305.40 | 124.16 |
| 1:30 | — | — | — |
| 1:45 | 401.11 | 353.94 | 144.59 |
| 2:00 | 356.25 | 337.90 | 132.38 |
| 2:15 | 320.33 | 320.70 | 121.96 |
| 2:30 | 262.70 | 271.19 | 96.36 |
| 2:45 | 264.07 | 274.22 | 99.38 |
| 3:00 | 288.65 | 324.58 | 127.47 |
| 3:15 | 289.95 | 324.25 | 123.02 |
| 3:30 | 237.41 | 281.19 | 98.72 |
| 3:45 | — | — | — |
| 4:00 | 243.90 | 315.54 | 107.51 |
| 4:15 | 226.99 | 300.50 | 102.44 |
| 4:30 | 135.48 | 205.36 | 58.78 |

—... No sample available

TABLE

Peak Area of anthocyanosides after incubation at 37° C. (GSH Protected Sample)

| Incubation Time (hours) | Dp-3O-Gal (Peak Area) | Cn-3O-Gal (Peak Area) | Pt-3O-Gal (Peak Area) |
|---|---|---|---|
| 0:00 | 731.12 | 508.09 | 248.16 |
| 0:15 | 739.50 | 504.88 | 245.04 |
| 0:30 | 674.83 | 470.61 | 222.35 |
| 0:45 | 598.57 | 425.89 | 195.63 |
| 1:00 | 652.53 | 462.71 | 213.84 |
| 1:15 | 648.70 | 452.17 | 210.34 |
| 1:30 | 618.45 | 431.86 | 202.34 |
| 1:45 | 609.47 | 442.86 | 194.88 |
| 2:00 | 583.66 | 436.19 | 193.23 |
| 2:15 | 592.13 | 442.30 | 199.06 |
| 2:30 | 528.71 | 390.23 | 169.36 |
| 2:45 | 560.24 | 422.32 | 183.97 |
| 3:00 | 562.10 | 433.21 | 189.41 |
| 3:15 | 562.39 | 425.54 | 185.92 |
| 3:30 | 553.82 | 422.54 | 181.53 |
| 3:45 | 495.67 | 397.72 | 173.03 |
| 4:00 | 563.95 | 446.42 | 193.79 |
| 4:15 | 540.10 | 419.80 | 179.46 |
| 4:30 | 531.62 | 420.37 | 181.46 |
| 4:45 | 478.52 | 393.21 | 166.84 |

TABLE

%-residual anthocyanosides after incubation at 37° C. for 4.30 hours

| | Dp-3O-Gal (% left) | Cn-3-O-Gal (% left) | Pt-3-O-Gal (% left) |
|---|---|---|---|
| Blank | 19% | 41% | 25% |
| GSH-protected | 65% | 77% | 67% |

Samples were prepared as outlined below in HPLC Analytical Method. Test stability samples were immediately acidified (to block degradation) and injected undiluted following the detailed description provided below.

EXAMPLE 3

Sample a) 60 mg black currant extract [35% anthocyanosides] (0.037 mmol anthocyanosides expressed as cyanidin-3-O-rutinoside) were added to a 100 ml flask and filled to volume with sodium phosphate buffer (5% [w/w], pH=7.0) and stirred until dissolution was complete. A 1 ml sample was taken immediately, acidified with formic acid to pH=1.0 and analyzed by HPLC for the content of anthocyanosides (Fresh Sample). The remaining solution was kept for 4 hours at 37° C. (water bath) with stirring. Thereafter samples (Blank sample), representing unprotected degradation, were taken and acidified.

Sample b) 20 mg reduced L-glutathione (0.065 mmol) were added to a 100 ml flask with 60 ml sodium phosphate buffer (5% [w/w], pH=7.0) and stirred until dissolution was complete. 60 mg black currant extract [35% anthocyanosides] (0.037 mmol anthocyanosides expressed as cyanidin-3-O-rutinoside) were then added and the flask was filled to volume with sodium phosphate buffer (5% [w/w], pH=7.0) and kept for 4 hours at 37° C. (water bath) with stirring.

Sample c) 20 mg dihydrolipoic acid (0.096 mmol) were added to a 100 ml flask with 60 ml sodium phosphate buffer (5% [w/w], pH=7.0) and stirred until dissolution was completed. 60 mg black currant extract [35% anthocyanosides] (0.037 mmol anthocyanosides expressed as cyanidin-3-O-rutinoside) were added to the flask, filled to volume with sodium phosphate buffer (5% [w/w], pH=7.0) and kept for 4 hours at 37° C. (water bath) with stirring.

Sample d) 20 mg L-cysteine acid (0.165 mmol) were added to a 100 ml flask with 60 ml sodium phosphate buffer (5% [w/w], pH=7.0) and stirred until dissolution was complete. 60 mg black currant extract [35% anthocyanosides] (0.037 mmol anthocyanosides expressed as cyanidin-3-O-rutinoside) were added to the flask, filled to volume with sodium phosphate buffer (5% [w/w], pH=7.0) and kept for 4 hours at 37° C. (water bath) with stirring.

After 4 hours samples were taken, acidified immediately with formic acid to pH=1.0 and analyzed by HPLC for the content of anthocyanosides. Degradation is expressed as decrease in peak area of individual peaks (calculated as % left after 4 hours).

From the table below it was determined that anthocyanosides are substantially more stable at pH=7.0 and 37° C. in presence of DHLA, GSH or L-cysteine when compared to blank samples. After 4 hours, in the blank sample between 9.5-33.4% of residual anthocyanosides were observed whereas the GSH protected samples yielded 50.4-65.0% residual anthocyanosides. Comparative figures for DHLA were 36.7-38.9%. For each individual anthocyanosides tested a protective effect, e.g. more residual anthocyanosides when compared to blank samples, was observed.

TABLE

Peak Area of anthocyanosides after incubation for 4 hours at 37° C.

| Peak ID | Fresh solution Area | Blank Area | Blank % left | DHLA 20 mg Area | DHLA 20 mg % left | GSH 20 mg Area | GSH 20 mg % left | L-cysteine 20 mg Area | L-cysteine 20 mg % left |
|---|---|---|---|---|---|---|---|---|---|
| Dp-3-O-Glc | 1481 | 140.8 | 9.5 | 770.7 | 52.0 | 745.6 | 50.4 | 543.0 | 36.7 |
| Dp-3-O-Rut | 5207 | 626.2 | 12.0 | 2692 | 51.7 | 2764 | 53.1 | 1975 | 38.0 |
| Cn-3-O-Glc | 491.1 | 154.0 | 31.4 | 254.1 | 51.7 | 315.7 | 64.3 | 186.8 | 38.0 |
| Cn-3-O-Rut | 3539 | 1183 | 33.4 | 1809 | 51.1 | 2299 | 65.0 | 1377 | 38.9 |

Dp . . . Delphinidin, Cn . . . Cyanidin, Glc . . . Glucoside, Rut . . . Rutinoside Samples were prepared as outlined below in HPLC Analytical Method. Test stability samples were immediately acidified (to block degradation) and injected undiluted following the detailed description provided below.

EXAMPLE 4

Sample a) 60 mg black currant extract [35% anthocyanosides] (0.037 mmol anthocyanosides expressed as cyanidin-3-O-rutinoside) were added to a 100 ml flask, filled to volume with sodium phosphate buffer (5% [w/w], pH=7.0) and stirred until dissolution was complete. The solution was kept for 4 hours at 37° C. (water bath) with stirring. Thereafter a sample (Blank sample), representing unprotected degradation, was taken and acidified.

Samples b-e) 5, 10, 20 or 60 mg dihydrolipoic acid (0.024-0.288 mmol) were added to 100 ml flasks with 60 ml sodium phosphate buffer (5% [w/w], pH=7.0) and stirred until dissolution was complete. To each flask was added 60 mg black currant extract [35 anthocyanosides] (0.037 mmol anthocyanosides expressed as cyanidin-3-O-rutinoside). The flasks were filled to volume with sodium phosphate buffer (5% [w/w], pH=7.0) and kept for 4 hours at 37° C. (water bath) with stirring.

Samples f-i) 5, 10, 20 or 60 mg GSH (0.016-0.192 mmol) were added to 100 ml flasks with 60 ml sodium phosphate buffer (5% [w/w], pH=7.0) and stirred until dissolution was complete. To each flask was added 60 mg black currant extract [35% anthocyanosides] (0.037 mmol anthocyanosides expressed as cyanidin-3-O-rutinoside). The flasks were filled to volume with sodium phosphate buffer (5% [w/w], pH=7.0) and kept for 4 hours at 37° C. (water bath) with stirring.

Samples j-m) 5, 10, 20 or 60 mg L-cysteine (0.041-0.492 mmol) were added to 100 ml flasks with 60 ml sodium phosphate buffer (5% [w/w], pH=7.0) and stirred until dissolution was complete. To each flask was added 60 mg black currant extract [35% anthocyanosides] (0.037 mmol anthocyanosides expressed as cyanidin-3-O-rutinoside). The flasks were filled to volume with sodium phosphate buffer (5% [w/w], pH=7.0) and kept for 4 hours at 37° C. (water bath) with stirring.

After 4 hours, samples were taken, acidified immediately with formic acid to pH=1.0 and analyzed by HPLC for the content of anthocyanosides. Degradation is expressed as a decrease in the sum peak area for 4 lead anthocyanosides (Dp-3-O-Glc, Dp-3-O-Rut, Cn-3-O-Glc, Cn-3-O-Rut), calculated as % left after 4 hours.

From the tables below it was determined that anthocyanosides were substantially protected by DHLA, GSH or L-cysteine in a dose-dependent manner.

TABLE

Peak Area of anthocyanosides after incubation for 4 hours at 37° C.

| DHLA added (mg) | Sum Peak Area Blank Sample | Sum Peak Area Protected Sample |
|---|---|---|
| 5 | 2103 | 3503 |
| 10 | 2103 | 3615 |
| 20 | 2103 | 3677 |
| 60 | 2103 | 3973 |

TABLE

Peak Area of anthocyanosides after incubation for 4 hours at 37° C.

| GSH added (mg) | Sum Peak Area Blank Sample | Sum Peak Area Protected Sample |
|---|---|---|
| 5 | 2103 | 2939 |
| 10 | 2103 | 3314 |
| 20 | 2103 | 4036 |
| 60 | 2103 | 4204 |

TABLE

Peak Area of anthocyanosides after incubation for 4 hours at 37° C.

| L-cysteine added (mg) | Sum Peak Area Blank Sample | Sum Peak Area Protected Sample |
|---|---|---|
| 5 | 2103 | 3119 |
| 10 | 2103 | 3625 |
| 20 | 2103 | 4190 |
| 60 | 2103 | 4202 |

Samples were prepared as outlined below in HPLC Analytical Method. Test stability samples were immediately acidified (to block degradation) and injected undiluted following the detailed description provided below.

EXAMPLE 5

Sample a) 60 mg black currant extract [35% anthocyanosides] (0.037 mmol anthocyanosides expressed as cyanidin-3-O-rutinoside) were added to a 100 ml flask, filled to volume with sodium phosphate buffer (5% [w/w], pH =7 .0) and stirred until dissolution was complete. A 1 ml sample was taken immediately, acidified with formic acid to pH=1.0 and analyzed by HPLC for the content of anthocyanosides. The remaining solution was kept at 37° C. (water bath) with stirring and 1 ml samples (Blank Samples), representing unprotected degradation, were taken every 15 minutes. The samples were analyzed for selected anthocyanosides by HPLC.

Sample b) 20 mg reduced L-glutathione (0.065 mmol) were added to a 100 ml flask with 60 ml sodium phosphate buffer (5% [w/w], pH=7.0) and stirred until dissolution was complete. 60 mg black currant extract [35% anthocyanosides] (0.037 mmol anthocyanosides expressed as cyanidin-3-O-rutinoside) were added, the flask was filled to volume with sodium phosphate buffer (5% [w/w], pH=7.0) and kept for at 37° C. (water bath) with stirring. Every 15 minutes 1 ml samples were taken and analyzed for selected anthocyanosides by HPLC.

From the tables below it could was determined that anthocyanosides are substantially more stable at pH=7.0 and 37° C. in presence of GSH when compared to blank samples. The protective activity starts immediately after dissolution and lasts for at least 4 hours as indicated by the comparative decay of the anthocyanosides over time. The protection efficacy may be dependent on the anthocyanin-skeleton, exemplified by the improved protection of cyanidin-glycosides when compared to delphinidin-glycosides. However, when comparing the blank to the protected sample, delphinidin-glycosides were substantially better protected than cyaniding-glycosides.

For each individual anthocyanosides tested a protective effect, e.g. more residual anthocyanosides when compared to blank samples, was observed.

TABLE

Peak Area of anthocyanosides after incubation at 37° C. (Blank sample)

| Incubation Time (hours) | Dp-3O-Glc (Peak Area) | Dp-3-O-Rut (Peak Area) | Cn-3-O-Glc (Peak Area) | Cn-3-O-Rut (Peak Area) |
|---|---|---|---|---|
| 0:00 | 1480.7 | 5207.5 | 491.1 | 3539.1 |
| 0:15 | 969.6 | 3604.2 | 368.9 | 2707.4 |
| 0:30 | 907.9 | 3366.5 | 361.9 | 2620.7 |
| 0:45 | 745.2 | 2787.9 | 321.0 | 2342.2 |
| 1:00 | 702.1 | 2660.6 | 312.0 | 2278.1 |
| 1:30 | 605.4 | 2299.5 | 293.4 | 2130.7 |
| 1:45 | 599.9 | 2291.6 | 283.8 | 2104.9 |
| 2:00 | 465.1 | 1825.7 | 256.7 | 1894.9 |
| 2:15 | 449.8 | 1747.2 | 250.3 | 1851.7 |
| 2:30 | 394.0 | 1552.5 | 243.9 | 1790.9 |
| 2:45 | 362.7 | 1442.9 | 226.8 | 1694.9 |
| 3:00 | 304.8 | 1235.4 | 213.7 | 1573.5 |
| 3:15 | 285.1 | 1166.0 | 204.9 | 1531.6 |
| 3:30 | 208.8 | 907.2 | 180.1 | 1370.4 |
| 3:45 | 214.5 | 891.1 | 181.6 | 1361.3 |
| 4:00 | 140.8 | 626.2 | 154.0 | 1182.9 |

TABLE

Peak Area of anthocyanosides after incubation at 37° C. (GSH protected sample)

| Incubation Time (hours) | Dp-3O-Glc (Peak Area) | Dp-3-O-Rut (Peak Area) | Cn-3-O-Glc (Peak Area) | Cn-3-O-Rut (Peak Area) |
|---|---|---|---|---|
| 0:00 | 1464.0 | 5201.3 | 480.6 | 3473.6 |
| 0:15 | 1280.4 | 4584.2 | 426.1 | 3108.1 |
| 0:45 | 1209.3 | 4275.7 | 418.6 | 2964.3 |
| 1:00 | 1219.0 | 4273.1 | 423.8 | 3015.3 |
| 1:15 | 1178.1 | 4168.7 | 415.3 | 2958.5 |
| 1:45 | 1051.8 | 3749.9 | 376.4 | 2688.8 |
| 2:00 | 1077.0 | 3813.3 | 387.6 | 2777.8 |
| 2:15 | 981.9 | 3544.9 | 356.5 | 2579.6 |
| 2:45 | 876.8 | 3199.5 | 337.5 | 2447.1 |
| 3:00 | 917.2 | 3327.2 | 349.5 | 2534.7 |
| 3:15 | 812.5 | 2993.9 | 325.6 | 2366.8 |
| 3:45 | 742.7 | 2761.0 | 312.6 | 2274.2 |
| 4:00 | 745.6 | 2763.6 | 315.7 | 2298.9 |
| 4:15 | 682.0 | 2579.8 | 300.3 | 2199.7 |

TABLE

%-residual anthocyanosides after incubation at 37° C. for 4 hours

|  | Dp-3O-Glc (% left) | Dp-3-O-Rut (% left) | Cn-3-O-Glc (% left) | Cn-3-O-Rut (% left) |
|---|---|---|---|---|
| Blank | 10% | 12% | 31% | 33% |
| GSH-protected | 51% | 53% | 66% | 66% |

Samples were prepared as outlined below in HPLC Analytical Method. Test stability samples were immediately acidified (to block degradation) and injected undiluted following the detailed description provided below.

EXAMPLE 6

Sample a) 5 mg delphinine chloride (0.015 mmol) was transferred into a 100 ml flask, dissolved in 1 ml methanol and filled to volume with sodium phosphate buffer (5% [w/w], pH=7.0). The sample was kept with stirring at 37° C. Samples were taken immediately after dissolution, after 15 minutes, 1, 2, and 3 hours of incubation. The samples were acidified with formic acid to pH=1.0 and analyzed by HPLC.

Sample b) 5 mg malvidin chloride (0.014 mmol) was transferred into a 100 ml flask, dissolved in 1 ml methanol and filled to volume with sodium phosphate buffer (5% [w/w], pH=7.0). The sample was kept with stirring at 37° C. Samples were taken immediately after dissolution and at 1, 2, and 3 hours of incubation. T he samples were acidified with formic acid to pH=1.0 and analyzed by HPLC.

Sample c) 5 mg delphinidine chloride (0.015 mmol) and 10 mg GSH (0.032 mmol) were transferred into a 100 ml flask, dissolved in 1 ml methanol and filled to volume with sodium phosphate buffer (5% [w/w], pH=7.0). The sample was kept with stirring at 37° C. Samples were taken at 15 minutes after dissolution and after 1, 2 and 3 hours of incubation. The samples were acidified with formic acid to pH=1.0 and analyzed by HPLC.

Sample d) 5 mg malvidin chloride (0.014 mmol) and 10 mg GSH (0.032 mmol) were transferred into a 100 ml flask, dissolved in 1 ml methanol and filled to volume with sodium phosphate buffer (5% [w/w], pH=7.0). The sample was kept with stirring at 37° C. Samples were taken 15 minutes after dissolution and after 1, 2 and 3 hours of incubation. The samples were acidified with formic acid to pH=1.0 and analyzed by HPLC.

From the table below it was determined that GSH did not protect well the free anthocyanin skeleton. The molar ratio between GSH and delphinidin or malvidin is higher than 2:1 indicating that the lack of activity is not related to a low concentration of GSH. The decay of the free anthocyanin is almost unaffected by the presence of GSH which is in contrast to the observations using anthocyanin-glycosides bearing the same skeleton.

TABLE

Peak Area of delphinidin and malvidin after incubation at 37° C.

| Time | Blank | | GSH 10 mg | |
|---|---|---|---|---|
| (hours) | Delphinidin | Malvidin | Delphinidin | Malvidin |
| 0 | 48.6 | 1228 | NA | NA |
| 0.25 | BLD | NA | BLD | NA |
| 1 | BLD | 661.6 | BLD | 530.1 |
| 2 | BLD | 175.3 | BLD | 263.5 |
| 3 | BLD | 56.4 | BLD | 5.6 |

BLD . . . Below Limit of Detection, NA . . . not applicable

Samples were prepared as outlined below in HPLC Analytical Method. Test stability samples were immediately acidified (to block degradation) and injected undiluted following the detailed description provided below.

EXAMPLE 7

Sample a) 60 mg bilberry extract [37% anthocyanosides] (0.048 mmol anthocyanosides expressed as cyanidin-3-O-glucoside) was added to a 100 ml flask, filled to volume with sodium phosphate buffer (5% [w/w], pH adjusted to the value given below) and stirred until dissolution was complete. The solution was kept for 4 hours at 37° C. (water bath) with stirring. Thereafter a sample (Blank sample), representing unprotected degradation, was taken and acidified to pH=1.0 with formic acid.

Sample b) 20 mg reduced L-glutathione (0.065 mmol) was added to a 100 ml flask with 60 ml sodium phosphate buffer (5% [w/w], pH adjusted to the value given below) and stirred until dissolution was complete. 60 mg bilberry extract [37% anthocyanosides] (0.048 mmol expressed as cyanidin-3-O-glucoside) was added to the flask, filled to volume with sodium phosphate buffer (5% [w/w], pH=7.0) and kept for 4 hours at 37° C. (water bath) with stirring.

After 4 hours samples were taken and acidified immediately with formic acid to pH=1.0 and analyzed by HPLC for the content of anthocyanosides. Degradation is expressed as decrease in the sum peak area for 4 anthocyanosides, calculated as % left after 4 hours.

From the table below it was determined that GSH protects anthocyanosides especially in the pH-range where anthocyanosides are susceptible to degradation (pH >5). Not surprisingly, at lower pH-values where anthocyanosides are stable by itself the protective effect is diminished.

TABLE

%-residual anthocyanosides after incubation at 37° C. for 4 hours

| | % residual anthocyanosides | |
|---|---|---|
| pH value | Blank Sample | 20 mg GSH |
| 3.0 | 87.3 | 97.0 |
| 5.0 | 81.9 | 86.5 |
| 7.0 | 25.1 | 66.7 |
| 9.0 | 8.8 | 40.5 |
| 10.0 | 4.0 | 18.8 |
| 11.0 | BLD | 3.1 |

Samples were prepared as outlined below in HPLC Analytical Method. Test stability samples were immediately acidified (to block degradation) and injected undiluted following the detailed description provided below.

The protection effect is a parameter that is calculated by dividing the residual ratio of the protected sample by the residual ratio of a blank sample (with bilberry extract at selected pH values without reduced glutathione). The difference thus demonstrates the effect of reduced L-glutathione (GSH) of the stability of anthocyanins of bilberry extract over a pH range of between about 3 and about 11.

Figure 19:
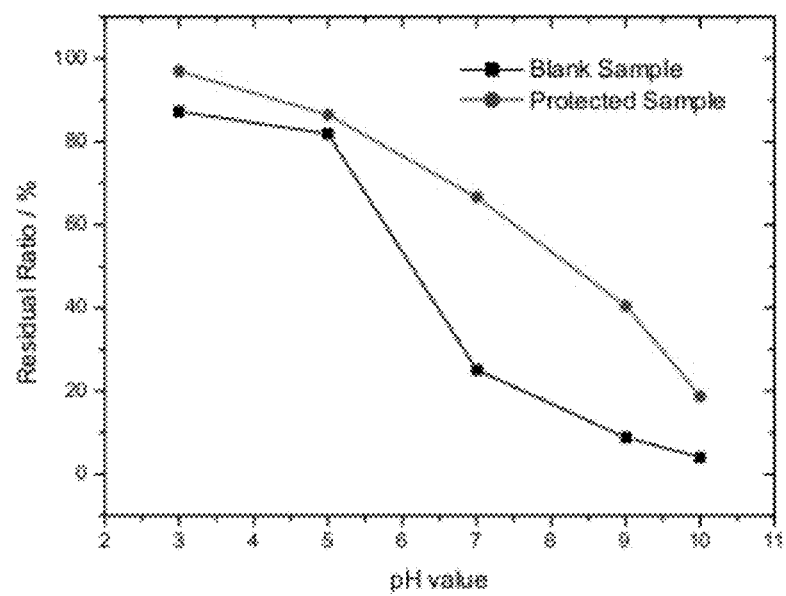
FIG. 19 is a graphical representation of the residual ratio and pH values over a pH range of 3 to 11 for the stability of bilberry extract treated with GSH and instability of bilberry extract not treated with GSH (at the same pH values).
Figure 20:
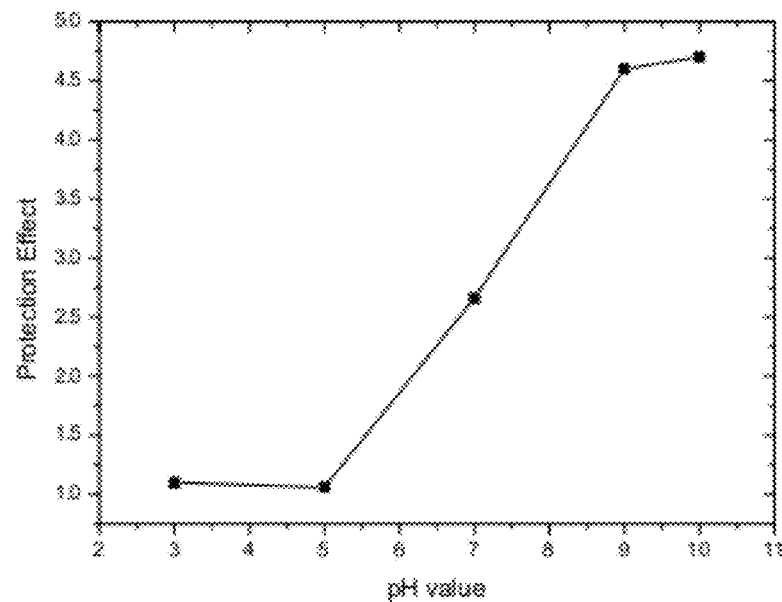
FIG. 20 is a graphical representation of the protective effect of GSH over a pH range.
Figure 21:
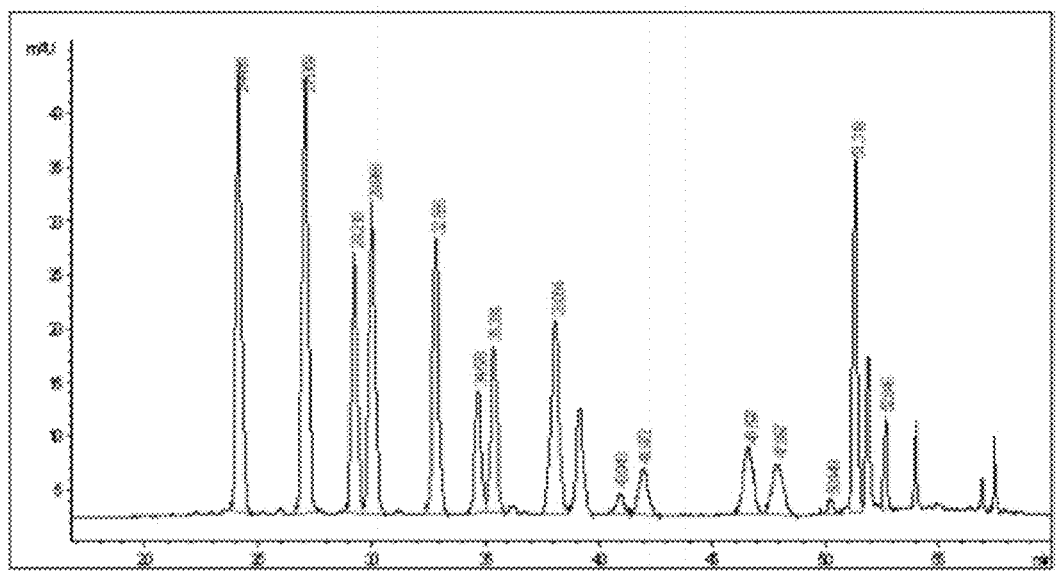
FIG. 21 is an HPLC chromatogram of fresh solution of 20070601, time zero.
Figure 22:
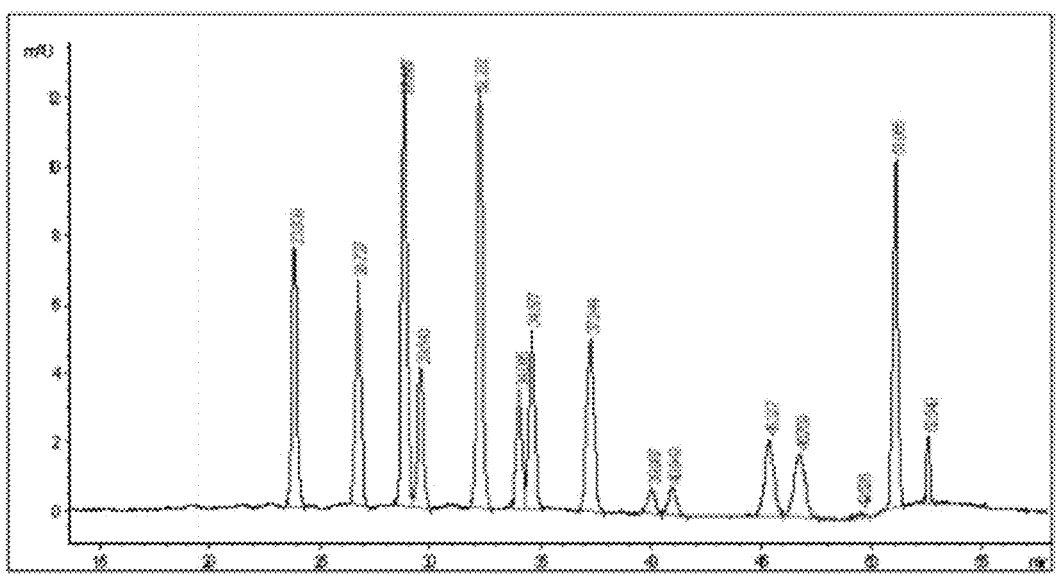
FIG. 22 is an HPLC chromatogram of 20070601 after 4 hours at 37° C.
Figure 23:
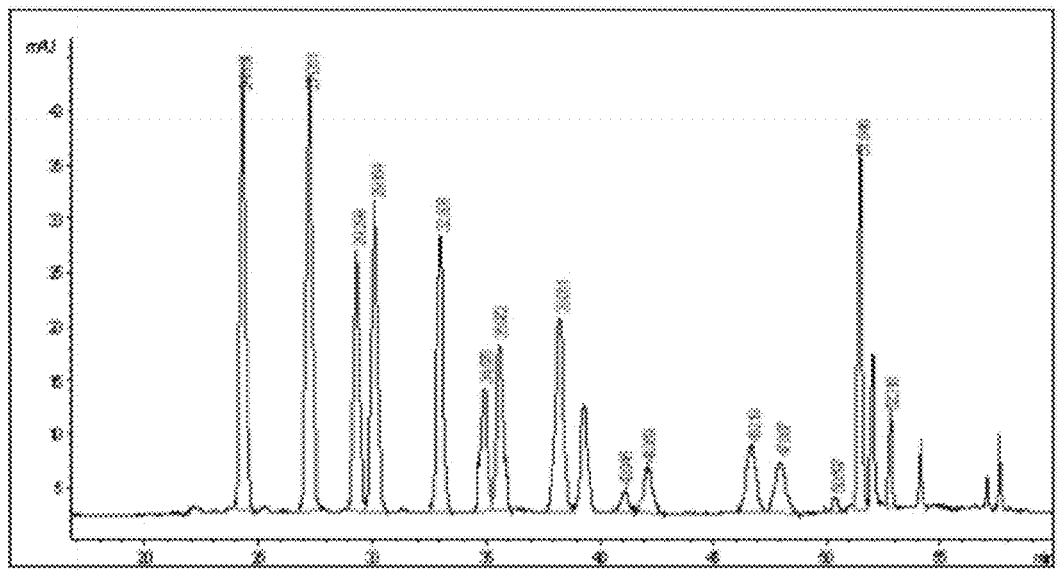
FIG. 23 is an HPLC chromatogram of fresh solution of 20070602, time zero.
Figure 24:
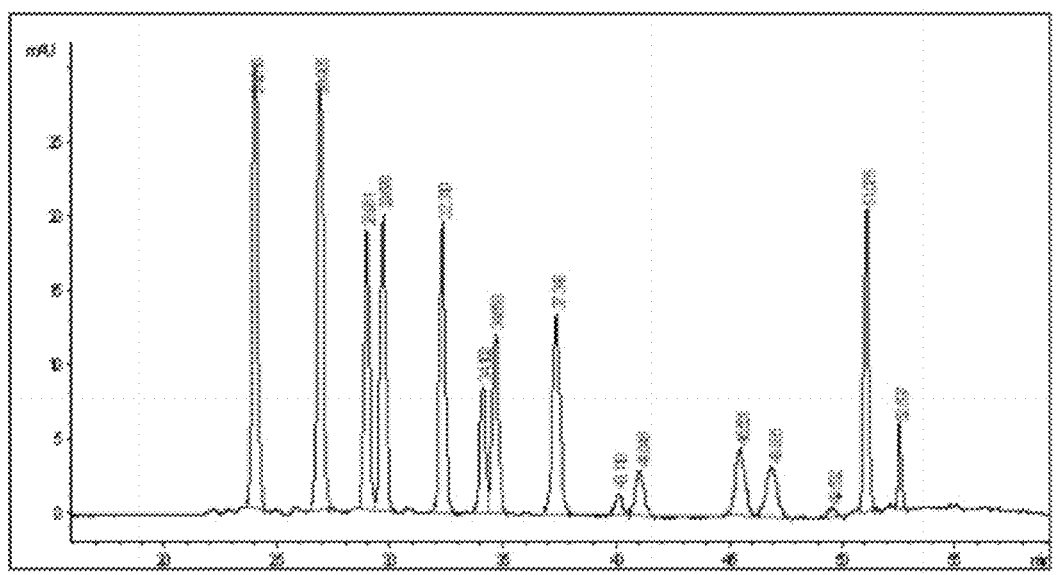
FIG. 24 is an HPLC chromatogram of 20070602 after 4 hours at 37° C.
Figure 25:
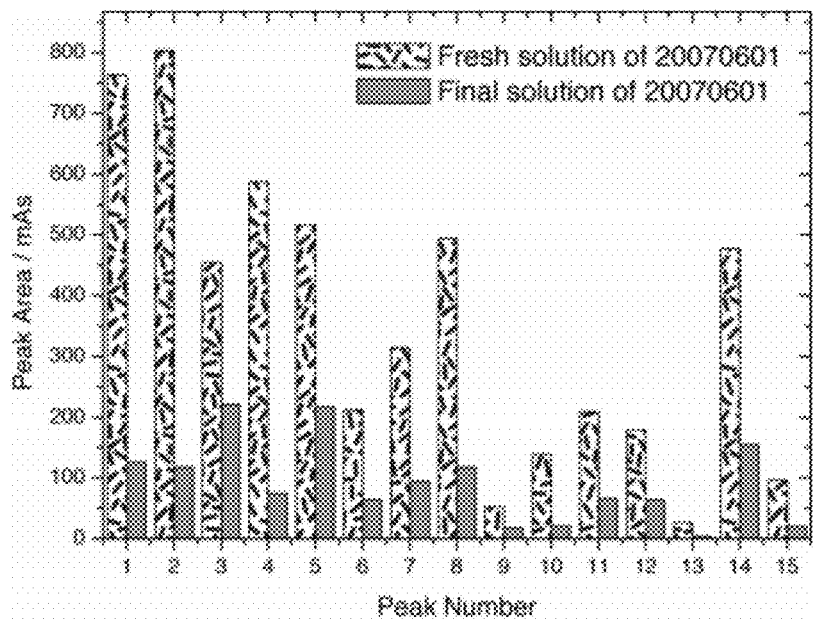
FIG. 25 provides HPLC peak comparisons of 20070601 at time zero and after 4 hours at 37° C.
Figure 26:
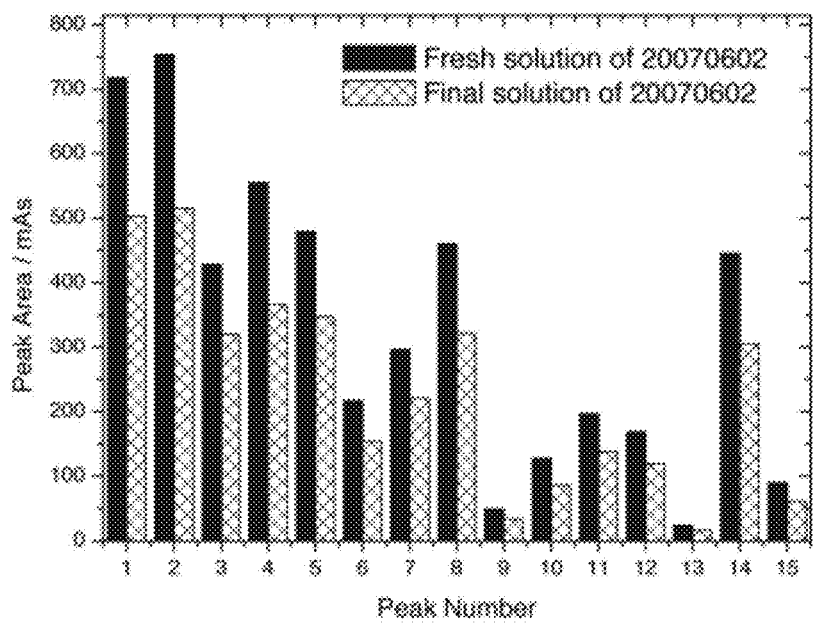
FIG. 26 provides HPLC peak comparisons of 20070602 at time zero and after 4 hours at 37° C.
Figure 29:
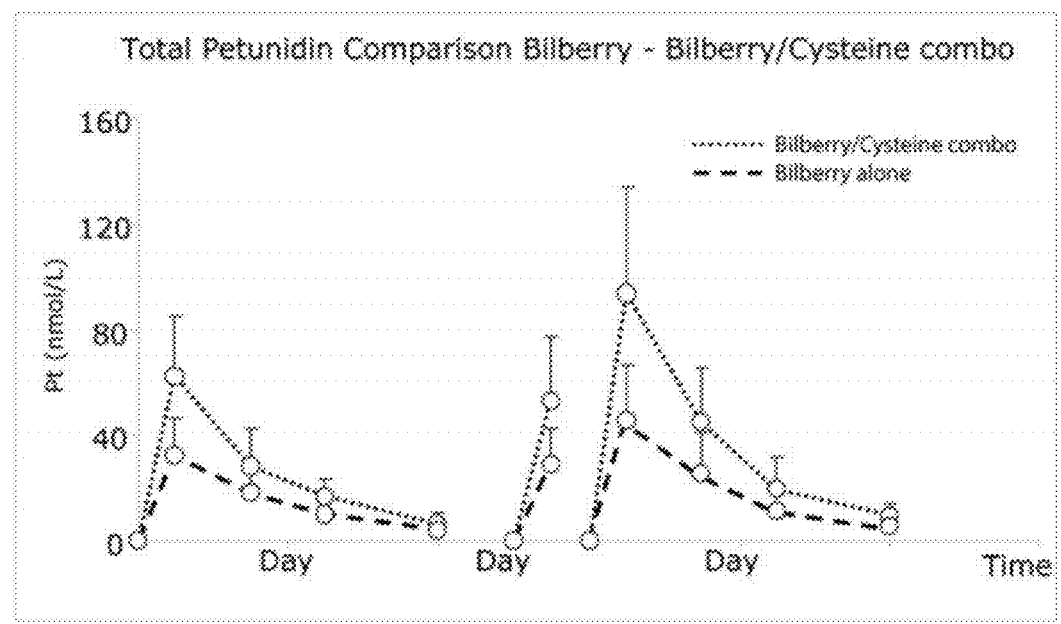
FIG. 29 provides a comparison of total petunidin observed in human plasma after treatment with bilberry extract or a bilberry/cysteine combination of the invention. Upper dotted line is bilberry/cysteine combination; lower hashed line is bilberry extract only.
Figure 30:
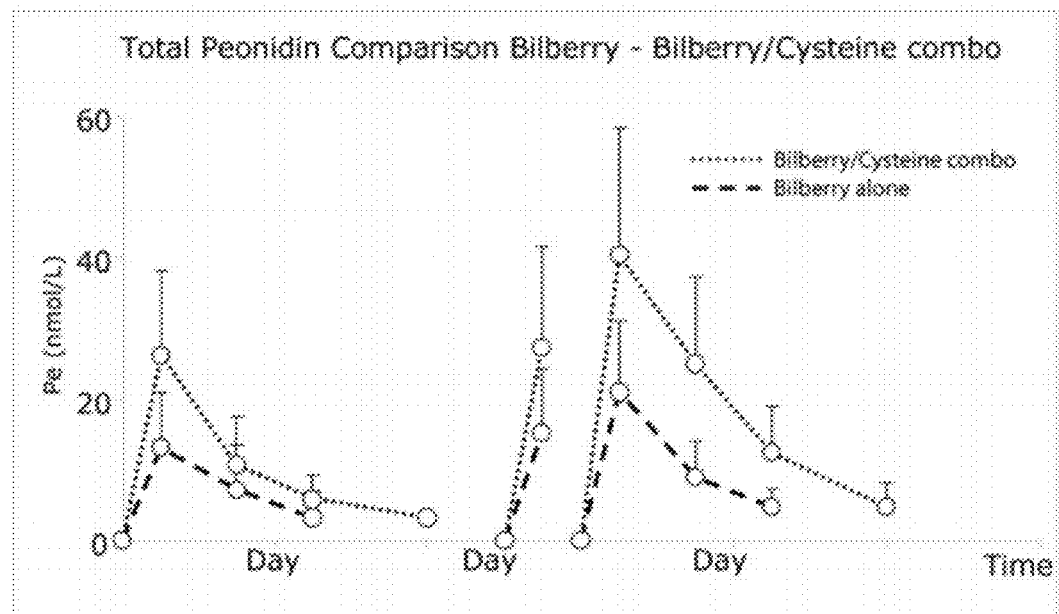
FIG. 30 provides a comparison of total peonidin observed in human plasma after treatment with bilberry extract or a bilberry/cysteine combination of the invention. Upper dotted line is bilberry/cysteine combination; lower hashed line is bilberry extract only.
Figure 31:
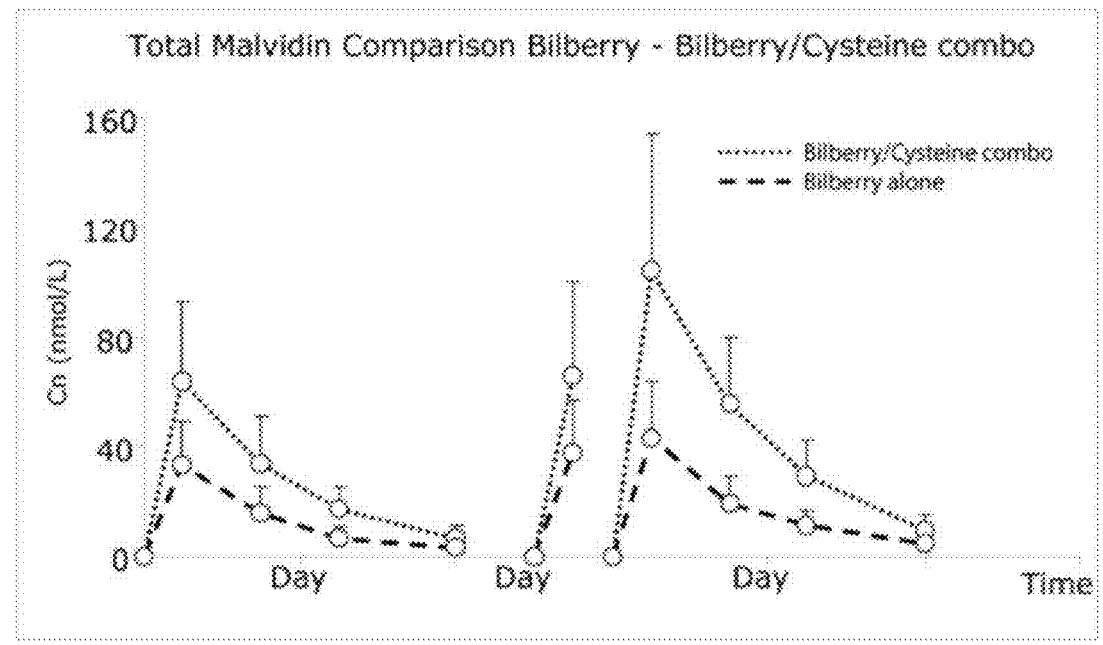
FIG. 31 provides a comparison of total malvidin observed in human plasma after treatment with bilberry extract or a bilberry/cysteine combination of the invention. Upper dotted line is bilberry/cysteine combination; lower hashed line is bilberry extract only.
Figure 32:
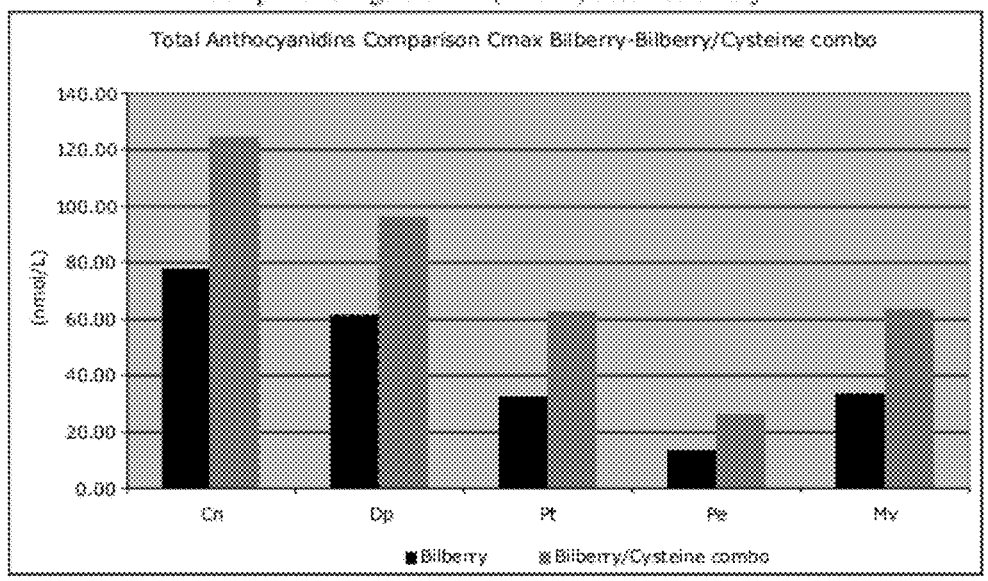
FIG. 32 provides comparative $C_{max}$ observed on day 1 for cyandin, delphinidin, petunidin, peonidin and malvidin for bilberry extract versus a bilberry extract/cysteine combination.
Figure 33:
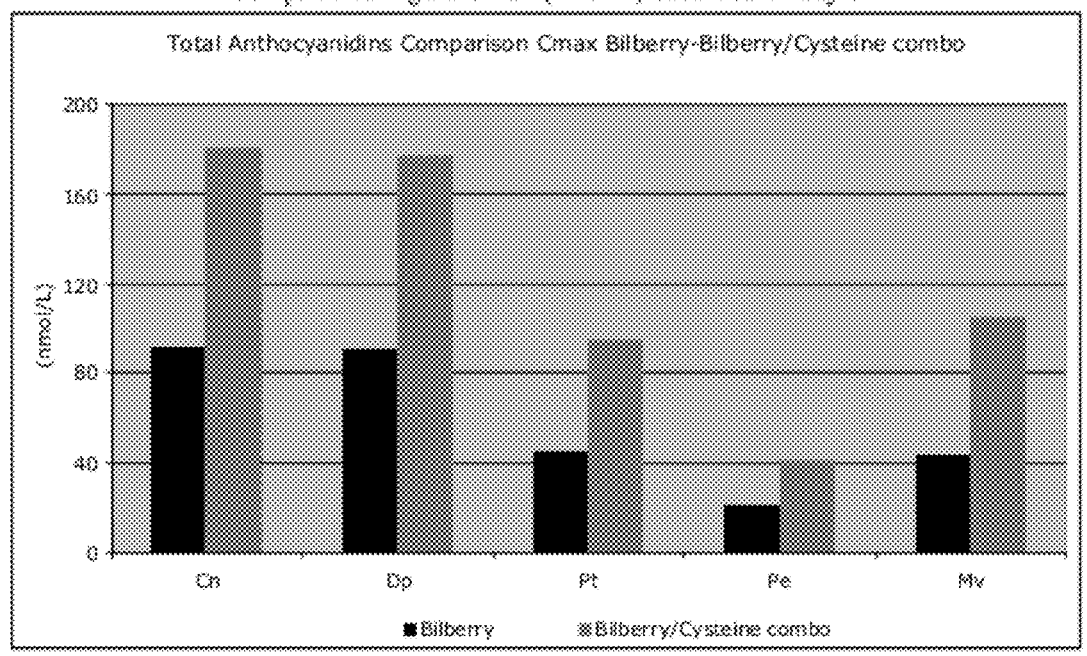
FIG. 33 provides comparative $C_{max}$ observed on day 7 for cyandin, delphinidin, petunidin, peonidin and malvidin for bilberry extract versus a bilberry extract/cysteine combination.
Figure 34:
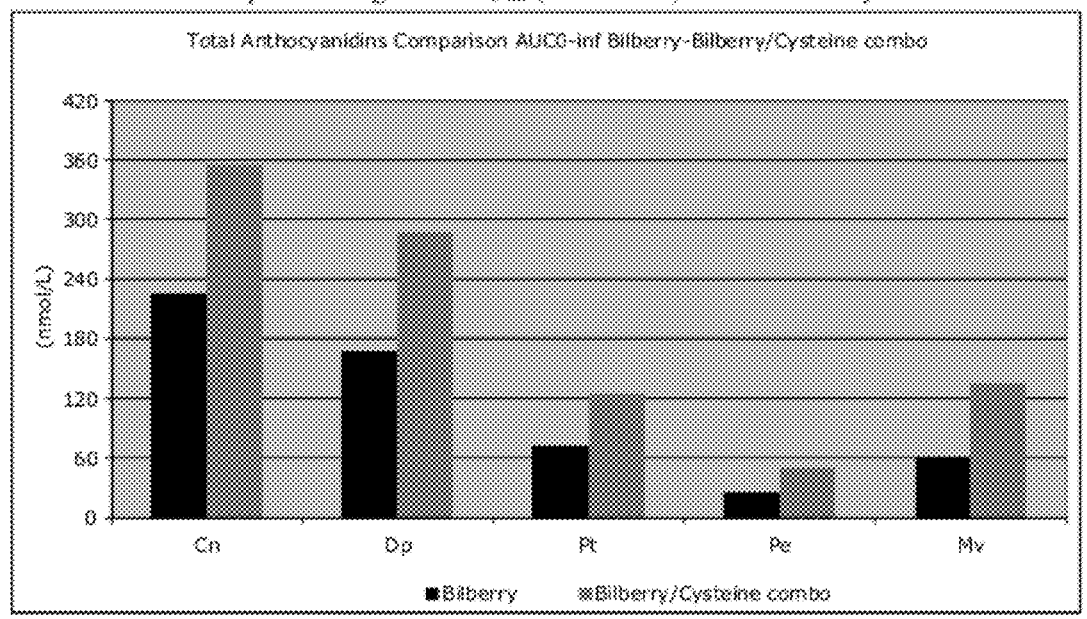
FIG. 34 provides comparative $AUC_{0\text{-}inf}$ observed on day 1 for cyandin, delphinidin, petunidin, peonidin and malvidin for bilberry extract versus a bilberry extract/cysteine combination.
Figure 36A:
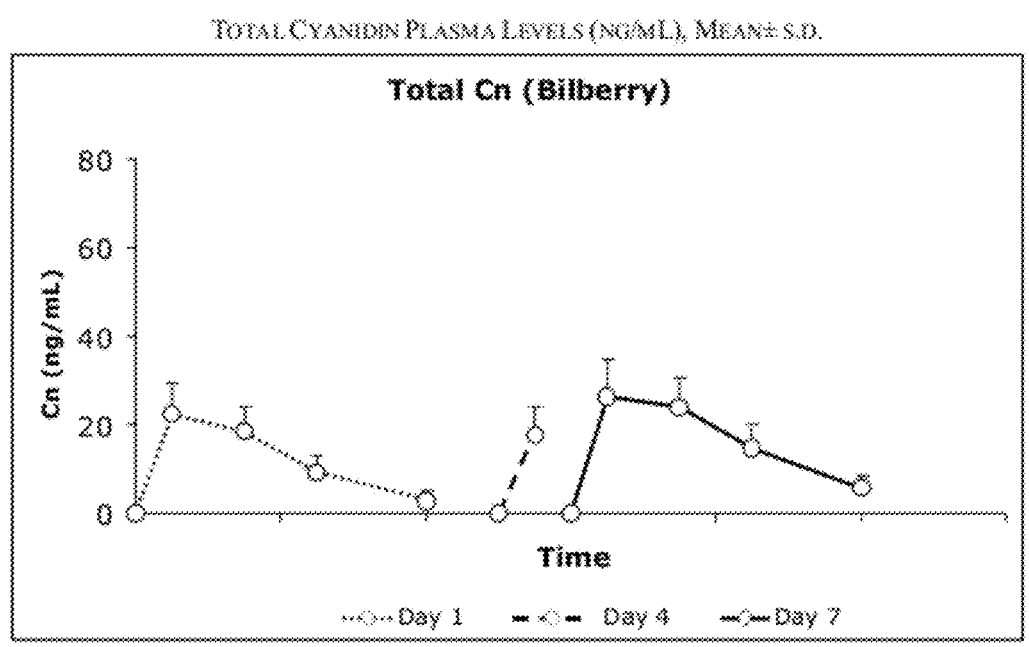
FIG. 36A provides total cyanidin plasma levels in plasma at 4 hours, 1 day, 7 days and on day 4, the two points represent 0 and 0.5 hours respectively for bilberry extract without cysteine.
Figure 36B:
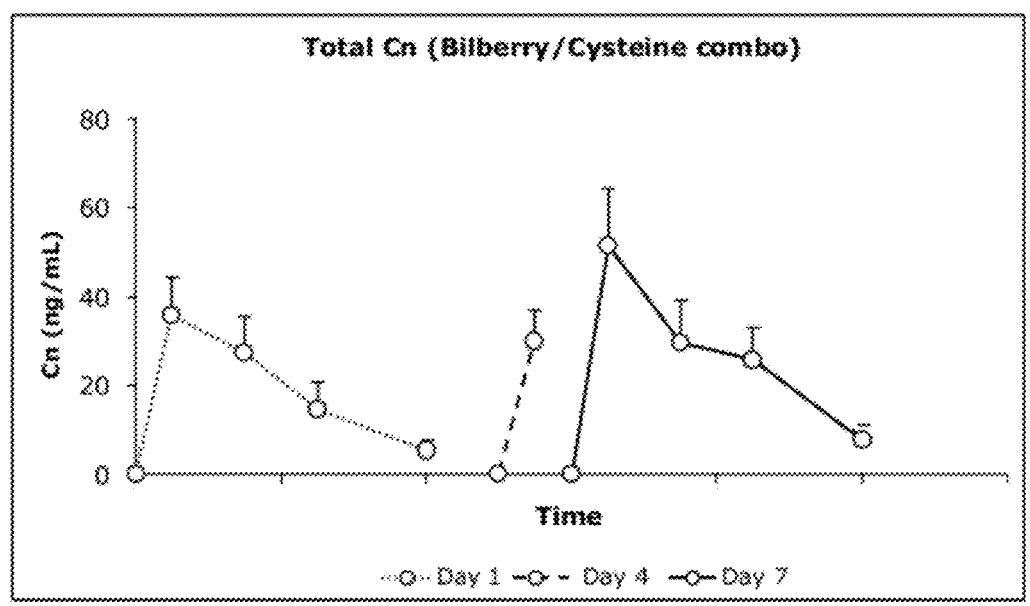
FIG. 36B provides total cyanidin plasma levels in plasma at 4 hours, 1 day, 7 days and on day 4, the two points represent 0 and 0.5 hours respectively for bilberry extract with cysteine.
Figure 37A:
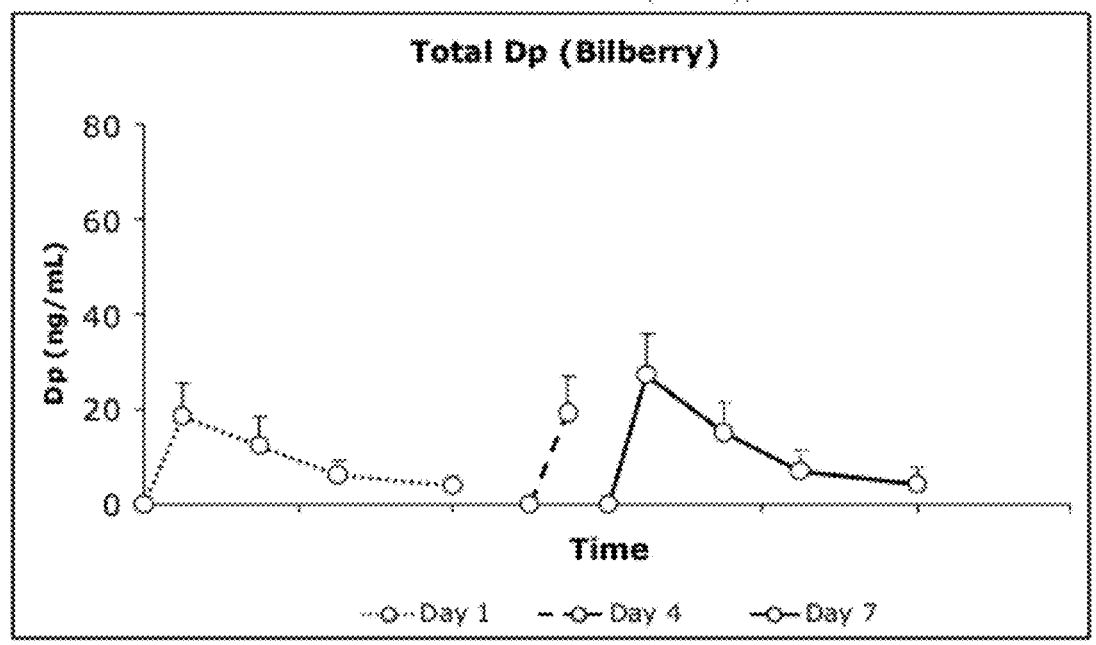
FIG. 37A provides total delphinidin plasma levels in plasma at 4 hours, 1 day, 7 days and on day 4, the two points represent 0 and 0.5 hours respectively for bilberry extract without cysteine.
Figure 37B:
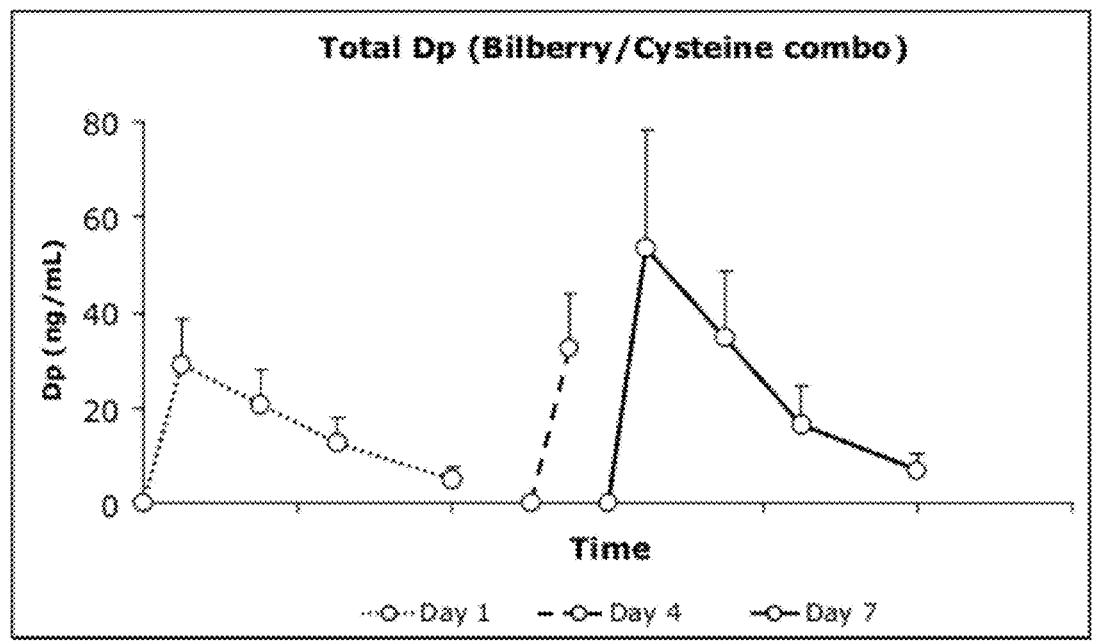
FIG. 37B provides total delphinidin plasma levels in plasma at 4 hours, 1 day, 7 days and on day 4, the two points represent 0 and 0.5 hours respectively for bilberry extract with cysteine.
Figure 38A:
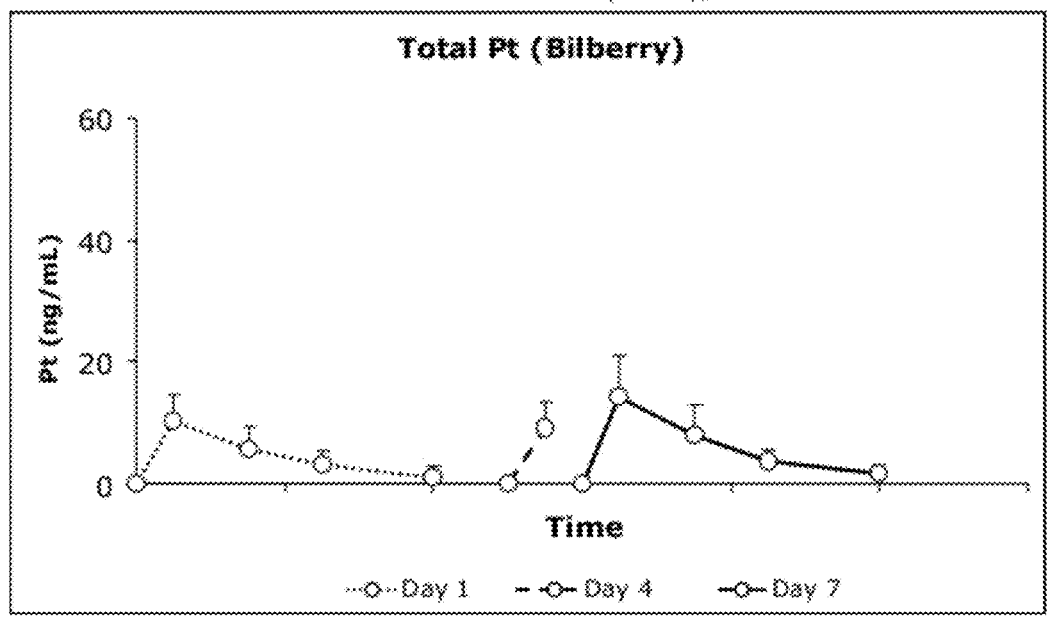
FIG. 38A provides total petunidin plasma levels in plasma at 4 hours, 1 day, 7 days and on day 4, the two points represent 0 and 0.5 hours respectively for bilberry extract without cysteine.
Figure 38B:
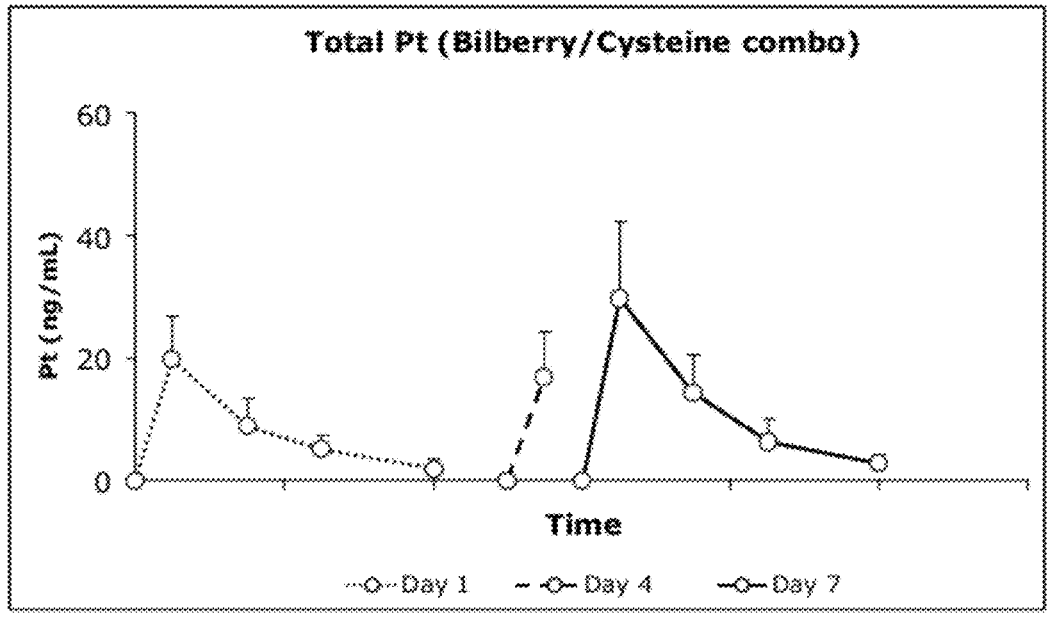
FIG. 38B provides total petunidin plasma levels in plasma at 4 hours, 1 day, 7 days and on day 4, the two points represent 0 and 0.5 hours respectively for bilberry extract with cysteine.
Figure 39A:
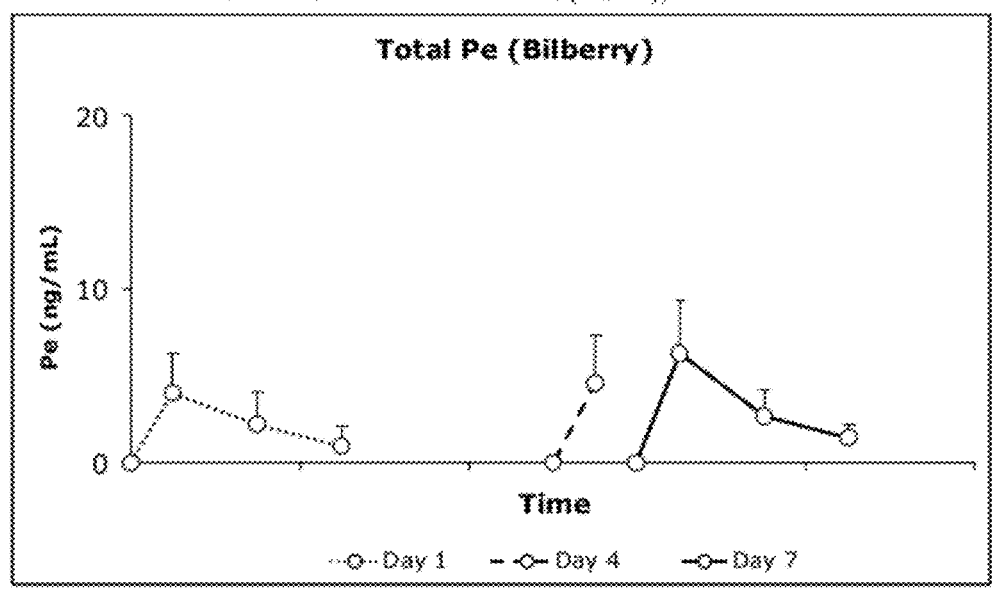
FIG. 39A provides total peonidin plasma levels in plasma at 4 hours, 1 day, 7 days and on day 4, the two points represent 0 and 0.5 hours respectively for bilberry extract without cysteine.
Figure 39B:
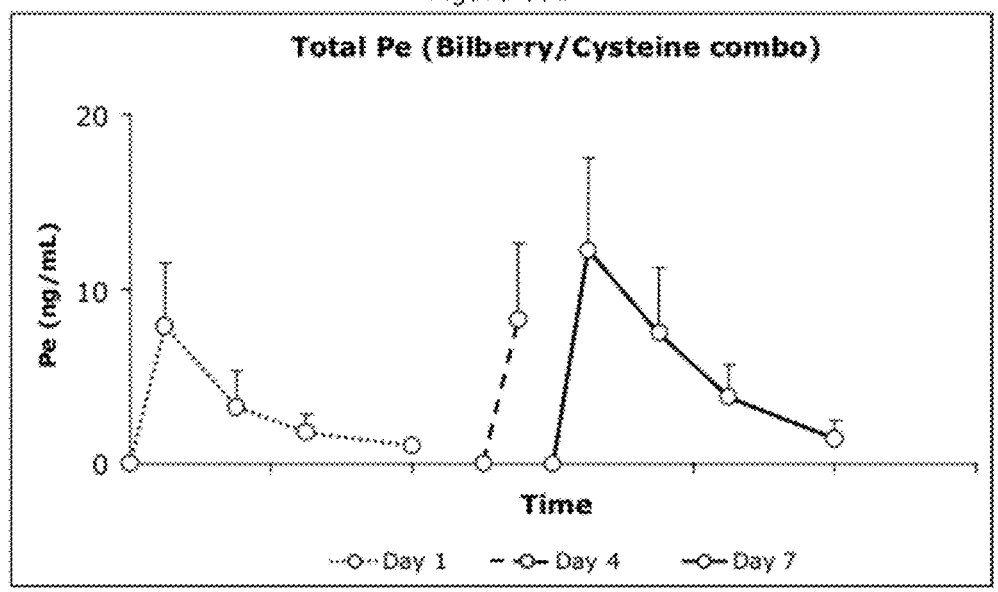
FIG. 39B provides total peonidin plasma levels in plasma at 4 hours, 1 day, 7 days and on day 4, the two points represent 0 and 0.5 hours respectively for bilberry extract with cysteine.
Figure 40A:
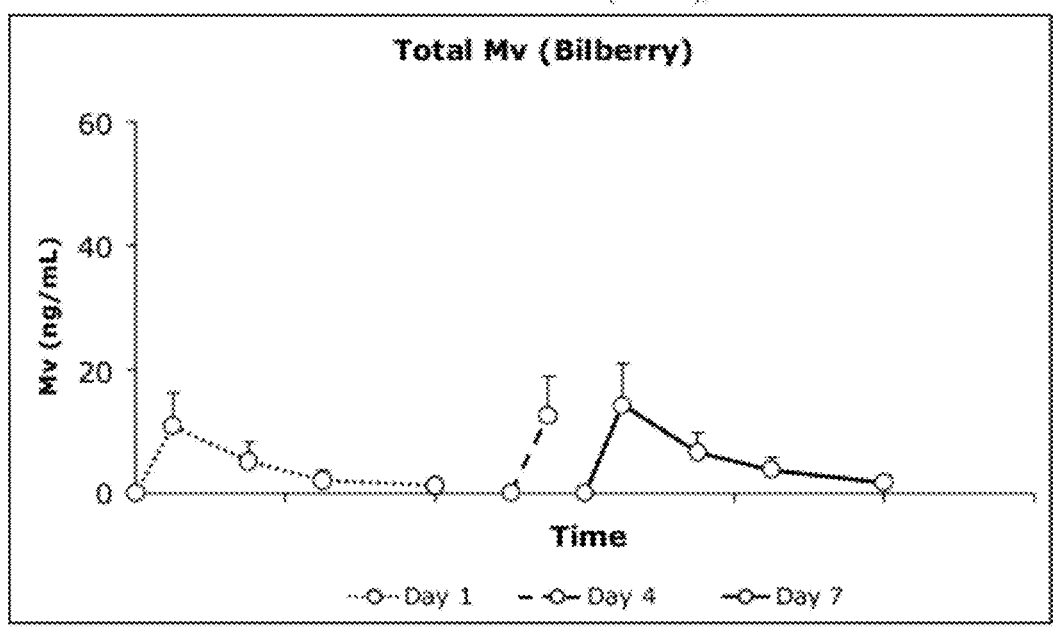
FIG. 40A provides total malvidin plasma levels in plasma at 4 hours, 1 day, 7 days and on day 4, the two points represent 0 and 0.5 hours respectively for bilberry extract without cysteine.
Figure 40B:
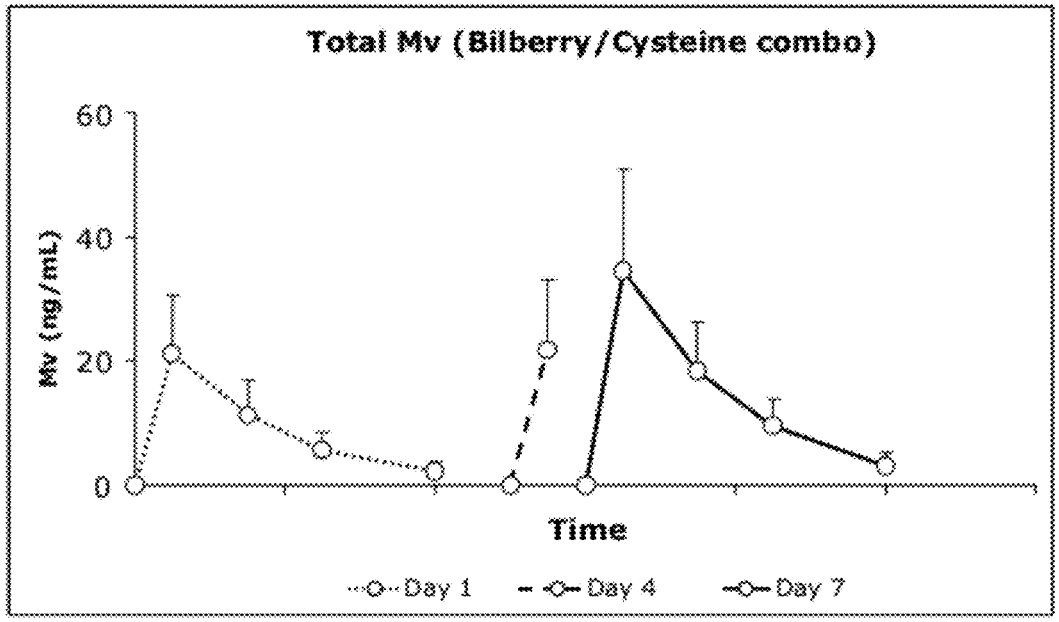
FIG. 40B provides total malvidin plasma levels in plasma at 4 hours, 1 day, 7 days and on day 4, the two points represent 0 and 0.5 hours respectively for bilberry extract with cysteine.

It was noted that when the pH value increased, the degradation of the extract increased. In all pH values tested, the L-glutathione (GSH) protected the anthocyanins. Additionally, the Protection Effect increased with pH values. In alkaline environments, the GSH had a greater stabilizing effect as seen in the table above and in FIGS. 19 and 20.

EXAMPLE 8

Sample a) 60 mg GSH (0.192 mmol) were placed into a 100 ml flask, dissolved and filled up to volume with sodium phosphate buffer (5% [w/w], pH=7.0). The sample was kept with stirring at 37° C. Samples were taken immediately after dissolution and after 1, 2, 3 and 4 hours of incubation. The samples were analyzed by HPLC for GSH and GSSG (representing the oxidized form of GSH).

Sample b) 60 mg reduced L-glutathione (0.192 mmol) were added to a 100 ml flask with 60 ml sodium phosphate buffer (5% [w/w], pH=7.0) and stirred until dissolution was complete. 60 mg bilberry extract [37% anthocyanosides] (0.048 mmol expressed as cyanidin-3-O-glucoside) were added, the flask was filled to volume with sodium phosphate buffer (5% [w/w], pH=7.0) and kept at 37° C. (water bath) with stirring. Samples were taken immediately after dissolution and after 1, 2, 3 and 4 hours of incubation. The samples were analyzed by HPLC for GSH and GSSG (representing the oxidized form of GSH).

From the tables below it was determined that GSH was oxidized to GSSG in aqueous buffer solution (pH=7.0) at 37° C. Addition of bilberry extract accelerated the oxidation of GSH to GSSG by a factor about 2 to about 3 suggesting that bilberry extract serves as partner for a redox reaction. Based on this result it was evident that the couple GSH/GSSG has a considerably low redox potential yielding oxidized GSSG and reduced anthocyanosides.

TABLE

Peak Area of GSH and GSSG and peak area ratio after incubation in buffer pH = 7.0 at 37° C.

| Incubation Time (hours) | GSH Sample | | | |
|---|---|---|---|---|
| | Peak Area GSH | Ratio % | Peak Area GSSG | Ratio % |
| 0 | 4760 | 92.3 | 394.9 | 7.7 |
| 1 | 4744 | 92.0 | 511.5 | 9.9 |
| 2 | 4220 | 81.9 | 763.2 | 14.8 |
| 3 | 4053 | 78.6 | 1051 | 20.4 |
| 4 | 3777 | 73.3 | 1209 | 23.5 |

TABLE

Peak Area of GSH and GSSG and peak area ratio after incubation in buffer pH = 7.0 at 37° C. in presence of bilberry extract

| Incubation Time (hours) | GSH + bilberry Sample | | | |
|---|---|---|---|---|
| | Peak Area GSH | Ratio % | Peak Area GSSG | Ratio % |
| 0 | 4760 | 92.3 | 394.9 | 7.7 |
| 1 | 4071 | 79.0 | 1260 | 24.4 |
| 2 | 3378 | 65.5 | 1722 | 33.4 |
| 3 | 3045 | 59.1 | 2033 | 39.4 |
| 4 | 2461 | 47.7 | 2447 | 47.5 |

Samples were prepared as outlined below in HPLC Analytical Method. Test stability samples were immediately acidified (to block degradation) and injected undiluted following the detailed description provided below.

Stability of Black Currant Extract 120 mg black currant extract/100 ml solution were incubated with 30 mg glutathione (GSH)/100 ml in buffered solution (pH=7.0) as the incubation medium used for CaCo-2 absorption tests.

These investigations provide information on the stability/degradation of selected black currant lead-anthocyanosides in analytical solutions and in the incubation medium used for the CaCo-2 test in presence of glutathione.

Delphindin-3-O-glucoside, (Dp-Glc), Delphinidin-3-O-rutinoside (Dp-Rut) and Cyanidin-3-O-rutinoside (Cn-Rut) were chosen for analysis.

Figure 13:
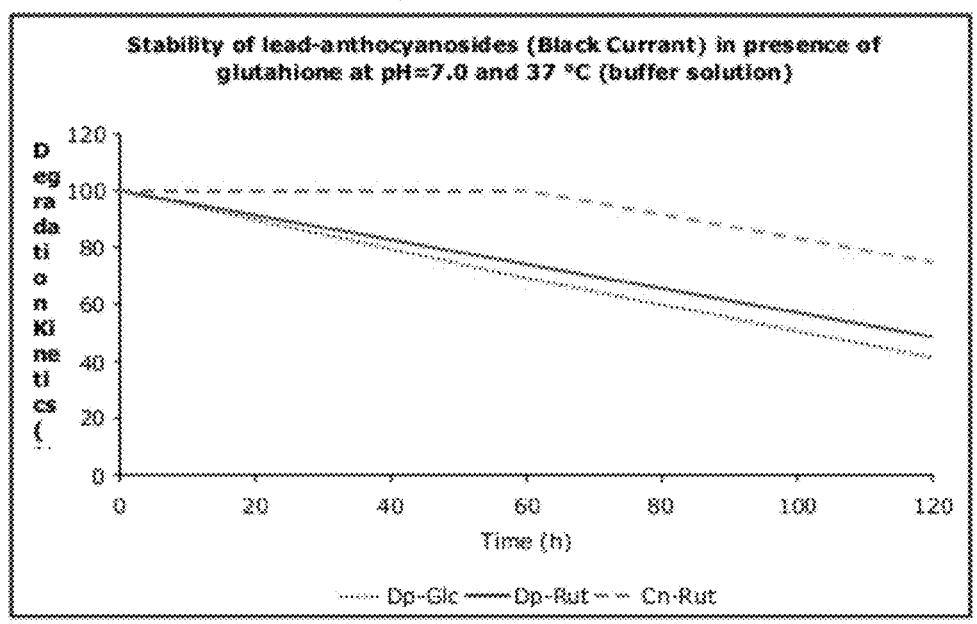
FIG. 13 demonstrates stability in buffered solution of lead anthocyanoside (Black current) in the presence of glutathione at a pH of 7 at 37° C. over time.
Figure 14:
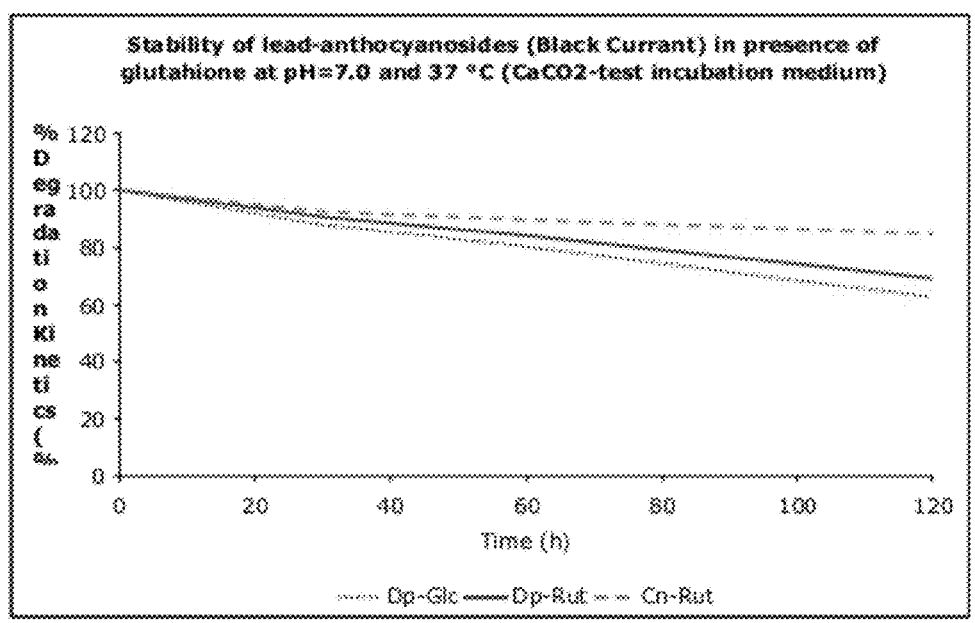
FIG. 14 demonstrates the stability in incubation medium of lead anthocyanoside (Black current) in the presence of glutathione with CaCo-2 cells at a pH of 7 at 37° C. over time.

These investigations showed that both delphinidin-glycosides investigated were more susceptible to degradation than cyanidin-rutinoside. Dp-glc was more susceptible than Dp-rut under the given conditions. All anthocyanosides investigated were slightly more stable in incubation medium resembling the ileal fluid than the buffered solution (See FIGS. 13 and 14). Most likely, the increase in stability is caused by the presence of putatively stabilizing ingredients in the complex medium (eventually re-cycling glutathione).

CaCo-2 cells were incubated with 120 mg black currant extract and 30 mg glutathione/100 ml medium at 37° C. for up to 2 hours. At 30, 60 and 120 minutes, 3 wells were processed for analysis by collection of the incubation medium and extraction of the anthocyanosides absorbed into the cells.

Figure 15:
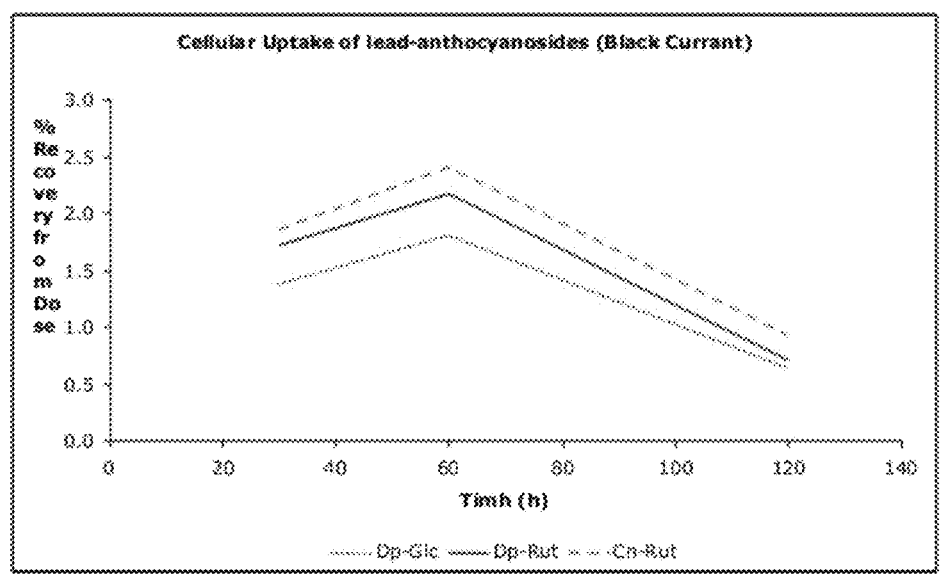
FIG. 15 demonstrates cellular uptake of lead-anthocyanosides into CaCo-2 cells.

As seen in FIG. 15, all 3 anthocyanosides investigated were absorbed into CaCo-2 cells. The highest absorption was observed for Cn-Rut after 60 minutes of incubation. At this time point the recovery of anthocyanosides in CaCo-2 cells amounts to 2.5% of the concentration determined in the supernatant incubation medium. Most interestingly, the % uptake resembles the stability of the anthocyanosides in buffered medium and incubation medium (without cells). It was further observed that for all anthocyanosides the maximum absorption is seen after 60 minutes of incubation.

60 mg bilberry extract ±30 mg glutathione/100 ml cell-free incubation media were held at 37° C. for 1 hour. Samples were analyzed prior or after the incubation period for 15 anthocyanosides present in bilberry extract.

This investigation provided information on the basic stability of the anthocyanosides in incubation medium (pH=7.0) at the conditions applied during CaCo-2 testing. Secondly, the effect of glutathione on the stability is elucidated.

Figure 16:
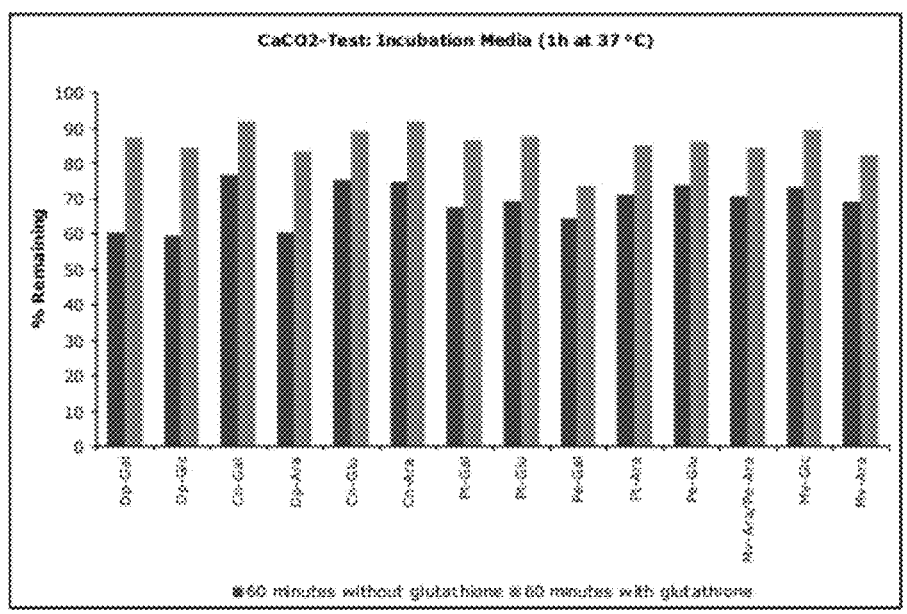
FIG. 16 provides degradation of bilberry anthocyanosides with/without glutathione (1 hour at 37° C., pH=7.0).

As seen in FIG. 16, all anthocyanosides were stabilized by glutathione. The most pronounced stabilization was observed for Dp-glycosides. This is of importance because Dp-glycosides are the most susceptible bilberry glucosides in terms of degradation at pH=7.0. From this analytical investigation it was determined that glutathione protects anthocyanosides from degradation at pH=7.0. Moreover it is noted that glutathione protects all anthocyanidin-structures present in bilberry.

A detailed analysis of the protection reveals that a tendency between protective potency and chemical structure of anthocyanidin exists. Dp, the most susceptible structure, is stabilized to the greatest extent whereas the protective effect for the most stable structure (Cn) is comparably low. In summary all anthocyanosides studied degraded less than 25% at pH=7.0 during 1 hour at 37° C. in presence of glutathione.

CaCo-2 cells were incubated with 60 mg bilberry extract with/without 30 mg glutathione/100 m medium at 37° C. for 1 hour. Thereafter 3 wells were processed for analysis by collection of the incubation medium and extraction of the anthocyanosides absorbed into the cells.

Figure 17:
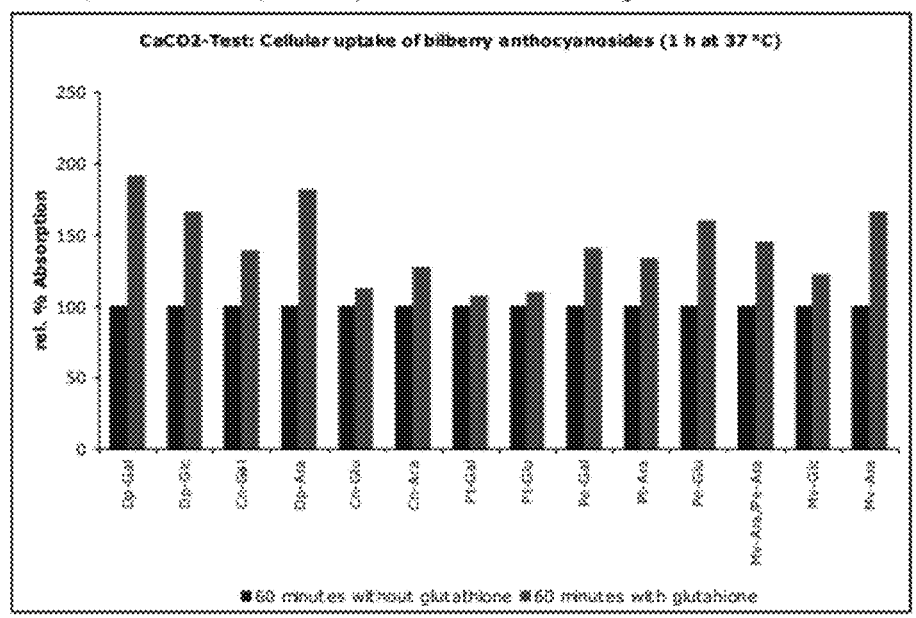
FIG. 17 demonstrates cellular uptake of bilberry anthocyanosides with/without glutathione into CaCo-2 cells.

As seen in FIG. 17, all bilberry anthocyanosides studied were better absorbed in presence of glutathione. This points to a correlation of an increased absorption with the stabilization of anthocyanosides with glutathione. The most likely explanation is that the degree of absorption of anthocyanosides is dependent on the concentration of intact anthocyanosides in the incubation media. In other words, the absorption of anthocyanosides may be dependent on a concentration gradient between the outer and the inside of the cells (the higher concentration outside, the higher the absorption). As glutathione was shown to increase the stability of anthocyanosides outside the cells, absorption into the cells follows the theory proposed.

EXAMPLE 9

Sample a) 60 mg bilberry extract [37% anthocyanosides] (0.048 mmol anthocyanosides expressed as cyanidin-3-O-glucoside) were added to a 100 ml flask with 60 ml sodium phosphate buffer (5% [w/w], pH=7.0), and stirred until dissolution was complete. A 1 ml sample was taken immediately and acidified with formic acid to pH=1.0 and analyzed by HPLC for the content of anthocyanosides (Fresh Sample). The remaining solution was kept for 4 hours at 37° C. (water bath) with stirring. Thereafter another sample (Blank sample), representing unprotected degradation, was taken and acidified.

Sample b) 20 mg L-cysteine (0.065 mmol) were added to a 100 ml flask with 60 ml sodium phosphate buffer (5% [w/w], pH=7.0) and stirred until dissolution was complete. 60 mg bilberry extract [37% anthocyanosides] (0.048 mmol expressed as cyanidin-3-O-glucoside) were then added to the flask and stir to fully dissolve, then kept for 4 hours at 37° C. (water bath) with stirring.

After 4 hours, samples were taken and acidified immediately with formic acid to pH=1.0 and analyzed by HPLC for the content of anthocyanosides. Degradation is expressed as decrease in peak area of individual peaks (calculated as % left after 4 hours).

From the table below it was concluded that anthocyanosides are substantially more stable at pH=7.0 at 37° C. in presence of L-cysteine when compared to blank (unprotected) samples. After 4 hours, the blank sample showed that about 25% of residual anthocyanosides were observed whereas the protected samples yielded more than 65% residual anthocyanosides.

TABLE

Peak Area of anthocyanosides after incubation for 4 hours at 37° C.

| Peak ID | Fresh solution Area | Blank Area | % left | L-cysteine 20 mg Area | % left |
|---|---|---|---|---|---|
| Dp-3-O-Gal | 654.4 | 50.9 | 7.8 | 331.3 | 50.6 |
| Dp-3-O-Glc | 726.6 | 46.3 | 6.4 | 350.8 | 48.3 |
| Cn-3-O-Gal | 465.8 | 191.1 | 41.0 | 360.2 | 77.3 |
| Cn-3-O-Glc | 987.9 | 410.3 | 41.5 | 797.5 | 80.7 |

Dp . . . Delphinidin, Cn . . . Cyanidin, Glc . . . Glucoside, Gal . . . Galactoside Samples were prepared as outlined above in the HPLC Analytical Method. Test stability samples were immediately acidified (to block degradation) and injected undiluted following the detailed description provided below.

EXAMPLE 10

Sample a) 60 mg bilberry extract [37% anthocyanosides] (0.048 mmol anthocyanosides expressed as cyanidin-3-O-glucoside) were added to a 100 ml flask and filled with 60 ml sodium phosphate buffer (5% [w/w], pH=7.0), and stirred until dissolution was complete. A 1 ml sample was taken immediately and acidified with formic acid to pH=1.0 and analyzed by HPLC for the content of anthocyanosides (Fresh Sample). The remaining solution was kept for 4 hours at 37° C. (water bath) with stirring. Thereafter another sample (Blank sample), representing unprotected degradation, was taken and acidified.

Samples b-e) 5, 10, 20 or 60 mg L-cysteine (0.041-0.492 mmol) were added to 100 ml flasks with 60 ml sodium phosphate buffer (5% [w/w], pH=7.0) and stirred until dissolution was complete. To each flask was 60 mg bilberry extract [37% anthocyanosides] (0.048 mmol anthocyanosides expressed as cyanidin-3-O-glucoside). Then stir to dissolve the bilberry extract and kept for 4 hours at 37° C. (water bath) with stirring.

After 4 hours, samples were taken, acidified immediately with formic acid to pH=1.0 and analyzed by HPLC for the content of anthocyanosides. Degradation is expressed as a decrease in the sum peak area for all anthocyanosides, calculated as % left after 4 hours.

From the tables below it was determined that anthocyanosides were substantially protected by L-cysteine in a dose-dependent manner.

TABLE

Peak Area of anthocyanosides after incubation for 4 hours at 37° C.

| L-cysteine added (mg) | Anthocyanoside left % Blank Sample | Anthocyanoside left % Protected Sample |
|---|---|---|
| 5 | 25.2 | 51.8 |
| 10 | 25.2 | 60.2 |
| 20 | 25.2 | 68.7 |
| 60 | 25.2 | 69.1 |

EXAMPLE 11

Materials
Bilberry capsules, provided by Omnica GmbH, sample No.: 20070601 and 20070602.
Sample No. 20070601 only contained bilberry extract, as blank sample
Sample No. 20070602 contained bilberry extract and 10% cysteine
5% Sodium phosphate buffer
Analysis Method
Agilent 1100 HPLC, UV-VIS detector at 530 nm
Experiment
To a 100 ml flask was added 60.0 g 5% Sodium phosphate buffer (pH=7.0) and 60.0 mg powder of bilberry extract from a capsule. The solution was sonicated until all the solid were fully dissolved. A sample was taken immediately and then the flask was placed into a 37° C. water bath and maintained for 4 hours to determine the residual ratio of anthocyanins.
Result and Conclusion
HPLC Data
The HPLC areas were used as a measure of the content of the compounds.
The content did not include un-substituted anthocyanidin base
Comparison of the two capsules (20070601 and 20070602)
The following tables and FIGS. 21 through 26 provide evidence that the use of cysteine helps to stabilize bilberry extract.

| Batch No. | Fresh Content Time zero | Final Content 4 hours | Residual Ratio % |
|---|---|---|---|
| 20070601 | 5327 | 1382 | 25.9 |
| 20070602 | 5008 | 3510 | 70.1 |

HPLC data

Peak Area

| Peak No. | Fresh solution of 20070601 | Final solution of 20070601 | Fresh solution of 20070602 | Final solution of 20070602 |
|---|---|---|---|---|
| 1 | 763.1 | 125.7 | 717.9 | 503.1 |
| 2 | 803.6 | 117.5 | 753.7 | 515.0 |
| 3 | 454.4 | 222.0 | 428.7 | 320.1 |
| 4 | 588.1 | 74.6 | 554.8 | 366.7 |
| 5 | 516.2 | 217.6 | 479.1 | 347.4 |
| 6 | 212.5 | 63.7 | 216.8 | 154.6 |
| 7 | 314.9 | 94.6 | 295.7 | 220.1 |
| 8 | 494.3 | 117.5 | 460.6 | 321.8 |
| 9 | 52.8 | 17.6 | 49.5 | 33.7 |
| 10 | 138.1 | 21.4 | 127.6 | 86.4 |
| 11 | 209.7 | 66.2 | 196.1 | 138.6 |
| 12 | 179.5 | 63.7 | 168.3 | 119.0 |
| 13 | 26.3 | 4.1 | 24.0 | 16.3 |

-continued

HPLC data

| Peak No. | Peak Area | | | |
|---|---|---|---|---|
| | Fresh solution of 20070601 | Final solution of 20070601 | Fresh solution of 20070602 | Final solution of 20070602 |
| 14 | 477.0 | 154.7 | 445.3 | 305.7 |
| 15 | 96.5 | 20.6 | 90.1 | 61.5 |
| Total | 5327 | 1382 | 5008 | 3510 |

Peak identification of HPLC chromatograms

| Peak No | anthocyanoside |
|---|---|
| 1 | Delphinidin 3-o-galactoside |
| 2 | Delphinidin 3-o-glucoside |
| 3 | Cyanidin 2-o-galactoside |
| 4 | Delphinidin 3-o-arabinoside |
| 5 | Cyanidin 3-o-glucoside |
| 6 | Petunidin 3-o-galactoside |
| 7 | Cyanidin 3-o-arabinoside |
| 8 | Petunidin 3-o-glucoside |
| 9 | Peonidin 3-o-galactoside |
| 10 | Petunidin 3-o-arabinoside |
| 11 | Peonidin 3-o-glucoside |
| 12 | Malvidin 3-o-galactoside |
| 13 | Peonidin 3-o-arabinoside |
| 14 | Malvidin 3-o-arabinoside |
| 15 | Malvidin 3-o-glucoside |

Methods

Culturing of CaCo-2 cells

CaCo-2 cells were cultured in Dulbeccos's Modified Eagle Medium containing 20% fetal bovine serum, 1,2% nonessential amino acids, 0.83 mM L-glutamine, 1.2% penicillin-streptomycin and 0.1% mercaptoethanol in an atmosphere of 5% $CO_2$ and 95% air at 37° C.

Cells were grown in 75 $cm^2$ culture-flasks (T75) and sub-cultured after one week (every other day washed with PBS buffer, removed with trypsin and transferred to an new culture flask).

CaCo-2 test

For experiments, cells were seeded in 6 well plates at a density of $3 \times 10^5$ cells per well and grown in an atmosphere of 5% $CO_2$ and 95% air at 37° C. 7 to 8 days until confluency was reached. The cells were washed with PBS buffer, incubated with 4 ml medium containing bilberry (30-60 mg/100 ml medium) or black currant extract (30-60 mg/100 ml medium) for 30, 60 or 120 minutes. For stabilizing experiments, medium containing 30 mg glutathione/100 ml was used.

After the corresponding incubation time, 900 μl of incubation medium used was taken from each well and mixed with 100 μl formic acid. The cells were washed with PBS buffer and removed using 1 ml of 10% formic acid. Cells were sonicated 3 times for 30 seconds, centrifuged for 10 minutes and the pellets were discarded. The supernatant was used as sample for HPLC.

For comparison, the stability of anthocyanosides was tested in incubation medium without cells at 37° C. between 0 and 120 min. Incubation medium was stabilized with formic acid as described above.

HPLC Analytical Method (Materials, Instruments and Methods):

Acetonitrile, Methanol (HPLC grade), Formic acid (AR), Distilled water. Reference standard: Cyanidin-3-O-glucoside (Cl salt, Item 1201, Polyphenols Laboratories AS, Norway)

Figure 18:
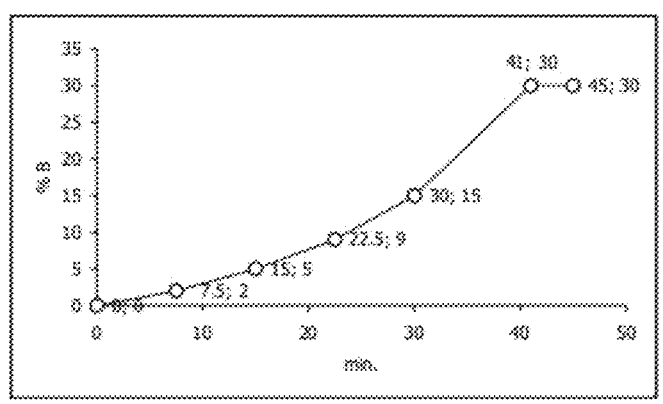
FIG. 18 provides the gradient profile for HPLC analysis of the CaCo-2 experiments.

Pump: Merck Quaternary Gradient pump 6200
Autosampler: Merck AS 2000,
Detector: HP-MVD 1050 set to 520 nm
Column: Bischoff, Hypersil ODS, 250×4.6 mm
Mobile phase: A: formic acid/water=10/90
B:methanol/acetonitrile/formic acid/water=20/20/10/50
Gradient profile: (See FIG. 18)
Flow rate: 1.5 ml/min
Injection volume: 20 μl
Temperature: 45° C.
Detection: 520 nm
Calibration 5-point calibration with cyaniding-3-O-glucoside Quantitation: External standardization based on linear regression analysis. The response factors of all anthocyanosides separated is quantitified against cyanidin-3-O-glucoside.

Standard preparation (Cyanidin-3-O-glucoside)

Transfer an appropriate amount of standard into a 10 ml flask and dissolve in 1 ml MeOH. The flask was filled to volume with 10% phosphoric acid. Dilutions were prepared in 10% phosphoric acid.

Sample preparation

Test solutions from incubation experiments (with/without cells and with/without stabilizing agents) were used for analysis after stabilization of anthocyanosides with formic acid. Samples were cleared by filtration prior to injection on to HPLC-system.

For example, 0.500 g Bilberry extract was dissolved in 10 ml methanol with 2% HCl and ultrasonicated for 2 minutes. 1 ml of solution was transferred into a 10 ml flask and diluted to the volume with 10% phosphoric acid. Sample was injected onto the HPLC-system.

Data evaluation

% degradation is given in % of the initial values obtained.

% uptake into cells refers to the ratio of the amounts obtained in the incubation medium at the corresponding time to the amount found in the cells.

Stabilized anthocyanins at various pH values

Raw Materials

Bilberry Extract, 20070602,Omnica GmbH
Reduced L-glutathione, Bio-Chemical reagent
Sodium phosphate buffer, pH values from 3.0 to 11.0

20 mg reduced L-glutathione were added to 100 ml flasks with 60 ml 5% sodium phosphate buffer (for appropriate pH). After the solid was totally dissolved, 60 mg bilberry extract was added with stirring and put into water bath at 37° C. Samples from the various pH buffered solutions were withdrawn and analyzed by HPLC by the methods described above.

EXAMPLE 12

Product (Bilberry extract, Omnica GmbH (Hamburg) was adjusted to 37% (m/m) anthocyanosides. Based on an average content of 0.3-0.4% (m/m) of anthocyanosides in fresh bilberries, the extract at hand represented a 100:1 concentrate. The remaining 63% of the extract are represented in the majority by proteins and carbohydrates occurring in fresh berries. 500 mg bilberry extract and 500 mg bilberry extract with 50 mg L-Cysteine were combined to produce the bilberry/cysteine combo utilized below. Bilberry extract noted below is the product described above without the addition of cysteine.

12 volunteers received bilberry extract for 7 consecutive days. After a 1 week wash-out period the same volunteers received Bilberry/Cysteine combo for 7 consecutive days.

The design was a randomized, cross-over observation.

Plasma samples were taken during each period on day 1 (prior to and 0.5, 1.5, 2.5 and 4 hours after treatment), 4 (prior to and 0.5 hours after treatment) and 7 ((prior to and 0.5, 1.5, 2.5 and 4 hours after treatment) of the corresponding treatment.

The main target of the study was to determine the plasma levels of the anthocyanins present in both formulations.

In a first run of analysis, all anthocyanins present in plasma were extracted by solid phase extraction and after collection hydrolyzed to yield the anthocyanidins. This procedure was chosen to provide information on the real absorption of bilberry anthocyanins from both formulations and to avoid erroneous conclusions due to metabolism of the compounds absorbed. Each metabolite (i.e. glucuronides) would not count as absorbed from the formulations although the efficacy resides in the anthocyanidin skeleton and not in a specific glycosidation pattern.

The analysis comprised HPLC with UV-detection at 540 nm. Quantification was based on external standardization with authentic anthocyanidin standards. The recovery of the method was estimated with delphinidin-3-O-glucoside and cyanidin-3-O-glucoside. These two bilberry anthocyanins were spiked to blank plasma, extracted and hydrolyzed in the same way as the study samples. It was shown that the recovery is >95%. The stability of the study samples was confirmed by spiked blank plasma samples treated and stored exactly the same ways as the study samples.

Pharmacokinetic parameters were calculated using standard non-compartmental methods.

LIST OF ABBREVIATIONS

| | |
|---|---|
| ANOVA | Analysis of Variances |
| Ara | Arabinose |
| AUC | Area under the Curve |
| $AUC_{(0-inf)}$ | AUC from time-point O to infinity. |
| $AUC_{(0-t)}$ | AUC from time-point O to the last measured time-point. |
| $AU_{(0-4\,h)}$ | Area under the Curve from time-point O to 8 hours. |
| β | Elimination rate constant |
| $C_{max}$ | Maximum plasma concentration obtained |
| Cn | Cyanidin |
| CV | Coefficient of Variation |
| Dp | Delphinidin |
| Gal | Galactose |
| Glc | Glucose |
| HPLC | High Performance Liquid Chromatography |
| MS | Mass Spectrometry |
| Mv | Malvidin |
| Pe | Peonidin |
| Pt | Petunidin |
| $t_{1/2}$ | Terminal plasma half-life |
| $T_{max}$ | Time to maximum plasma concentration ($C_{max}$) |
| UV | Ultra-Violet |

Study Results:

FIGS. 27 through 40 demonstrate that anthocyanidin concentration of bilberry/cysteine combinations is increased by at least twice the amount of anthocyanidin concentration in blood plasma when compared to samples from bilberry without the addition of cysteine. This can be seen in total anthocyanidin content as well as individual anthocyanidins.

The following tables provide the mean values±standard deviation (s.d.) of the plasma levels determined for the 5 anthocyanidins present in bilberry (i.e. cyanidin [Cn], delphindin [Dp], petunidin [Pt], peonidin [Pe] and malvidin [Mv]).

TOTAL CYANIDIN PLASMA LEVELS (NG/ML), MEAN ± S.D.

| | | Total Cn (ng/mL) | | | |
|---|---|---|---|---|---|
| | | Bilberry | | Bilberry/Cysteine combo | |
| | Time (h) | Mean | s.d. | Mean | s.d |
| Day 1 | 0 | BLD | n.a. | BLD | n.a. |
| | 0.5 | 22.3 | 7.2 | 35.7 | 8.6 |
| | 1.5 | 18.4 | 5.7 | 27.2 | 8.3 |
| | 2.5 | 9.1 | 4.1 | 14.5 | 5.8 |
| | 4 | 3.2 | 1.9 | 5.2 | 2.4 |
| Day 4 | 5 | BLD | n.a. | BLD | n.a. |
| | 5.5 | 17.9 | 6 | 30.1 | 6.8 |
| Day 7 | 6 | BLD | n.a. | BLD | n.a. |
| | 6.5 | 26.3 | 8.6 | 51.7 | 12.4 |
| | 7.5 | 23.9 | 6.7 | 29.5 | 9.6 |
| | 8.5 | 14.6 | 5.4 | 25.6 | 7.5 |
| | 10 | 5.9 | 2.7 | 7.8 | 3.2 |

BLD ... BELOW LIMIT OF DETERMINATION (<1 NG/ML), N.A. ... NOT APPLICABLE

TOTAL DELPHINIDIN PLASMA LEVELS (NG/ML), MEAN ± S.D.

| | | Total Dp (ng/mL) | | | |
|---|---|---|---|---|---|
| | | Bilberry | | Bilberry/Cysteine combo | |
| | Time (h) | Mean | s.d. | Mean | s.d |
| Day 1 | 0 | BLD | n.a. | BLD | n.a. |
| | 0.5 | 18.6 | 6.9 | 29.2 | 9.3 |
| | 1.5 | 12.4 | 6.2 | 20.7 | 7.4 |
| | 2.5 | 6.2 | 3.1 | 12.5 | 5.3 |
| | 4 | 3.9 | 1.8 | 5.1 | 2.6 |
| Day 4 | 0 | BLD | n.a. | BLD | n.a. |
| | 0.5 | 19.4 | 7.4 | 32.6 | 11.5 |
| Day 7 | 0 | BLD | n.a. | BLD | n.a. |
| | 0.5 | 27.4 | 8.5 | 53.7 | 24.8 |
| | 1.5 | 14.9 | 6.8 | 34.9 | 13.8 |
| | 2.5 | 7.1 | 4.5 | 16.3 | 8.2 |
| | 4 | 4.2 | 3.5 | 6.8 | 3.7 |

TOTAL PETUNIDIN PLASMA LEVELS (NG/ML), MEAN ± S.D.

| | | Total Pt (ng/mL) | | | |
|---|---|---|---|---|---|
| | | Bilberry | | Bilberry/Cysteine combo | |
| | Time (h) | Mean | s.d. | Mean | s.d |
| Day 1 | 0 | BLD | n.a. | BLD | n.a. |
| | 0.5 | 10.2 | 4.5 | 19.8 | 7.1 |
| | 1.5 | 5.8 | 3.7 | 8.9 | 4.5 |
| | 2.5 | 3.1 | 2.3 | 5.2 | 2.3 |
| | 4 | 1.2 | 1.6 | 1.9 | 1.6 |
| Day 4 | 0 | BLD | n.a. | BLD | n.a. |
| | 0.5 | 9.2 | 4.2 | 16.8 | 7.6 |
| Day 7 | 0 | BLD | n.a. | BLD | n.a. |
| | 0.5 | 14.4 | 6.7 | 29.8 | 12.6 |
| | 1.5 | 8.1 | 4.8 | 14.3 | 6.4 |
| | 2.5 | 3.7 | 1.9 | 6.2 | 3.7 |
| | 4 | 1.6 | 1.5 | 2.9 | 1.5 |

TOTAL MALVIDIN PLASMA LEVELS (NG/ML), MEAN ± S.D.

| | | Total Mv (ng/mL) | | | |
| --- | --- | --- | --- | --- | --- |
| | | Bilberry | | Bilberry/Cysteine combo | |
| | Time (h) | Mean | s.d. | Mean | s.d |
| Day 1 | 0 | BLD | n.a. | BLD | n.a. |
| | 0.5 | 10.9 | 5.4 | 21.1 | 9.6 |
| | 1.5 | 5.2 | 3.1 | 11.2 | 5.8 |
| | 2.5 | 2.1 | 1.5 | 5.8 | 2.6 |
| | 4 | 1.2 | 1 | 2.3 | 1.4 |
| Day 4 | 0 | BLD | n.a. | BLD | n.a. |
| | 0.5 | 12.5 | 6.3 | 21.7 | 11.4 |
| Day 7 | 0 | BLD | n.a. | BLD | n.a. |
| | 0.5 | 14.3 | 6.8 | 34.5 | 16.4 |
| | 1.5 | 6.4 | 3.2 | 18.5 | 7.9 |
| | 2.5 | 3.8 | 1.8 | 9.6 | 4.4 |
| | 4 | 1.6 | 1.2 | 3.1 | 1.9 |

TOTAL PEONIDIN PLASMA LEVELS (NG/ML), MEAN ± S.D.

| | | Total Pe (ng/mL) | | | |
| --- | --- | --- | --- | --- | --- |
| | | Bilberry | | Bilberry/Cysteine combo | |
| | Time (h) | Mean | s.d. | Mean | s.d |
| Day 1 | 0 | BLD | n.a. | BLD | n.a. |
| | 0.5 | 4.0 | 2.3 | 7.9 | 3.6 |
| | 1.5 | 2.2 | 1.9 | 3.2 | 2.1 |
| | 2.5 | 1 | 1.1 | 1.8 | 1 |
| | 4 | BLD | n.a. | 1 | n.a. |
| Day 4 | 0 | BLD | n.a. | BLD | n.a. |
| | 0.5 | 4.6 | 2.7 | 8.2 | 4.4 |
| Day 7 | 0 | BLD | n.a. | BLD | n.a. |
| | 0.5 | 6.3 | 3.0 | 12.2 | 5.3 |
| | 1.5 | 2.7 | 1.5 | 7.5 | 3.7 |
| | 2.5 | 1.4 | 0.8 | 3.8 | 1.9 |
| | 4 | BLD | n.a. | 1.4 | 1.1 |

The following Tables provide the pharmacokinetic parameters calculated from the mean plasma levels observed.

PHARMACOKINETIC PARAMETERS CALCULATED FOR TOTAL CYANIDIN

| | Day 1 | | Day 7 | |
| --- | --- | --- | --- | --- |
| Parameter | Bilberry | Bilberry/Cysteine combo | Bilberry | Bilberry/Cysteine combo |
| $C_{max}$ (ng/mL) | 22.3 | 35.7 | 26.3 | 51.7 |
| $T_{max}$ (h) | 0.5 | 0.5 | 0.5 | 0.5 |
| $AUC_{0-t}$ (ng × h/mL) | 48.9 | 76 | 66.3 | 106.1 |
| $t_{1/2}$ (h) | 1.20 | 1.23 | 1.56 | 1.34 |
| $AUC_{0-inf}$ (ng × h/mL) | 64.7 | 101.7 | 99.2 | 155.6 |

PHARMACOKINETIC PARAMETERS CALCULATED FOR TOTAL DELPHINIDIN

| | Day 1 | | Day 7 | |
| --- | --- | --- | --- | --- |
| Parameter | Bilberry | Bilberry/Cysteine combo | Bilberry | Bilberry/Cysteine combo |
| $C_{max}$ (ng/mL) | 18.6 | 29.2 | 27.4 | 53.7 |
| $T_{max}$ (h) | 0.5 | 0.5 | 0.5 | 0.5 |
| $AUC_{0-t}$ (ng × h/mL) | 37.0 | 62.1 | 47.5 | 100.7 |
| $t_{1/2}$ (h) | 1.5 | 1.4 | 1.3 | 1.1 |
| $AUC_{0-inf}$ (ng × h/mL) | 50.5 | 86.8 | 60.5 | 127.5 |

PHARMACOKINETIC PARAMETERS CALCULATED FOR TOTAL PETUNIDIN

| | Day 1 | | Day 7 | |
| --- | --- | --- | --- | --- |
| Parameter | Bilberry | Bilberry/Cysteine combo | Bilberry | Bilberry/Cysteine combo |
| $C_{max}$ (ng/mL) | 10.2 | 19.8 | 14.4 | 29.8 |
| $T_{max}$ (h) | 0.5 | 0.5 | 0.5 | 0.5 |
| $AUC_{0-t}$ (ng × h/mL) | 18.2 | 31.7 | 24.7 | 46.6 |
| $t_{1/2}$ (h) | 0.6 | 0.7 | 0.6 | 0.7 |
| $AUC_{0-inf}$ (ng × h/mL) | 1.1 | 1.1 | 1.1 | 1.0 |

PHARMACOKINETIC PARAMETERS CALCULATED FOR TOTAL PEONIDIN

| | Day 1 | | Day 7 | |
| --- | --- | --- | --- | --- |
| Parameter | Bilberry | Bilberry/Cysteine combo | Bilberry | Bilberry/Cysteine combo |
| $C_{max}$ (ng/mL) | 4.0 | 7.9 | 6.3 | 12.2 |
| $T_{max}$ (h) | 0.5 | 0.5 | 0.5 | 0.5 |
| $AUC_{0-t}$ (ng × h/mL) | 6.5 | 12.1 | 9.2 | 22.5 |
| $t_{1/2}$ (h) | 1.0 | 1.2 | 0.9 | 1.1 |
| $AUC_{0-inf}$ (ng × h/mL) | 7.9 | 15.2 | 11.0 | 28.5 |

PHARMACOKINETIC PARAMETERS CALCULATED FOR TOTAL MALVIDIN

| | Day 1 | | Day 7 | |
| --- | --- | --- | --- | --- |
| Parameter | Bilberry | Bilberry/Cysteine combo | Bilberry | Bilberry/Cysteine combo |
| $C_{max}$ (ng/mL) | 10.9 | 21.1 | 14.3 | 34.5 |
| $T_{max}$ (h) | 0.5 | 0.5 | 0.5 | 0.5 |
| $AUC_{0-t}$ (ng × h/mL) | 16.9 | 36.0 | 23.1 | 58.7 |
| $t_{1/2}$ (h) | 1.1 | 1.1 | 1.1 | 1.0 |
| $AUC_{0-inf}$ (ng × h/mL) | 20.2 | 45.1 | 29.3 | 72.6 |

EXAMPLE 13

Sample preparation:

Sample A was the same as the blank sample of example 1.

Sample B: 48 mg (9.5% by weight of reduced glutathione) beer yeast extract was added to a 100 ml flask with 60.0 ml 5% Sodium phosphate buffer (pH=7.0). The solution was stirred until homogeneous and then 60 mg (0.049 mmol of anthocyanins) bilberry extract was added with stirring until uniform. The sample was placed into a 37° C. water bath for 4 hours with stirring. Degradation ratio analysis was monitored by HPLC.

Sample C: The preparation was the same as example B with the proviso that the amount of beer yeast extract was 120 mg.

Results:

| Sample | A | B | C |
|---|---|---|---|
| Residue ratio | 22.1% | 50.9% | 77.9% |

HPLC test parameters were the same as the above example.

The present example represents a positive protective effect of beer yeast extract on diminishing the degradation of the anythocyanin content of the samples.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety.

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method to increase the bioavailability of an anthocyanin extract consisting of administering to a subject a bilberry extract and cysteine.

2. The method of claim 1, wherein the mole ratio of cysteine to bilberry extract is about 0.1 to about 10.

3. The method of claim 1, wherein the plasma concentration of the bilberry extract in the presence of cysteine post four hours of administration is at least twice the amount of plasma concentration of bilberry extract absent the presence of cysteine.

* * * * *